US009421045B2

(12) United States Patent
Justin

(10) Patent No.: US 9,421,045 B2
(45) Date of Patent: Aug. 23, 2016

(54) BONE STABILIZATION DEVICE AND METHOD

(71) Applicant: FlexFix LLC, Logan, UT (US)

(72) Inventor: Daniel F Justin, Orlando, FL (US)

(73) Assignee: FlexFix, LLC, Logan, UT (US)

(*) Notice: Subject to any disclaimer, the term of this patent is extended or adjusted under 35 U.S.C. 154(b) by 201 days.

(21) Appl. No.: 14/220,132

(22) Filed: Mar. 20, 2014

(65) Prior Publication Data

US 2014/0207138 A1 Jul. 24, 2014
US 2016/0128742 A9 May 12, 2016

Related U.S. Application Data

(63) Continuation of application No. 13/423,914, filed on Mar. 19, 2012, now Pat. No. 8,834,468, which is a continuation of application No. 12/027,521, filed on Feb. 7, 2008, now Pat. No. 8,167,881, which is a continuation-in-part of application No. 11/777,846, filed on Jul. 13, 2007, now abandoned, and a continuation-in-part of application No. 11/777,872, filed on Jul. 13, 2007, now abandoned, and a continuation-in-part of application No. 11/777,892, filed on Jul. 13, 2007, now Pat. No. 8,128,626.

(60) Provisional application No. 60/913,696, filed on Apr. 24, 2007.

(51) Int. Cl.
A61B 17/72 (2006.01)
A61B 17/70 (2006.01)
A61B 17/80 (2006.01)
(Continued)

(52) U.S. Cl.
CPC ............ *A61B 17/72* (2013.01); *A61B 17/7044* (2013.01); *A61B 17/7059* (2013.01); *A61B 17/7071* (2013.01); *A61B 17/7208* (2013.01); *A61B 17/7233* (2013.01); *A61B 17/7275* (2013.01); *A61B 17/80* (2013.01); *A61B 17/864* (2013.01); *A61B 17/866* (2013.01); *A61F 2/91* (2013.01); *A61M 29/02* (2013.01); *A61B 17/7064* (2013.01); *A61B 2017/00004* (2013.01); *A61F 2/0077* (2013.01); *A61F 2/82* (2013.01); *A61F 2220/0075* (2013.01); *A61L 2400/16* (2013.01); *A61L 2430/02* (2013.01)

(58) Field of Classification Search
USPC ............ 606/62–68, 108, 194, 198; 623/1.11, 623/1.15
See application file for complete search history.

(56) References Cited

U.S. PATENT DOCUMENTS 4,177,524 A 12/1979 Grell et al.
4,204,531 A 5/1980 Aginsky
(Continued)

FOREIGN PATENT DOCUMENTS

FR 2801189 11/1999
WO WO 98/38918 9/1998
(Continued)

OTHER PUBLICATIONS

International Preliminary Report on Patentability in PCT/2008/061047 dated Oct. 27, 2009, 9 pages.
International Search Report and Written Opinion in PCT/2008/061047 dated Nov. 14, 2008, 11pgs.
Miller et al., "Performance Evaluation of a Cement-augmented Intramedullary Fixation System for Pathologic Lesions of the Femoral Shaft", Clinical Orthopaedics and Related Research, No. 221, Aug. 1987, p. 246-254.

*Primary Examiner* — Jan Christopher Merene
*Assistant Examiner* — Steven Cotroneo

(57) ABSTRACT

There is disclosed a device and method for stabilizing a bone. The device includes a polymer with a glass transition temperature. The polymer is relatively deformable at a temperature above the glass transition temperature and relatively rigid at a temperature below the glass transition temperature. The device, while the polymer is above the glass transition temperature, is responsive to a bending force to bend during insertion into the intramedullary canal of the bone. The device, while the polymer is below the glass transition temperature, is relatively rigid and able to provide reinforcement to the bone.

6 Claims, 43 Drawing Sheets

(51) Int. Cl.
*A61B 17/86* (2006.01)
*A61F 2/91* (2013.01)
*A61M 29/02* (2006.01)
A61B 17/00 (2006.01)
A61F 2/00 (2006.01)
A61F 2/82 (2013.01)

(56) References Cited

U.S. PATENT DOCUMENTS

| | | | |
|---|---|---|---|
| 4,222,128 A | 9/1980 | Tomonaga et al. | |
| 4,262,665 A | 4/1981 | Roalstad et al. | |
| 4,268,468 A | 5/1981 | Esper et al. | |
| 4,375,810 A * | 3/1983 | Belykh | A61B 17/72 606/62 |
| 4,409,974 A * | 10/1983 | Freedland | A61B 17/0401 606/232 |
| 4,453,539 A | 6/1984 | Raftopoulos et al. | |
| 4,457,301 A | 7/1984 | Walker | |
| 4,522,200 A | 6/1985 | Stednitz | |
| 4,721,103 A | 1/1988 | Freedland | |
| 4,854,312 A | 8/1989 | Raftopoulos et al. | |
| 4,932,969 A | 6/1990 | Frey et al. | |
| 5,037,442 A | 8/1991 | Wintermantel et al. | |
| 5,053,035 A | 10/1991 | McLaren | |
| 5,108,398 A | 4/1992 | McQueen et al. | |
| 5,108,404 A | 4/1992 | Scholten et al. | |
| 5,135,527 A | 8/1992 | Ender | |
| 5,190,546 A * | 3/1993 | Jervis | A61B 17/0642 128/833 |
| 5,281,225 A | 1/1994 | Vicenzi | |
| 5,324,307 A * | 6/1994 | Jarrett | A61B 17/064 525/415 |
| 5,364,398 A | 11/1994 | Chapman et al. | |
| 5,376,120 A | 12/1994 | Sarver et al. | |
| 5,423,850 A | 6/1995 | Berger | |
| 5,480,400 A | 1/1996 | Berger | |
| 5,501,695 A | 3/1996 | Anspach et al. | |
| 5,620,445 A | 4/1997 | Brosnahan et al. | |
| 5,653,709 A | 8/1997 | Frigg | |
| 5,720,753 A | 2/1998 | Sander et al. | |
| 5,725,541 A | 3/1998 | Anspach et al. | |
| 5,782,865 A | 7/1998 | Grotz et al. | |
| 5,849,004 A | 12/1998 | Bramlet et al. | |
| 5,855,579 A | 1/1999 | James et al. | |
| 6,083,244 A | 7/2000 | Lubbers et al. | |
| 6,127,597 A | 10/2000 | Beyar et al. | |
| 6,183,474 B1 | 2/2001 | Bramlet et al. | |
| 6,206,880 B1 | 3/2001 | Karladani | |
| 6,245,102 B1 | 6/2001 | Jayaraman | |
| 6,248,110 B1 | 6/2001 | Reiley et al. | |
| 6,261,289 B1 * | 7/2001 | Levy | 606/63 |
| 6,299,635 B1 | 10/2001 | Frantzen | |
| 6,312,455 B2 | 11/2001 | Duerig et al. | |
| 6,371,989 B1 | 4/2002 | Chauvin et al. | |
| 6,413,539 B1 | 7/2002 | Shalaby | |
| 6,423,067 B1 | 7/2002 | Eisermann | |
| 6,475,237 B2 | 11/2002 | Drasler et al. | |
| 6,491,718 B1 | 12/2002 | Ahmad | |
| 6,506,211 B1 | 1/2003 | Skubitz et al. | |
| 6,511,748 B1 * | 1/2003 | Barrows | A61L 27/48 428/292.1 |
| 6,551,321 B1 | 4/2003 | Burkinshaw et al. | |
| 6,554,833 B2 | 4/2003 | Levy et al. | |
| 6,582,453 B1 | 6/2003 | Tran et al. | |
| 6,613,081 B2 | 9/2003 | Kim et al. | |
| 6,626,937 B1 | 9/2003 | Cox | |
| 6,682,554 B2 | 1/2004 | Oepen et al. | |
| 6,709,454 B1 | 3/2004 | Cox et al. | |
| 6,736,818 B2 | 5/2004 | Perren et al. | |
| 6,746,477 B2 | 6/2004 | Moore | |
| 6,746,479 B2 | 6/2004 | Ehr et al. | |
| 6,755,862 B2 | 6/2004 | Kynan | |
| 6,761,731 B2 | 7/2004 | Majercak | |
| 6,764,506 B2 | 7/2004 | Roubin et al. | |
| 6,764,507 B2 | 7/2004 | Shanley et al. | |
| 6,770,088 B1 | 8/2004 | Jang | |
| 6,770,089 B1 | 8/2004 | Hong et al. | |
| 6,776,793 B2 | 8/2004 | Brown et al. | |
| 6,783,530 B1 | 8/2004 | Levy | |
| 6,790,227 B2 | 9/2004 | Burgermeister | |
| 6,805,706 B2 | 10/2004 | Solovay et al. | |
| 6,808,561 B2 | 10/2004 | Genge et al. | |
| 6,866,805 B2 | 3/2005 | Hong et al. | |
| 6,896,696 B2 | 5/2005 | Doran et al. | |
| 6,911,048 B2 | 6/2005 | Fernandez et al. | |
| 6,939,373 B2 | 9/2005 | Gomez et al. | |
| 6,955,686 B2 | 10/2005 | Majercak et al. | |
| 6,962,603 B1 | 11/2005 | Brown et al. | |
| 6,979,349 B1 | 12/2005 | Dang et al. | |
| 6,997,946 B2 | 2/2006 | Girton et al. | |
| 6,998,060 B2 | 2/2006 | Tomonto | |
| 7,005,136 B2 | 2/2006 | Nathan et al. | |
| 7,025,777 B2 | 4/2006 | Moore | |
| 7,029,493 B2 | 4/2006 | Majercak et al. | |
| 7,044,963 B2 | 5/2006 | Richter | |
| 7,052,498 B2 | 5/2006 | Levy et al. | |
| 7,060,088 B1 | 6/2006 | Fischell et al. | |
| 7,081,130 B2 | 7/2006 | Jang | |
| 7,094,255 B2 | 8/2006 | Penn et al. | |
| 7,101,391 B2 | 9/2006 | Scheuermann et al. | |
| 7,108,714 B1 | 9/2006 | Becker | |
| 7,112,216 B2 | 9/2006 | Gregorich | |
| 7,670,339 B2 | 3/2010 | Levy et al. | |
| 7,806,900 B2 | 10/2010 | Rabiner | |
| 7,811,284 B2 | 10/2010 | Rabiner et al. | |
| 7,811,290 B2 | 10/2010 | Rabiner | |
| 7,879,041 B2 | 2/2011 | Rabiner et al. | |
| 8,834,468 B2 | 9/2014 | Justin | |
| 2001/0020181 A1 | 9/2001 | Layne | |
| 2001/0051814 A1 | 12/2001 | Shalaby | |
| 2002/0032444 A1 * | 3/2002 | Mische | 606/63 |
| 2002/0120291 A1 | 8/2002 | Shalaby | |
| 2002/0165544 A1 | 11/2002 | Perren et al. | |
| 2003/0109932 A1 * | 6/2003 | Keynan | 623/23.18 |
| 2004/0199246 A1 * | 10/2004 | Chu et al. | 623/1.32 |
| 2004/0230193 A1 * | 11/2004 | Cheung et al. | 606/63 |
| 2005/0216007 A1 * | 9/2005 | Woll et al. | 606/62 |
| 2006/0264945 A1 * | 11/2006 | Edidin et al. | 606/63 |
| 2006/0264950 A1 | 11/2006 | Nelson et al. | |
| 2006/0264951 A1 | 11/2006 | Nelson et al. | |
| 2006/0264952 A1 | 11/2006 | Nelson et al. | |
| 2007/0213725 A1 | 9/2007 | Hack et al. | |
| 2007/0233105 A1 | 10/2007 | Nelson et al. | |
| 2008/0033522 A1 * | 2/2008 | Grewe et al. | 623/1.11 |
| 2008/0039845 A1 * | 2/2008 | Bonutti | A61B 17/0401 606/62 |
| 2008/0169582 A1 * | 7/2008 | Dave et al. | 264/239 |
| 2008/0228186 A1 | 9/2008 | Gall et al. | |
| 2008/0255560 A1 * | 10/2008 | Myers et al. | 606/63 |
| 2008/0269745 A1 | 10/2008 | Justin | |
| 2008/0269746 A1 | 10/2008 | Justin | |
| 2008/0269747 A1 | 10/2008 | Justin | |
| 2008/0269748 A1 | 10/2008 | Justin et al. | |
| 2008/0269749 A1 | 10/2008 | Shalaby et al. | |
| 2008/0269750 A1 | 10/2008 | Justin | |
| 2008/0269776 A1 | 10/2008 | Justin et al. | |
| 2009/0005782 A1 * | 1/2009 | Chirico et al. | 606/63 |
| 2010/0262069 A1 | 10/2010 | Rabiner et al. | |
| 2011/0046746 A1 | 2/2011 | Rabiner et al. | |
| 2011/0118740 A1 | 5/2011 | Rabiner et al. | |
| 2011/0313356 A1 | 12/2011 | Rabiner et al. | |
| 2012/0239037 A1 | 9/2012 | Justin | |

FOREIGN PATENT DOCUMENTS

| | | |
|---|---|---|
| WO | WO 00/12832 | 3/2000 |
| WO | WO 03/065913 | 8/2003 |
| WO | WO 2005/112804 | 12/2005 |
| WO | WO 2008/134287 A2 | 11/2008 |
| WO | WO 2008/134287 A3 | 11/2008 |

* cited by examiner

A-A

B-B

C-C

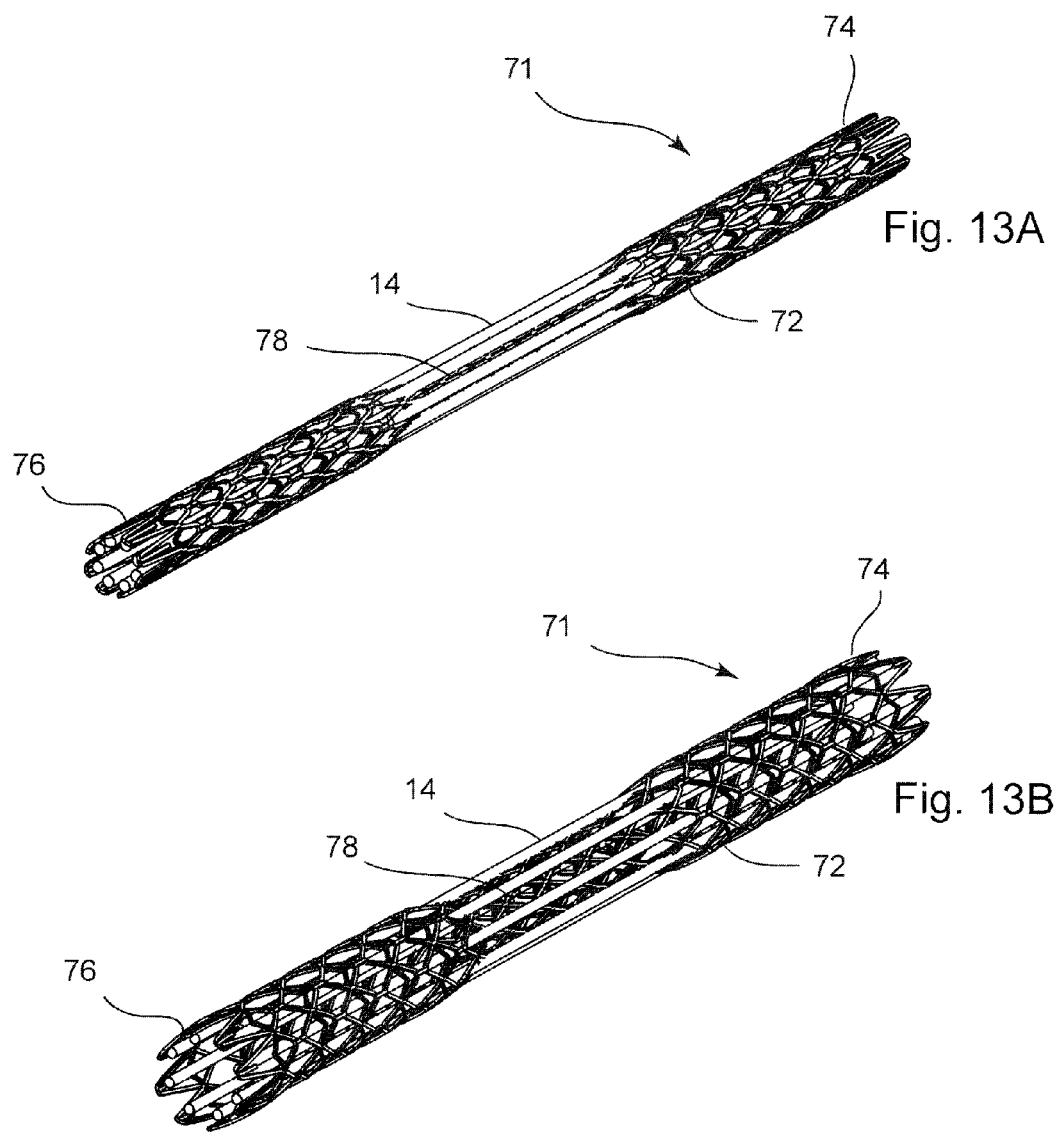

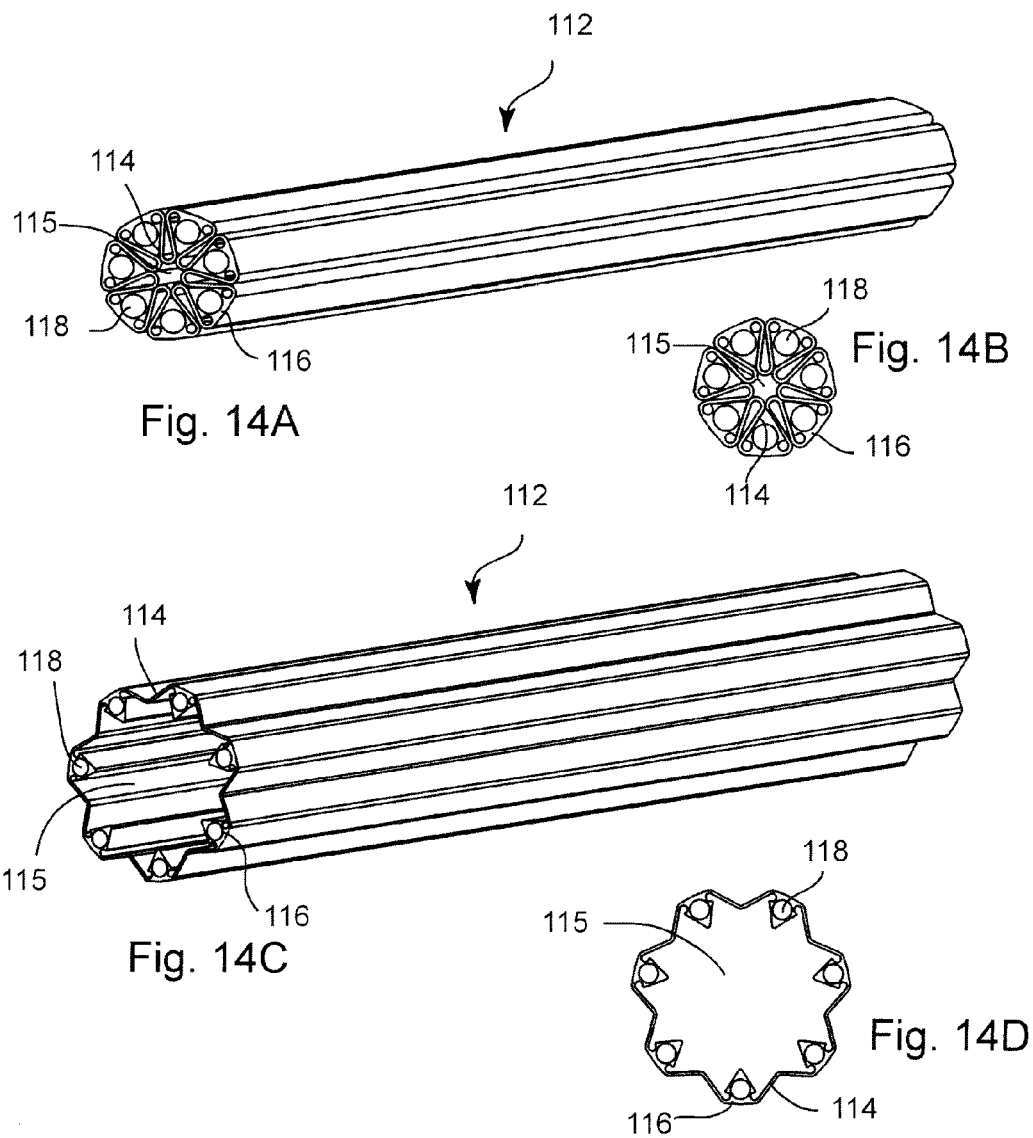

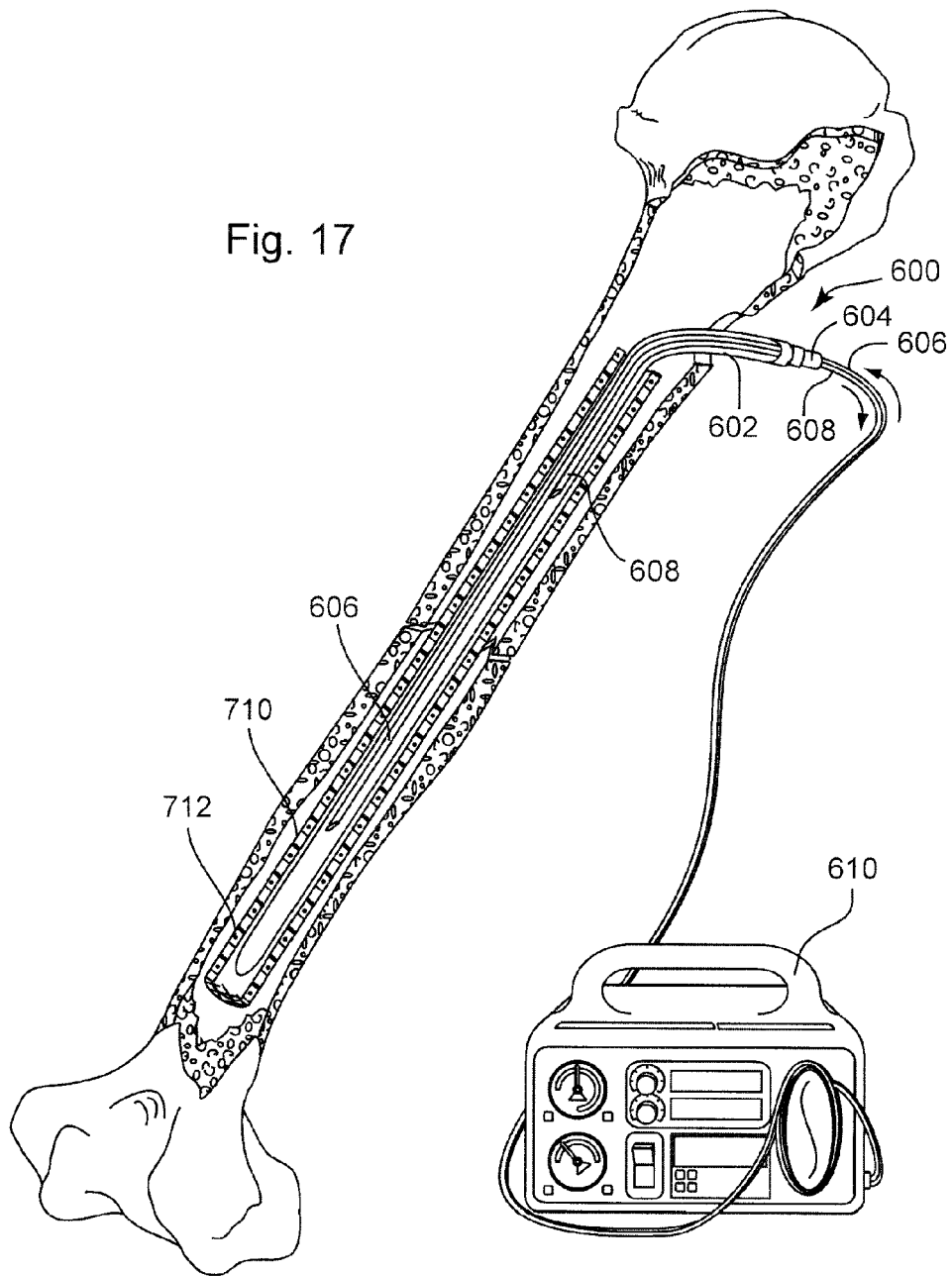

A-A

B-B

C-C

B-B

BONE STABILIZATION DEVICE AND METHOD

CROSS-REFERENCE TO RELATED APPLICATIONS

This application is a continuation of U.S. application Ser. No. 13/423,914, filed Mar. 19, 2012, Entitled BONE STABILIZATION DEVICE AND METHOD, which is a continuation of U.S. application Ser. No. 12/027,521, now U.S. Pat. No. 8,167,881, filed Feb. 7, 2008, entitled IMPLANTABLE COMPOSITE APPARATUS, which is a continuation in part of U.S. patent application Ser. No. 11/777,846, filed Jul. 13, 2007, entitled THERMO-CHEMICALLY ACTIVATED INTRAMEDULLARY BONE STENT; and U.S. patent application Ser. No. 11/777,872, filed Jul. 13, 2007, entitled CONFORMABLE INTRAMEDULLARY IMPLANT WITH NESTABLE COMPONENTS; and U.S. patent application Ser. No. 11/777,892, now U.S. Pat. No. 8,128,626, filed Jul. 13, 2007, entitled SYSTEM AND METHOD FOR DELIVERY, CONFORMATION AND REMOVAL OF INTRAMEDULLARY BONE FIXATION DEVICES; each of which claims the benefit of U.S. Provisional Patent Application No. 60/913,696, filed Apr. 24, 2007 entitled THERMOCHEMICALLY ACTIVATED INTRAMEDULLARY BONE STENT; all of these patent applications being incorporated herein by reference.

BACKGROUND OF THE INVENTION

1. The Field of the Invention

The present invention relates generally to orthopedic devices for the surgical treatment of bone and, more particularly, to the stabilization of bones with an intramedullary device.

2. The Relevant Technology

Orthopedic medicine provides a wide array of implants that can be attached to bone to repair fractures. External fixation involves the attachment of a device that protrudes out of the skin, and therefore carries significant risk of infection. May fractures in long bones can be repaired through the use of bone plates, which are implanted and attached to lie directly on the bone surface. The bone plate then remains in the body long enough to allow the fractured bone to heal properly. Unfortunately, such bone plates often require the surgical exposure of substantially the entire length of bone to which the plate is to be attached. Such exposure typically results in a lengthy and painful healing process, which must often be repeated when the implantation site is again exposed to allow removal of the plate. There is a need in the art for implants and related instruments that do not require such broad exposure of the fractured bone, while minimizing the probability of infection by avoiding elements that must protrude through the skin as the bone heals.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. The drawings may not be to scale.

FIG. 13A is a perspective view of a support structure in a contracted state according to one alternative embodiment of the invention;

FIG. 13B is a perspective view of the support structure of FIG. 13A in an expanded state;

FIG. 14A is a perspective view of a cage in a contracted state;

FIG. 14B is an end view of the cage of 14A in a contracted state;

FIG. 14C is a perspective view of a cage in an expanded state;

FIG. 14D is an end view of the cage of 14C in an expanded state;

FIG. 17 is a longitudinal cross-sectional view of a bone with an intramedullary bone fixation device in a contracted state and a balloon expansion apparatus in the intramedullary canal of the bone, and a regulator apparatus;

DETAILED DESCRIPTION OF THE PREFERRED EMBODIMENTS

Figure 1:
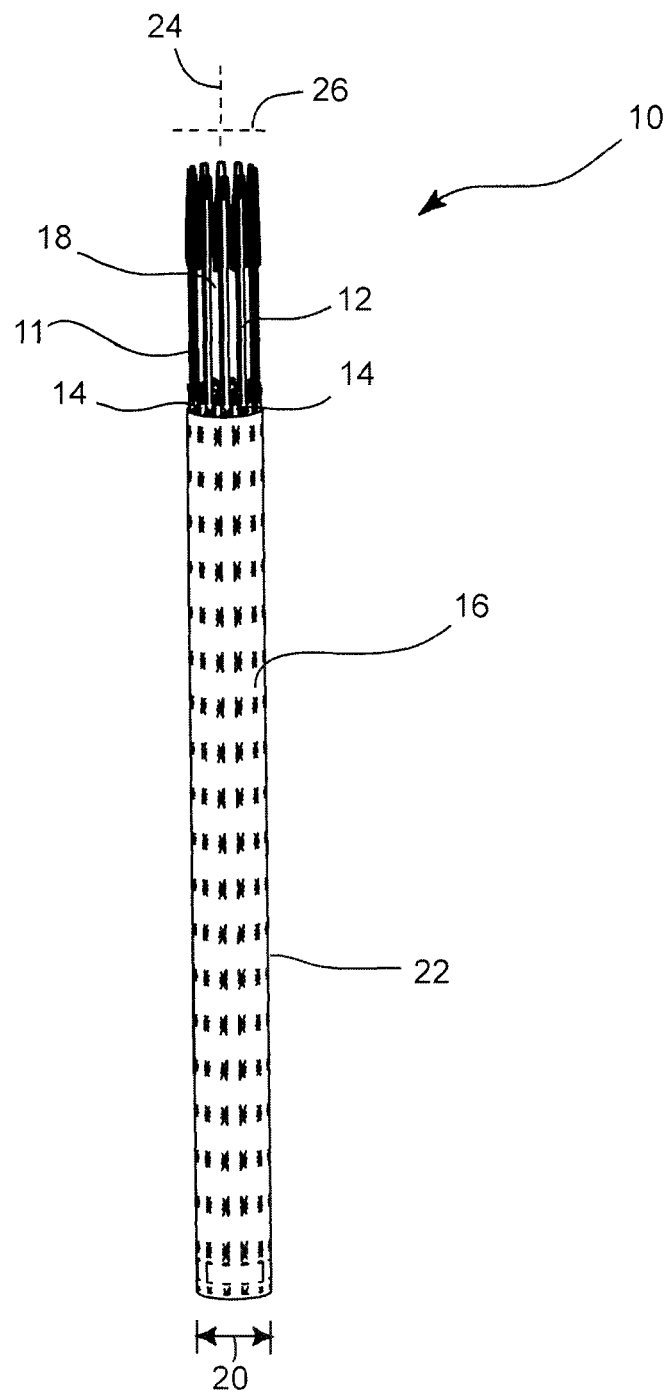
FIG. 1 is a perspective view of an intramedullary bone fixation device according to one embodiment of the invention, comprising a support structure which includes a cage and a plurality of rods, and a thermo-chemically activated thermoplastic matrix.

Referring to FIG. 1, a perspective view illustrates an embodiment of an intramedullary bone fixation composite device 10, where composite is defined as at least two non-identical materials deliberately combined to form a heterogeneous structure with desired or intended properties. The composite device 10 comprises a support structure 11 and a thermo-chemically activated thermoplastic matrix 16. The support structure 11 comprises a cage 12, and at least one stiffening rod 14. The composite device 10 is generally tubular in form and has a longitudinal axis 24 and a transverse axis 26. A hollow central core 18 extends the length of the device 10, surrounded by the cage 12 and rods 14, which are embedded in the thermoplastic matrix 16. An outer perimeter 22 bounds the outer surface of the composite device 10. The composite device 10 is an implant which is able to transition from a contracted and flexible state for introduction into the intramedullary canal, to an expanded and hardened state providing rigid support and alignment for fixation of the surrounding bone, once implanted and allowed to expand to the perimeter of the canal. The thermoplasticity of the matrix 16 allows the composite device 10 to conform to the shape of the surrounding intramedullary canal at a first state, and harden in its conformed shape at a second state providing torsional, axial, and bending reinforcement of the bone fragments during bone healing. When contracted for insertion (or removal), a diameter 20 along the transverse axis 26 of the device is reduced, and the length along the longitudinal axis 24 of the device may be constant or increased. When expanded within the intramedullary canal, the diameter 20 is increased, and the length may be constant or decreased.

Figure 2:
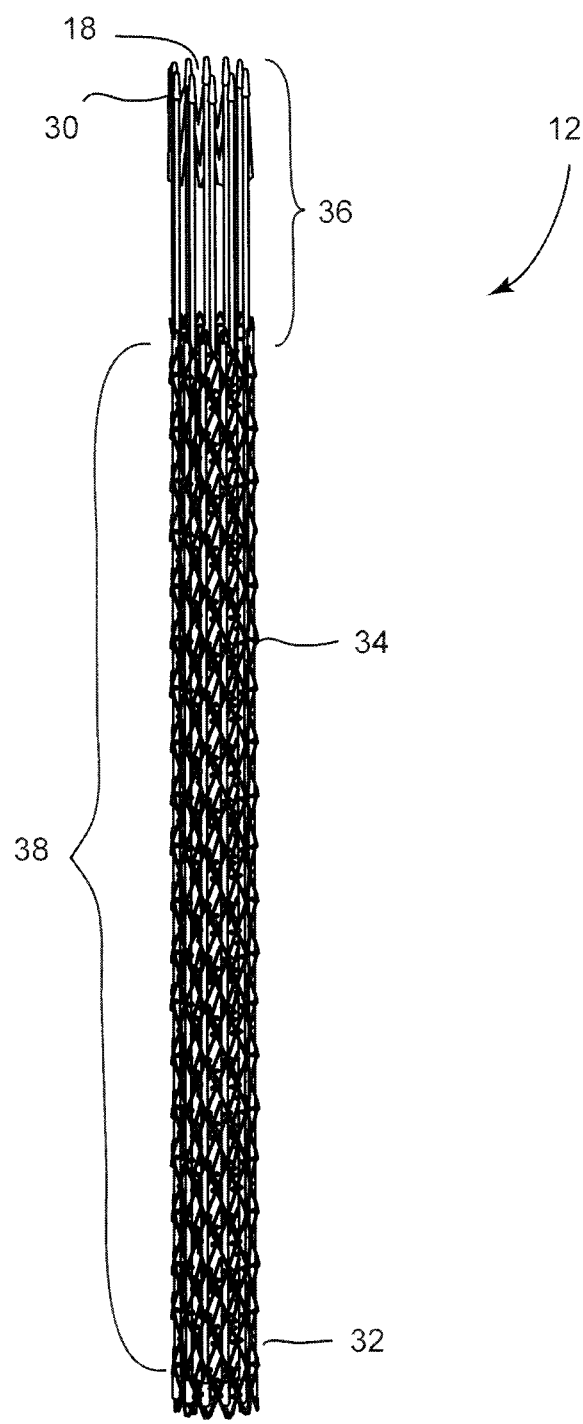
FIG. 2 is a perspective view of the cage of FIG. 1.
Figure 3A:
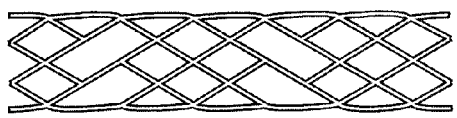
FIGS. 3A-3I are perspective views of various embodiments of stent portions suitable for incorporation into the support structure of FIG. 2.
Figure 3B:
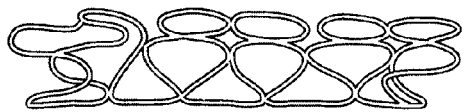
Figure 3C:
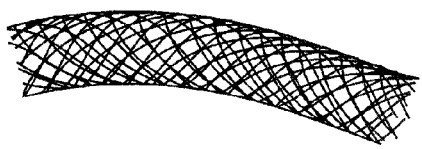
Figure 3D:
Figure 3E:
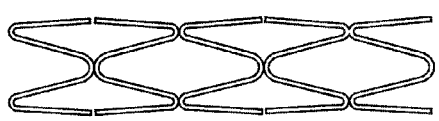
Figure 3F:
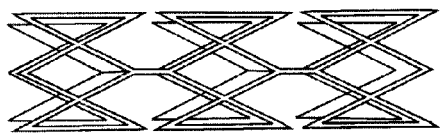
Figure 3G:
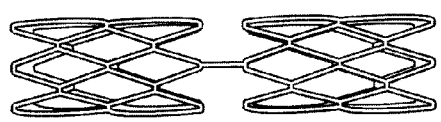
Figure 3H:
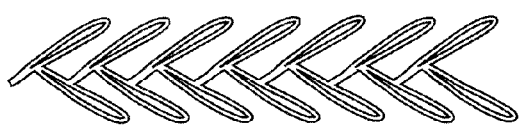
Figure 3I:
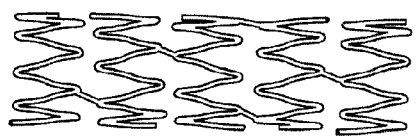

As seen in FIG. 2, the cage 12 is an elongated, generally web-like tube which allows radial expansion and contraction over at least part and preferably all of its length, and bending flexibility as bending loads are applied. The cage 12 has a first end 30, a second end 32 and a sleeve 34 which extends between the ends. The sleeve 34 has an attachment portion 36 and a web-like stent portion 38. The cage is hollow and generally circular in cross-sectional shape, although the web-like construction allows the cross-sectional shape to vary to conform to the contours of the surrounding intramedullary canal. The shape of the intramedullary canal varies along its length, and its cross-sectional shape may be substantially circular, generally triangular or another shape. The cage 12 may comprise a tubular woven or braided cage, a laser cut tubing cage, a machined cage, or a chemically etched tubing cage made from materials such as Nitinol, stainless steel, Co—Cr, Titanium alloys, Tantalum, plastic, polymer, ceramic or other biocompatible materials, among others. In the embodiment depicted, the stent portion 38 comprises a majority of the sleeve 34. However, in other embodiments the stent portion may be a smaller proportion of the sleeve, or comprise the entire sleeve. Attachment portions 36 may be located at one, both, or neither of the ends of the sleeve, or intermittently along the sleeve length.

Referring to FIG. 3, possible configurations of the web-like structure of the stent portion 38 are shown, comprising examples of commercially available stent shapes. These figures show the approximate pattern of the web-like structure. These patterns are adaptable to a variety of lengths, diameters, density of repeatable patterns, wire thicknesses, web areas, and other structural characteristics such that the general stent shape can be configured to a particular bone morphology and size. FIG. 3A is representative of a Johnson and Johnson Palmaz-Schatz™ Version 2 stent. FIG. 3B represents a Medtronic Wiktor™ stent. FIG. 3C represents the general shape of a Schneider "Magic" Wallstent™ stent. FIG. 3D represents a Scimed NIR™ stent. FIG. 3E represents an Arterial Vascular Engineering (AVE™) Microstent. FIG. 3F is representative of a Biotronik Stent™. FIG. 3G is meant to represent the general shape and construct of a Johnson and Johnson Palmaz-Schatz™ stent. FIG. 3H represents a Global Therapeutics Freedom™ stent. FIG. 3I is drawn to represent the adaptable structure of a Scimed Radius™ stent which like all the previously presented representative figures can be configured to the length, diameter and size needed to conform to the intramedullary shape of a particular bone. The stent portion may also be configured with more than one pattern along its length or diameter if needed to better conform to the desired geometry. The stent portion need not be a commercially available stent; it may also have a unique configuration which is constructed from wire, woven, machined, laser cut, or chemically etched.

Figure 4:
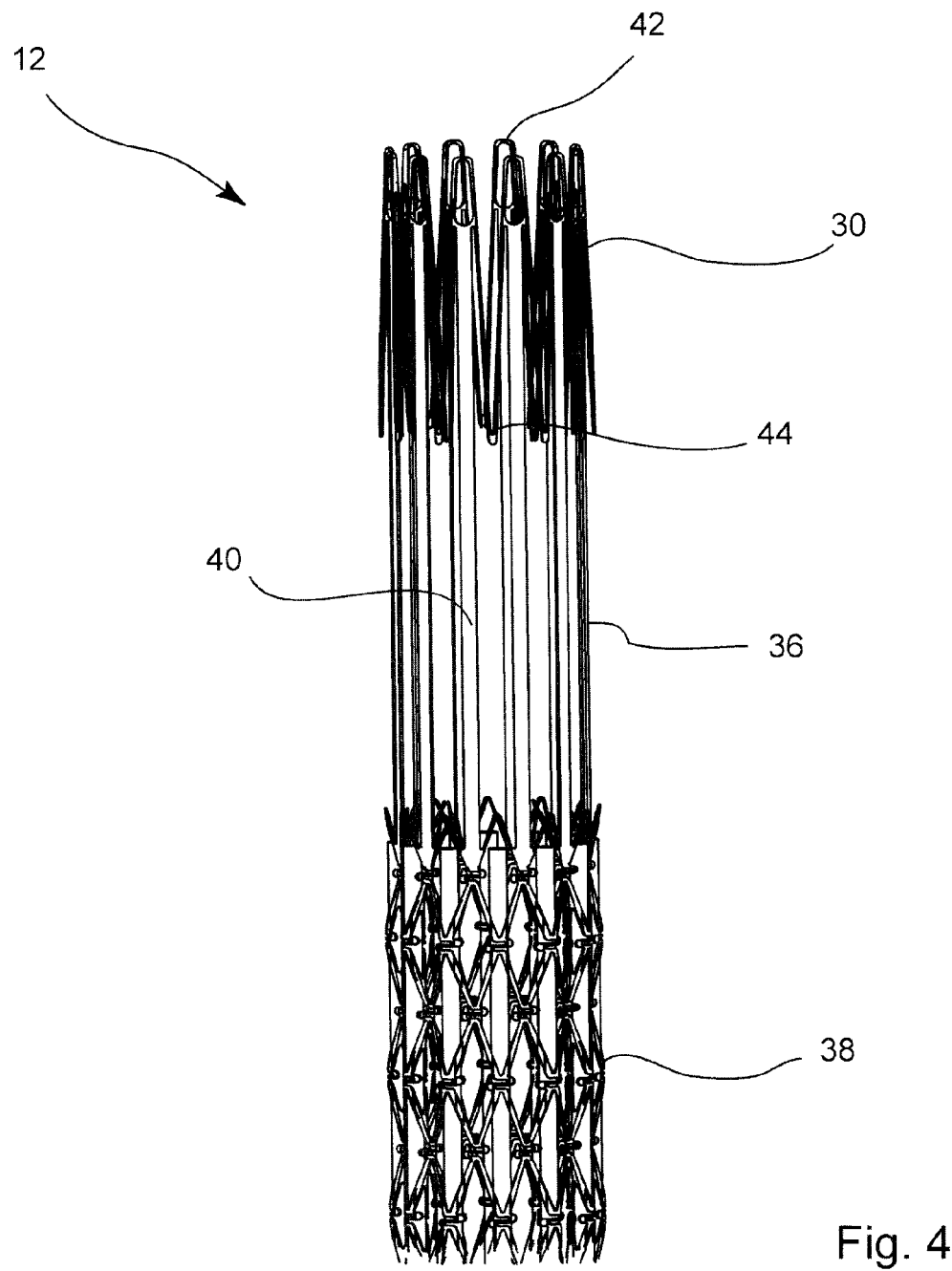
FIG. 4 is an enlarged perspective view of a first end of the cage of FIG. 2.

FIG. 4 is an enlarged view of the first end 30, the attachment portion 36 and part of the stent portion 38 of the cage 12. The attachment portion 36 comprises struts 40 which extend from the stent portion 38 and terminate at loops 42, which allow for the attachment of instruments for device placement, adjustment and removal. Other fasteners such as holes or hooks, among others, may be used instead of loops. Between the struts 40 at the first end 30, linkages 44 connect each strut to the adjacent strut. The linkages allow for radial and longitudinal contraction and expansion of the struts 40 and therefore the first end 30, as the device is contracted and expanded during implantation and removal. The web-like configuration of the stent portion 38 allows for radial and longitudinal contraction and expansion of the remainder of the cage 12.

Figure 5:
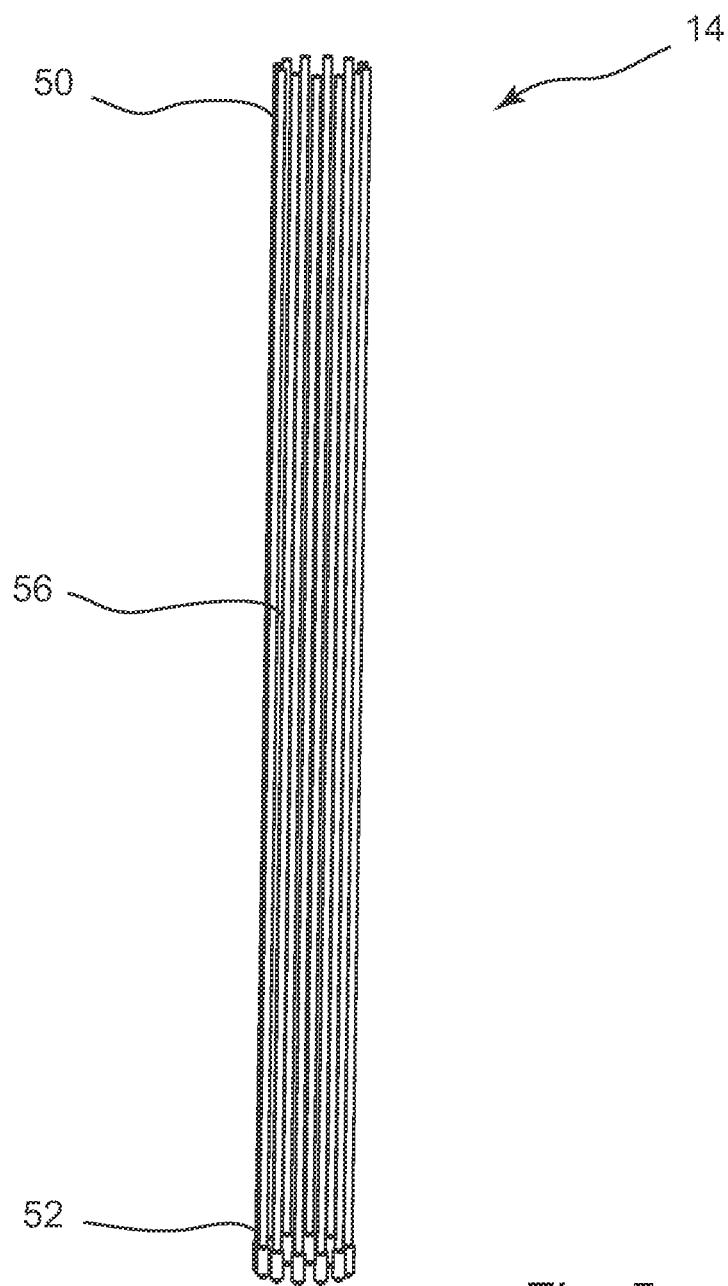
FIG. 5 is a perspective view of the rods of FIG. 1.

Referring to FIG. 5, at least one, and optionally, a plurality, of stiffening rods 14 are oriented parallel to the longitudinal axis of the cage 12 and are contained by the cage in such a way as to allow the stiffening rod(s) to move radially with the cage as the cage contracts and expands. Each rod 14 has a first end 50, a second end 52 and a shaft 56. Each rod 14 may have loops, holes, hooks or other attachment structures at the second end 52 to connect to second end 32 of cage 12. The rods 14 may be threaded loosely or otherwise linked into the stent portion 38 of the cage 12. Holes (not shown) may extend transversely through the rods, and individual webs of the stent portion may pass through the holes to retain the rods. The rods 14 may extend the full length of the cage 12, or preferably from the second end 32 of the cage to the upper end of the stent portion 38. The stiffening rods 14 can be made from any biocompatible material such as stainless steel, cobalt chromium alloys, tantalum, zirconium alloys, titanium or titanium alloys, particularly beta titanium alloys. The stiffening rods 14 can also be made from non-metal biocompatible materials such as PEEK, Acetal, bioabsorbable materials, ceramics and biocomposites. Each stiffening rod 14 is sufficiently flexible to temporarily bend as the device (in a contracted state) is introduced into the intramedullary canal. Additionally, the rods may be knurled, threaded or otherwise treated to provide adhesion and interdigitation of the matrix and cage. Once the device 10 is inserted and expanded radially, the rods 14 are aligned parallel to the longitudinal axis of the bone and line the inner surface of the canal, within the cage and matrix of the device.

The ratio of longitudinal contraction to radial expansion of the composite device 10 varies depending upon the configuration of the stent portion of the cage, the length of the linkages, and the length and placement of the rods. Some embodiments have a low ratio, in which a small decrease in the length of the cage results in a large increase in the radial expansion (as measured by change in the core diameter 20). Other embodiments have a 1:1 ratio (a contraction in cage length results in an equal measurement of radial expansion), or a higher ratio, in which a large decrease in longitudinal contraction produces a small increase in radial expansion. The choice of embodiment will depend upon factors such as the length and diameter of the particular bone to be fixed, accessibility to the bone, and severity of the fracture, among others.

Figure 6:
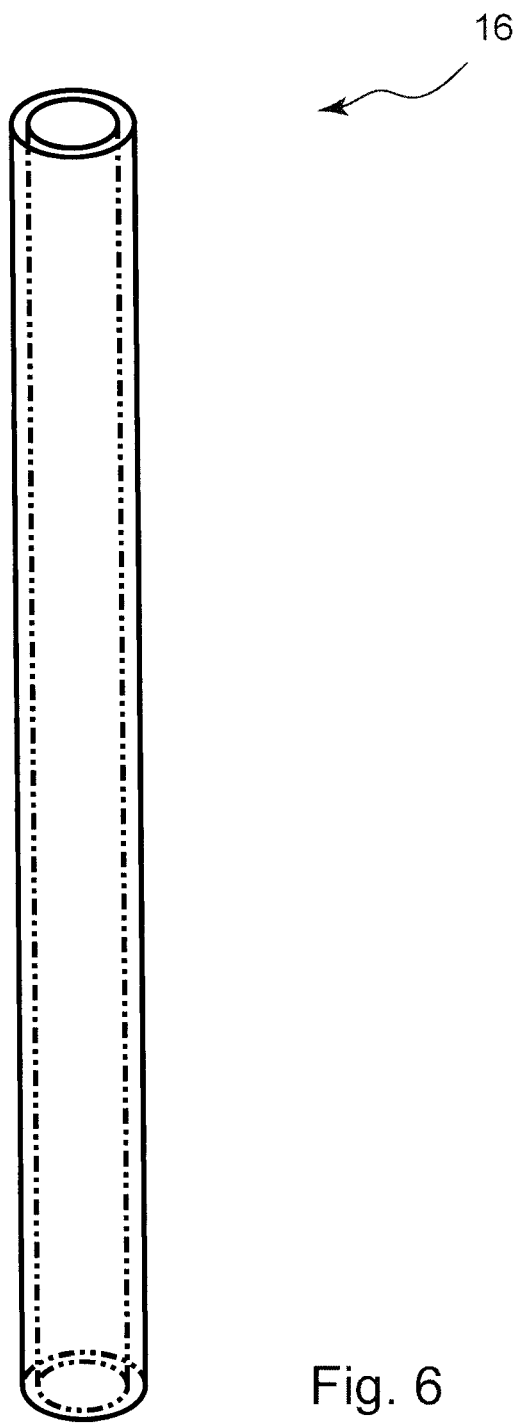
FIG. 6 is a perspective view of the thermoplastic matrix of FIG. 1.

Referring to FIG. 6, the thermoplastic matrix 16 may be thermo-mechanically or thermo-chemically activated, and may surround the support structure 11 of FIG. 2, or the support structure of any of the embodiments described below. The matrix 16 comprises a thermo-chemically activated material which has physical properties that change between a first and second state. For example, the material may be flexible and deformable at a first state and harder and more rigid at a second state. This can be accomplished by changing factors such as the molecular structure of chemical components of the matrix 16 from one state to another. For the purposes of this disclosure, thermo-chemically activated materials are materials which have physical properties which may change between a first state and second state by chemical, thermal, or other processes which change the molecular structure of a material, and thus the physical properties of the material. These processes may include, but are not limited to: changing the temperature of the material, exposing the material to gamma radiation and altering the crosslinking bonds between molecular chains in the material, exposing the material to ultraviolet radiation causing the material to cure and harden, exposing the material to a second material allowing cross-linking and molecular bonding, allowing the material to harden over time by increasing the crystallinity within the molecular structure, and other methods that alter the bonding between the molecules in the material and correspondingly alter its material properties. Within this disclosure, the term thermo-chemically activated may also be referred to as thermoplastic.

The matrix 16 may comprise a thermoplastic biocompatible polymer or polymer blend comprising polymers such as polylactic acid (PLA), poly ε-caprolactone (PCL), trimethylene carbonate (TMC), polyglycolic acid (PGA), poly l-lactic acid (PLLA), poly d-l-lactide (PDLLA), poly-D,L-lactic acid-polyethyleneglycol (PLA-PEG) or other biocompatible polymers. Each of these polymers has a glass transition temperature $T_g$ such that when raised to a temperature above its $T_g$, the polymer is rubbery, flexible and substantially deformable. When lowered to a temperature below its $T_g$, the polymer is crystallized and substantially hardened. Each of these polymers or blends is capable of being transformed by the application of energy to a first thermo-chemical state, in which it is at a temperature above its glass transition temperature $T_g$. When, through dissipation of energy, the temperature is reduced to below $T_g$, the polymer or blend is at a second thermo-chemical state. These thermoplastic properties of the polymers allow them to be repetitively heated to above $T_g$, and subsequently cooled to below $T_g$, moving repeatedly between the first and second thermo-chemical states.

Preferred polymers have a glass transition temperature $T_g$ that is above body temperature, but below the temperature known to cause thermal necrosis of tissues. A preferred blend is crystallized and substantially rigid at human body temperature, and has a $T_g$ which ranges from about 10° C. above body temperature to about 35° C. above body temperature. This acceptable $T_g$ range is between about 50° C. and about 80° C. and preferably between about 55° and about 65° C. Preferably, the thermoplastic matrix 16 comprises a blend of polymers such as PCL and PLA, or PCL and PGA. Table 1 displays the melting points ($T_m$), glass transition temperatures ($T_g$) and thermal decomposition temperatures ($T_{dec}$) of selected synthetic absorbable polymers.

TABLE 1

Melting, glass transition and thermal decomposition temperatures of selected synthetic absorbable polymers.

| Polymer | $T_m$ (° C.) | $T_g$ (° C.) | $T_{dec}$ (° C.) |
|---|---|---|---|
| PGA | 230 | 36 | 260 |
| PLLA | 170 | 56 | 240 |
| PLA | — | 57 | — |
| PCL | 60 | −62 | — |
| Polyglactin910 | 200 | 40 | 250 |
| Polydioxanone | 106 | <20 | 190 |
| Polyglyconate | 213 | <20 | 260 |

Additional biocompatible polymers which may be included in the matrix 16, individually or in a blend, comprise aliphatic polyesters including polyglycolide, poly(dl-lactide), poly(l-lactide), poly(δ-valerolactone), polyhydroxybutyrate; polyanhydrides including poly[bis(p-carboxyphenoxy) propane anhydride], poly(carboxy phenoxyacetic acid), poly(carboxy pheoxyvaleric acid); polyphosphazenes including aryloxyphosphazene polymer and amino acid esters; poly(ortho esters); poly(p-dioxane); poly(amino acids) including poly(glutamic acid-co-glutamate); erodable hydrogels; and natural polymers including collagen (protein) and chitosan (polysaccharide).

The thermoplastic matrix 16 may further include at least one bioactive material to promote growth of bone material and accelerate healing of fractures. These bioactive materials include but are not limited to hydroxylapatite, tetracalcium phosphate, β-tricalcium phosphate, fluorapatite, magnesium whitlockite, β-whitlockite, apatite/wollastonite glass ceramic, calcium phosphate particle reinforced polyethylene, bioactive glasses, bioactive glass ceramics, polycrystalline glass ceramics, and polyethylene hydroxylapatite.

The support structure 11 may be embedded in the thermoplastic matrix 16 through insert molding, pulltrusion, by dipping the support structure into the thermoplastic matrix material while it is at a temperature above $T_g$, or by other coating methods. A variety of different methods may alternatively be used to assemble the thermoplastic matrix 16 and the support structure 11.

Figure 7:
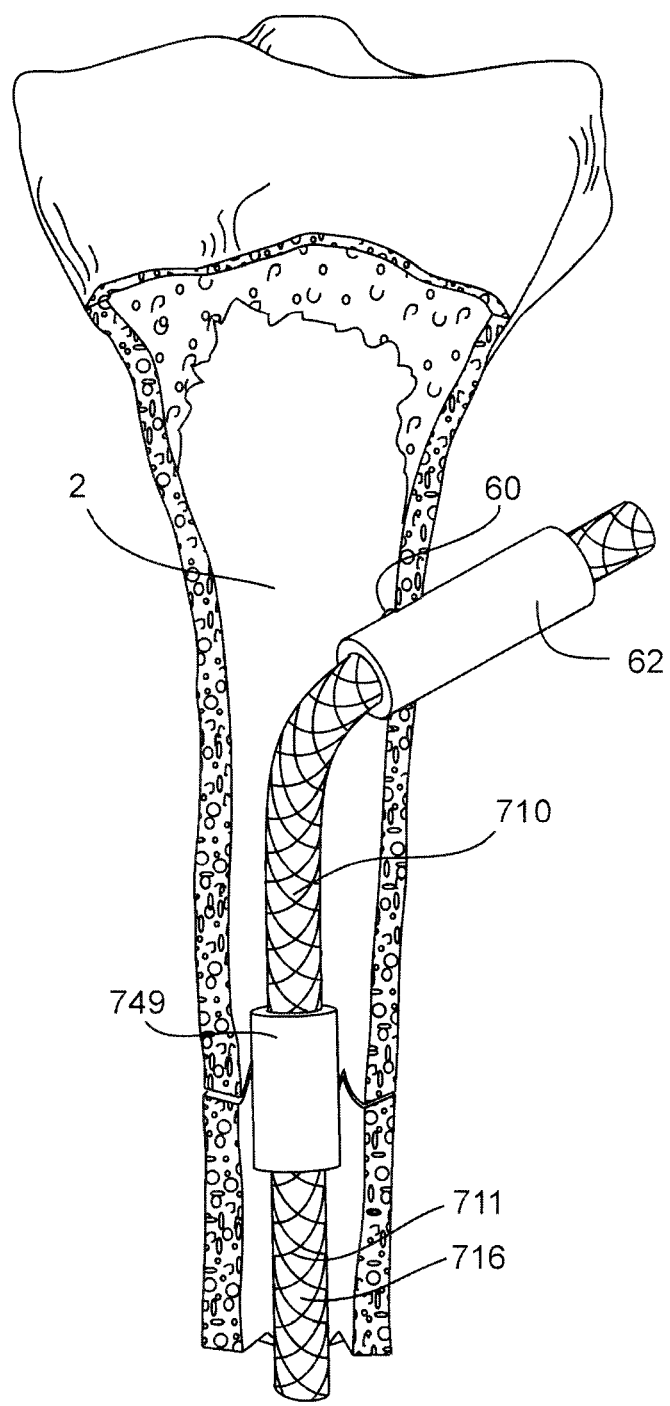
FIG. 7 is a longitudinal cross-sectional view of a bone with an alternative embodiment of an intramedullary bone fixation device partially inserted into the intramedullary canal.

Referring to FIG. 7, a longitudinal cross-section of a bone illustrates implantation of an intramedullary bone fixation composite device 710. The method illustrated in FIG. 7 may also be used for implantation of composite device 10 and other devices according to alternative embodiments. Composite device 710 comprises a support structure 711 and a thermo-chemically activated thermoplastic matrix 716. The support structure 711 comprises a stent-like cage 712 (not shown) and a plurality of rods 714 (not shown).

A percutaneous portal 60 is created into the intramedullary canal 2, preferably in the proximal or distal metaphysical region of the bone. The opening may not be parallel to the longitudinal axis of the bone; it may be transverse or at an acute angle relative to the longitudinal axis of the bone. If necessary to open the canal space and prepare it for the implant, the canal is evacuated using a sequence of pulse lavage, brushing, and suction. A delivery tube 62 may be advanced into the percutaneous portal 60. The composite device 710, in a lengthened and contracted state, is heated immediately prior to implantation to a first thermo-chemical state, so that the thermoplastic matrix 716 is above its glass transition temperature and is therefore substantially deformable and rubbery enough to be flexed as it is introduced through the percutaneous portal and into the intramedullary canal. For the purposes of this disclosure, a structure is "substantially deformable" when it requires significantly less force to deform the structure than when it is "substantially hardened". In the preferred embodiment, a structure is substantially deformable when is requires less than half the force to deform it than would be required in the substantially hardened state.

Heating of the composite device 710 to reach the first thermo-chemical state may be accomplished by means including soaking the implant in a hot saline bath, application of ultrasonic vibratory energy, application of radiant heat energy, use of a local radiation emitter (including ultraviolet, visible light, and/or microwave energy), use of a laser energy emitter, use of inductive heat energy, electrical resistive heating of the cage or the delivery instrument, or heating of an expansion apparatus, among others.

The composite device 710 is inserted into the delivery tube 62, pushed through the tube and advanced into the intramedullary canal 2 until the composite device 710 is contained within the confines of the canal. Optionally, the composite device 710 may be inserted directly through the percutaneous portal 60 without passing through a delivery tube 62. A portion of the composite device 710 may be surrounded by a protective sheath 749, which is positioned so that it covers the device 710 at the point of the bone fracture. The device 710 is then expanded radially. As the support structure 711 expands, the stiffening rods 714, the cage 712 and thermoplastic matrix 716 move radially outward and are eventually aligned along the wall of the intramedullary canal, parallel to the longitudinal axis of the bone. The composite device 710 is allowed to cool to below the low glass transition temperature $T_g$, thus attaining the second thermo-chemical state, and the matrix 716 crystallizes. As the matrix crystallizes it becomes substantially hardened and conforms to the shape of the surrounding intramedullary canal, and the cage 712 and stiffening rods 714 are fixed in the thermoplastic matrix 716 along the wall of the canal. The shape of the intramedullary canal can vary along the length of the bone, with the canal being generally circular in the diaphysial region near the midpoint of the bone and irregular in the metaphysial regions near the ends of the bone. Although the thermoplastic matrix 716 is in a generally tubular shape as the composite device 710 is inserted, the thermoplastic qualities of the matrix allow it to conform to the shape of the intramedullary canal around it, and it crystallizes in that shape, thus providing torsional strength and support to the surrounding bone. The ability of the thermoplastic matrix 716 to conform to the irregularities in the intramedullary canal allows the device 710, and the stabilized bone, to withstand greater torsional forces than would a device with a constant circular shape which did not conform to the canal. For the purposed of this disclosure, "substantially hardened" means the thermoplastic matrix is crystallized and sufficiently hard that it will not change shape when exposed to manual pressure or mechanical pressures.

Deformation and/or radial expansion and of the composite device 710 to conform to the intramedullary canal can be accomplished in several ways. A deformation apparatus (such as those shown in FIGS. 16 and 17) may be introduced into the central core of the composite device 710 before or after it has been inserted into the intramedullary canal. The deformation apparatus is expanded, and forces radial expansion of the composite device 710 until it fills the confines of the canal. The deformation apparatus may comprise a heat source to raise the temperature of the thermoplastic matrix 716. Alternatively, the cage 712 may be constructed with an outward spring bias, introduced into the intramedullary canal and allowed to expand. In another embodiment which is described in detail below, a balloon apparatus (such as that shown in FIG. 17) is introduced into the central core of the composite device 710. As the balloon is inflated with heated gas or liquid, it expands, and consequently induces expansion of the composite device 710. Once the device is expanded, the balloon can be deflated and removed. It is appreciated that these deformation and expansion techniques and apparatuses may also be employed with composite device 10 and other embodiments of intramedullary bone fixation devices disclosed herein.

Figure 8:
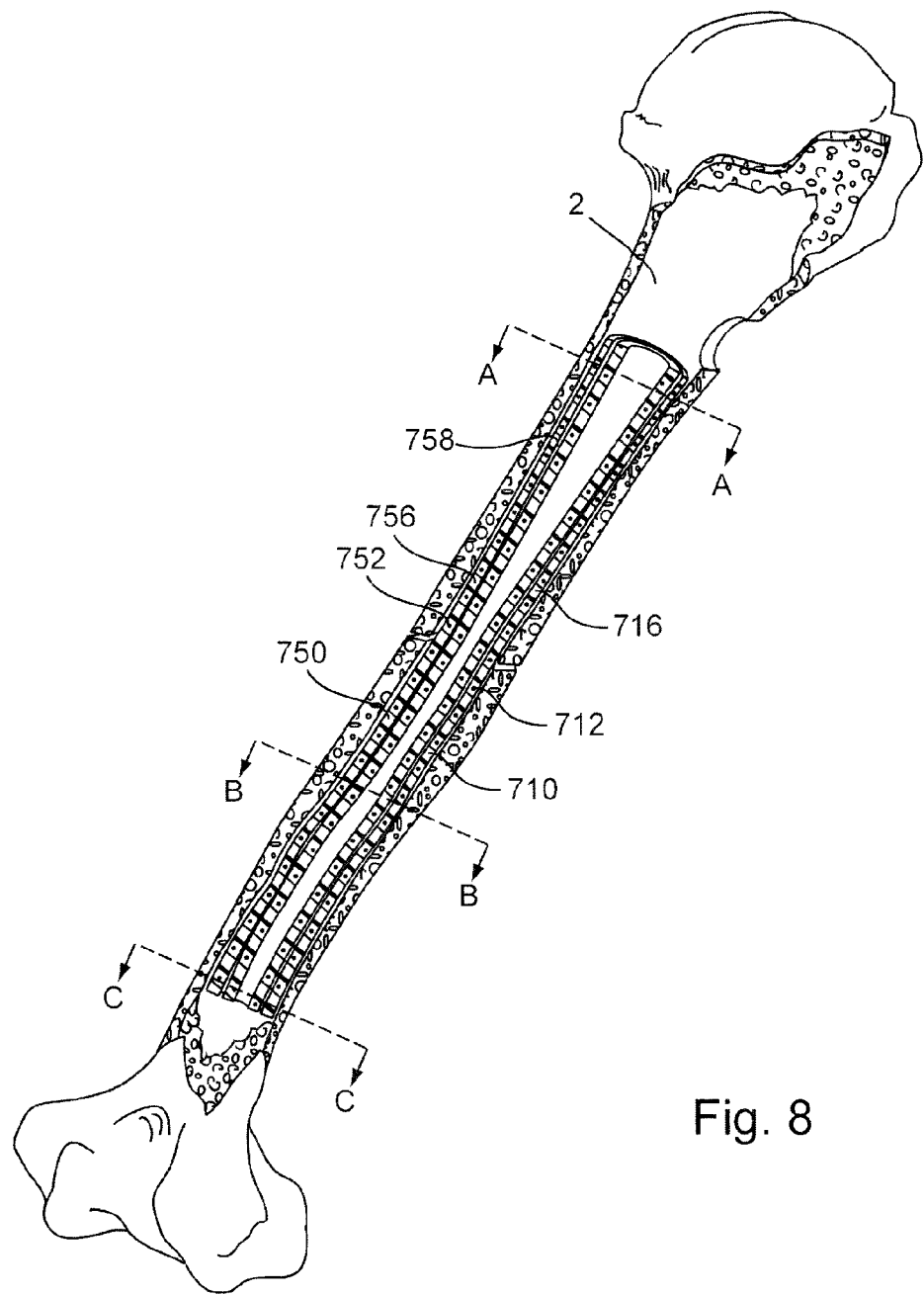
FIG. 8 is a longitudinal cross-sectional view of a bone with the intramedullary bone fixation device of FIG. 7 implanted inside a second intramedullary bone fixation device.

Referring to FIG. 8, a longitudinal cross-section shows two composite devices 710, 750 implanted in a bone. Deploying two bone fixation devices nested in this manner may provide additional strength, rigidity and resistance to torsion than would be available from one bone fixation device. Twice the thermoplastic matrix material and twice the support structure are present to provide additional stabilization.

Composite device 750 comprises a thermoplastic matrix 756, which surrounds a support structure which includes a cage 752 and a plurality of rods 754. The configuration of matrix 756, cage 752 and rods 754 may be identical to that of composite device 710. Prior to implantation, the composite device 750 is partially radially expanded. The composite device 710 is contracted, and slid into a hollow central core 758 of the composite device 750. Together, the two devices 710, 750 are heated until the thermoplastic matrices 716, 756 reach the first thermo-chemical state. The two devices 710, 750 are introduced as a unit into the intramedullary canal. The inner disposed composite device 710 is expanded using one of the techniques previously described. As the inner composite device 710 expands, it pushes radially against the outer disposed composite device 750, forcing it to expand radially until it contacts and conforms to the wall of the surrounding intramedullary canal.

Alternatively, composite devices 710, 750 may be introduced individually into the intramedullary canal. Composite device 750 may be introduced first, heated and expanded. Composite device 710 is then introduced into the hollow central core 758 of composite device 750 after is it in the intramedullary canal. After both devices 710, 750 are in the canal, composite device 710 is heated and expanded, pushing radially against the outer composite device 750.

The thermoplastic matrix 716 surrounding the composite device 710 may contact and conform to the thermoplastic matrix 758 of the composite device 750. The two devices 710, 750 are allowed to cool to the second thermo-chemical state and harden.

Figure 9A:
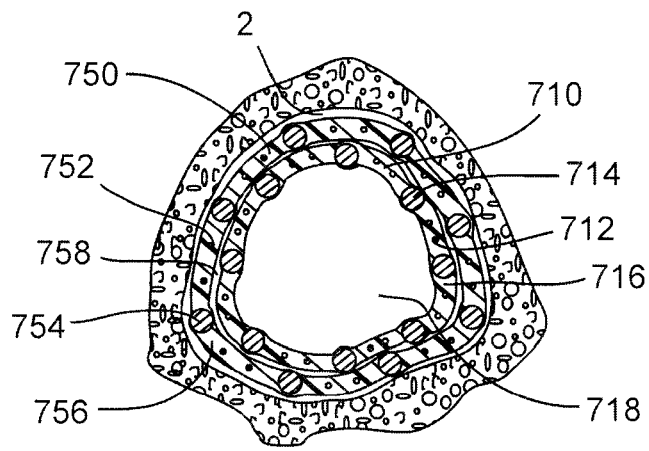
FIG. 9A is an enlarged cross-sectional view of one section of the bone and intramedullary bone fixation devices of FIG. 8.
Figure 9B:
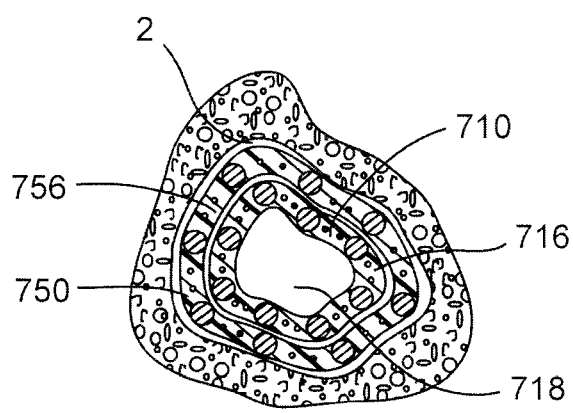
FIG. 9B is an enlarged cross-sectional view of another section of the bone and intramedullary bone fixation devices of FIG. 8.
Figure 9C:
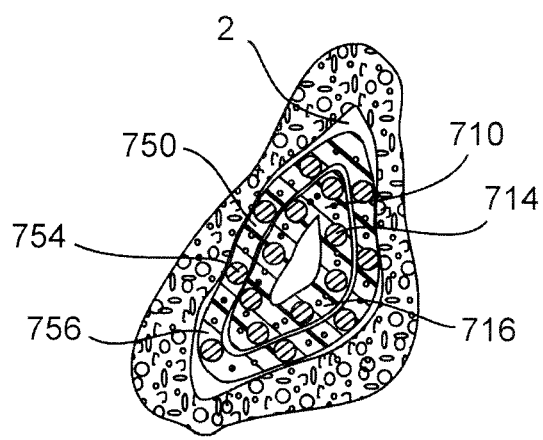
FIG. 9C is an enlarged cross-sectional view of another section of the bone and intramedullary bone fixation devices of FIG. 8.

Referring to FIGS. 9A-9C, three cross-sectional views along different parts of the bone depicted in FIG. 8 are shown, with devices 710, 750 implanted in the intramedullary canal. In FIG. 9A, the intramedullary canal 2 is relatively wide and circular in shape, resulting in a wide, circular central hollow core 718. Also, the thermoplastic matrices 716, 756 are relatively thin, and the rods 714, 754 are spaced relatively far apart, as the devices 710, 750 had to expand radially farther to contact the wall of the intramedullary canal at that point. As seen in FIG. 9B, at this point along the bone the intramedullary canal is smaller in diameter and more irregular in shape. The thermoplasticity of the matrices 716, 756 allows the devices 710, 750 to match the size and shape of the canal. As seen in FIG. 9C, at this point along the bone the intramedullary canal is narrow in cross-section and substantially triangular in shape. According, the thermoplastic matrices 716, 756 are thicker and the rods 714, 754 are closer together, since the devices 710, 750 are relatively less expanded.

Figure 10:
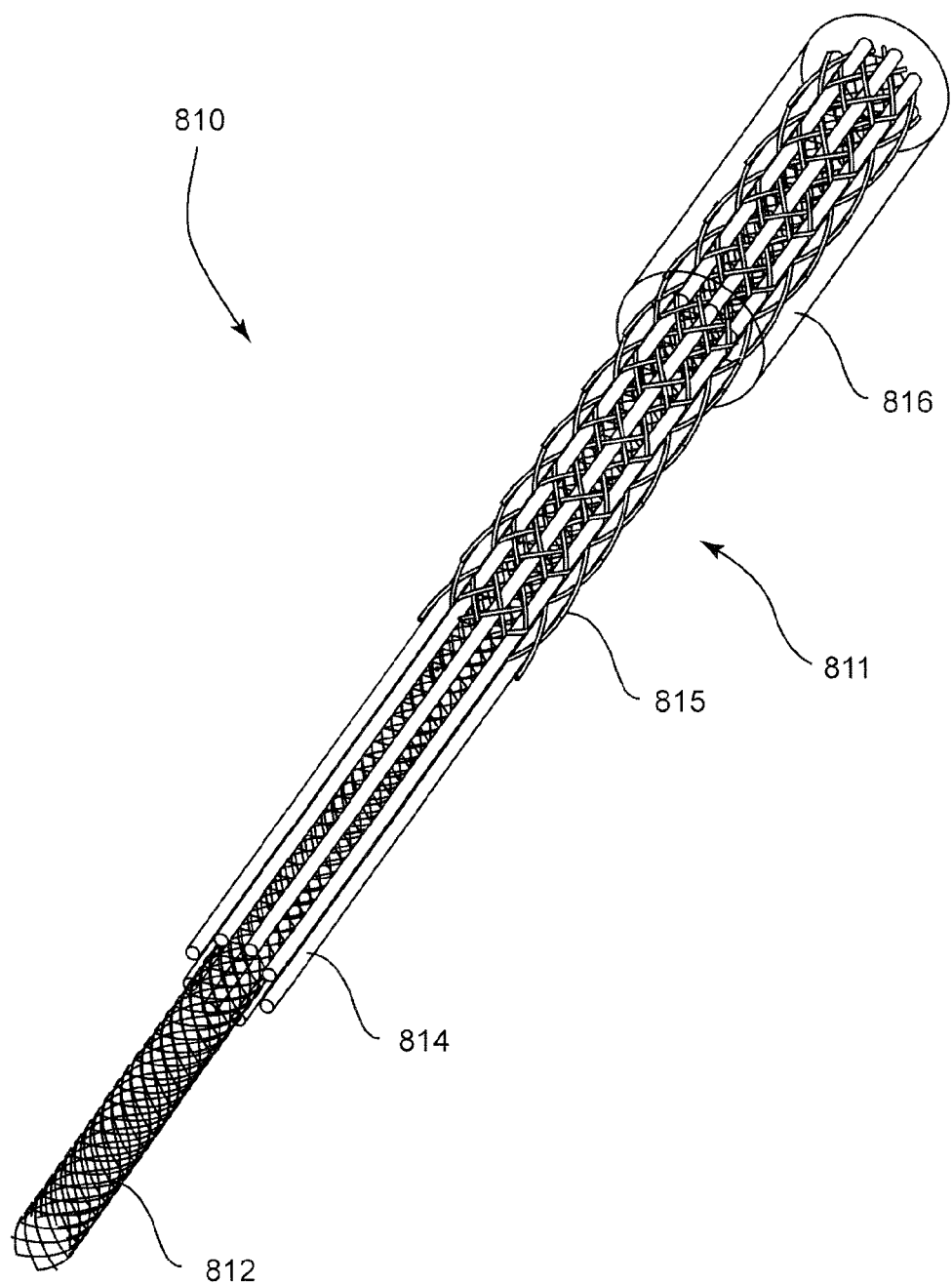
FIG. 10 is a perspective cutaway view of an alternative embodiment of an intramedullary bone fixation device comprising a cage, rods, sutures and a thermoplastic matrix.

Referring to FIG. 10, an alternative embodiment of an intramedullary bone fixation composite device is shown in a cutaway view. Composite device 810 comprises support structure 811 and a thermo-chemically activated thermoplastic matrix 816. Support structure 811 comprises a cage 812, a plurality of rods 814, and a plurality of sutures 815 which connect the cage to the rods. The thermo-chemically activated matrix 816 surrounds the cage 812, rods 814 and sutures 815 such that they are embedded in the matrix. The sutures 815 are interwoven around and between the cage 812 and the rods 814 to connect the cage 812 to the rods 814 in a manner that allows regulated movement of the cage 812 and the rods 814 relative to one another.

Alternately, the sutures may be knit into a sleeve that holds the array of rods and surrounds the cage. The interweaving may be constructed in such a way as to allow radial expansion of the cage 812 and the rods 814 from a contracted position in which the cage 812 is lengthened and the rods 814 are tightly packed together, to an expanded position in which the cage 812 is shortened, radially expanded and the rods 814 are arrayed around the cage with relatively more space between each rod. The cage 812 may comprise web-like stent material similar to stents depicted in FIGS. 3A-3I, or may comprise another woven or laser cut stent-like material. The rods 814 may be similar to the rods 14 depicted in FIG. 5. The thermo-chemically activated thermoplastic matrix 816 may be similar to the thermo-chemically activated thermoplastic matrix 16 described previously and depicted in FIG. 6. The sutures may comprise any of several commercially available sutures, including Dyneema Purity® Ultra High Molecular Weight Polyethylene (UHMWPE), or bioabsorbable multifilament polylactic acid (PLA) sutures such as PANACRL™, among others.

Composite device 810 may be introduced into the intramedullary canal in the same manner as previously described for composite device 710. Energy is applied to composite device 810, heating it until the thermo-chemically activated matrix 816 reaches the first thermo-chemical state, and is flexible and rubbery. The composite device 810 is contracted so that it is sufficiently flexible to be inserted into the intramedullary canal through an opening in the bone, an opening which may not be parallel to the intramedullary canal. The composite device 810 is inserted into the canal and expanded by one of the expansion methods previously described. When the device is expanded within the intramedullary canal, the thermo-chemically activated matrix 816 contacts and is conformed to the walls of the intramedullary canal. The device 810 is allowed to cool and the thermo-chemically activated matrix 816 attains the second thermo-chemical state, and hardens sufficiently to fix the support structure 811 in its expanded position within the intramedullary canal.

Figure 11E:
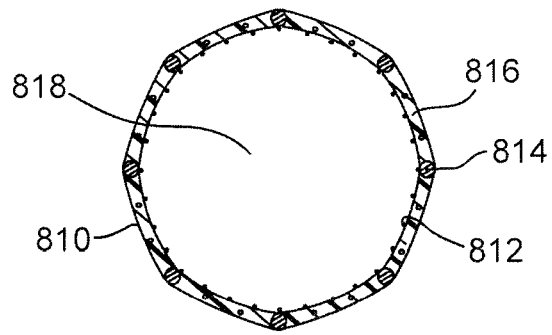
FIGS. 11A-11E are cross-sectional views of the intramedullary bone fixation device of FIG. 10, illustrating radial expansion of the device from a contracted state in FIG. 11A to a fully expanded state in FIG. 11E.
Figure 11D:
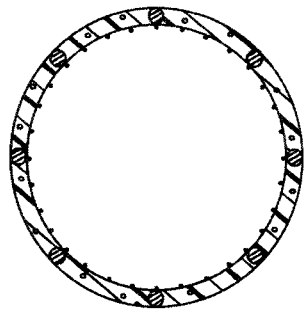
Figure 11C:
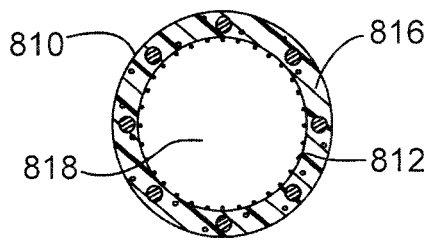
Figure 11B:
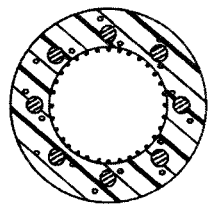
Figure 11A:
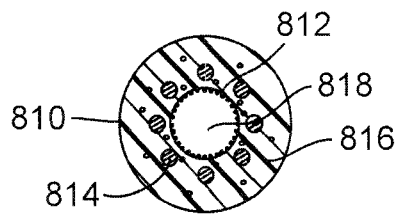

Referring to FIGS. 11A-11E, a series of five cross-sectional views illustrate the expansion of composite device 810 from a contracted position to a fully expanded position. Beginning with FIG. 11A, a hollow central core 818 of composite device 810 is substantially circular. As composite device 810 expands, the cage 812 and the hollow central core 818 increase in diameter and the thermoplastic matrix 816 stretches to fit around the cage 812. At the most expanded state illustrated in FIG. 11E, the thermoplastic matrix 816 is substantially thinner than at the most contracted state. In FIG. 11A, the array of rods 814 are relatively closely packed near one another; in FIG. 11E they are spread apart and are substantially equidistantly arrayed about the hollow central core 818.

Figure 12E:
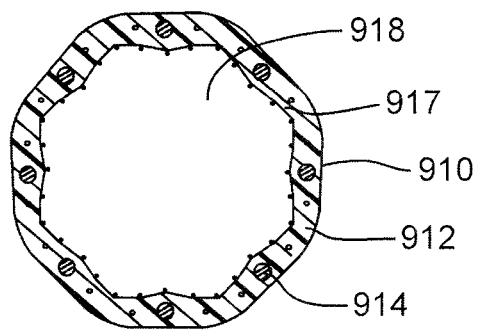
FIGS. 12A-12E are cross-sectional views of an alternative embodiment of an intramedullary bone fixation device, illustrating radial expansion of the device from a contracted state in FIG. 12A to a fully expanded state in FIG. 12E.
Figure 12D:
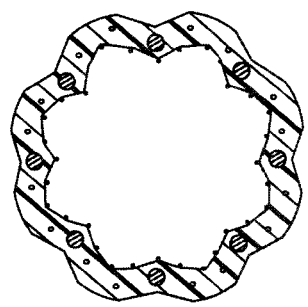
Figure 12C:
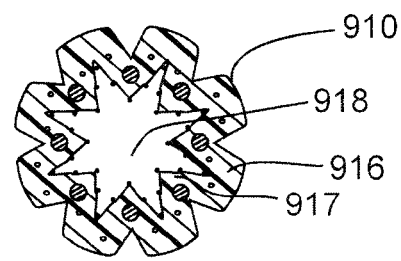
Figure 12B:
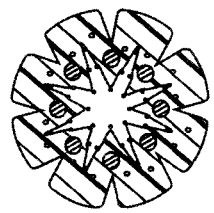
Figure 12A:
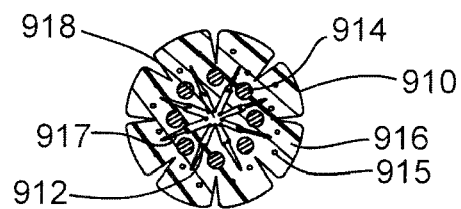

FIGS. 12A-12E illustrate an alternative embodiment of a composite device in five cross-sectional views. Similar to composite device 810, composite device 910 comprises a support structure 911 with a cage 912, a plurality of rods 914, and a plurality of sutures 915 which connect the cage to the rods. A thermo-chemically activated thermoplastic matrix 916 surrounds the cage 912, rods 914 and sutures 915 such that they are embedded in the matrix. As most clearly seen in FIG. 12C, in this embodiment, the thermoplastic matrix 916 is configured in a series of folds 917, as compared to the circular configuration seen for thermoplastic matrix 816 in FIG. 11C. The folded configuration of the thermoplastic matrix 916 results in a star-shaped hollow central core 918. The star-shaped hollow central core 918 is smaller in terms of cross-sectional open space, as much of the space is taken up by the folds of the thermoplastic matrix 916. Therefore, the thermoplastic matrix 916 is thicker in this embodiment than in other embodiments such as device 810. Thus, as seen in FIG. 12E, the fully expanded composite device 910 has a thicker thermoplastic matrix, which may result in additional support for the surrounding bone during the healing process.

Composite device 910 may be introduced into the intramedullary canal in the same manner as previously described for composite devices 710 and 810. Energy is applied to composite device 910, heating it until the thermo-chemically activated matrix 916 reaches the first thermo-chemical state, and is substantially deformable, flexible and rubbery. The composite device 910 is contracted into the deeply folded position seen in FIG. 12A, so that it is sufficiently flexible to be inserted into the intramedullary canal through an opening in the bone. The composite device 910 is inserted into the canal and radially expanded by one of the expansion methods previously described. A specifically configured implant expander such as a star-shaped balloon expansion device (not shown) may be used to expand the device 910. When the device is radially expanded within the intramedullary canal, the thermo-chemically activated matrix 916 contacts and is conformed to the walls of the intramedullary canal. The device 910 is allowed to cool and the thermo-chemically activated matrix 916 attains the second thermo-chemical state, and substantially hardened, fixing the cage 912 and rods 914 in their expanded positions within the intramedullary canal. In the case of a larger bone, two composite devices 910 may be deployed, one inside the other, to provide additional support to the bone.

Referring to FIGS. 13A and 13B, one alternative embodiment of a support structure 71 suitable for use in an intramedullary bone fixation device has an hourglass shape. In the context of the present invention, an hourglass shape is a generally longitudinal, columnar shape in which the two end portions of the column are wider in diameter than a middle portion of the column. The support structure 71 comprises a cage 72 and rods 14. In this embodiment, the diameters of cage ends 74, 76 are greater than the diameter of a cage sleeve 78. In order to clearly view the configuration of cage and rods, a thermoplastic matrix is not shown. A matrix similar to that of the thermoplastic matrix 16 of FIG. 1 may be used in conjunction with support structure 71, or it may have a different configuration. The hourglass shape enables the tubular support structure 71 to conform to the contours of the intramedullary canal of a long bone, in which the metaphysical regions at the ends of the bone are irregular and may be greater in diameter than the diaphysial region near the midpoint of the bone. In the embodiment depicted, the hourglass shape is achieved by the particular threading of the rods within the stent portion of the cage. At the first 74 and second 76 ends, the rods 14 are contained within the confines of the cage 72; toward the center of the sleeve 78, the cage is contained within the circle of the rods 14. In FIG. 13A, the support structure 71 is shown in the contracted state (for insertion or removal); in FIG. 13B, the expanded state is shown. The support structure 71 may be inserted in the same manner as described previous for support structure 11, and the same expansion methods described previously may be used to expand the support structure 71.

One alternative embodiment of an intramedullary bone fixation device (not shown) comprises a laser-cut cage which is constructed with an outward spring bias. In this embodiment, the device is compressed prior to implantation by holding the rods steady and pulling longitudinally on the cage. The web-like configuration of the cage permits the cage to lengthen while simultaneously its core diameter contracts, enabling the device to be narrow and flexible enough for insertion. The device is introduced into the intramedullary canal and the cage is released. Upon release, the outward spring bias of the cage causes the cage to expand radially and simultaneously shorten. Radial expansion continues until the outer perimeter of the device contacts the inner wall of the intramedullary canal. The web-like configuration of the cage also allows it to conform to variations in the geometry of the intramedullary canal. This embodiment may also include the thermoplastic matrix, wherein prior to the compression step described above, the thermoplastic matrix is heated to the substantially deformable first thermo-chemical state, so it is flexible as the device is compressed, inserted and expanded. After insertion and radial expansion, the energy is allowed to dissipate and the thermoplastic matrix attains the substantially hardened second thermo-chemical state.

Referring to FIGS. 14A through 14D, another alternative embodiment of the invention comprises a cage with an outward spring bias, which may be used in conjunction with a thermoplastic matrix such as that depicted in FIGS. 1 and 6. FIG. 14A is a perspective view of a cage 112, cut with a plurality of accordion-type folds 114 which unfold as the cage expands radially. Alternating with the folds 114 are longitudinal ribs 116, and a hollow central core 115 extends the length of the cage 112. Each rib 116 has a longitudinal channel 118 which may hold a stiffening rod. The cage may be laser-cut or machined from metal, or may comprise a plastic material or a thermo-chemically activated thermoplastic matrix material, as described above. The cage 112 may have a straight shape with a constant diameter, or may have an hourglass shape in which the two ends are wider than the central section. Other shapes may alternatively be used for different bone morphologies.

FIG. 14B is an end view of the cage 112 in a compressed state, showing the tight compaction of the folds 114 and ribs 116. FIG. 14C is a perspective view of the cage 112 after radial expansion, and FIG. 14D is an end view of the expanded cage 112. In this embodiment, the support structure can be compressed for implantation by a binding material which is wrapped or tied around the compressed cage. After insertion into the intramedullary canal, the cage is released by cutting or removal of the binding material. Once released, the outward spring bias of the cage 112 causes the cage 112 to expand radially in the same manner as described for the previous embodiment.

Figure 15:
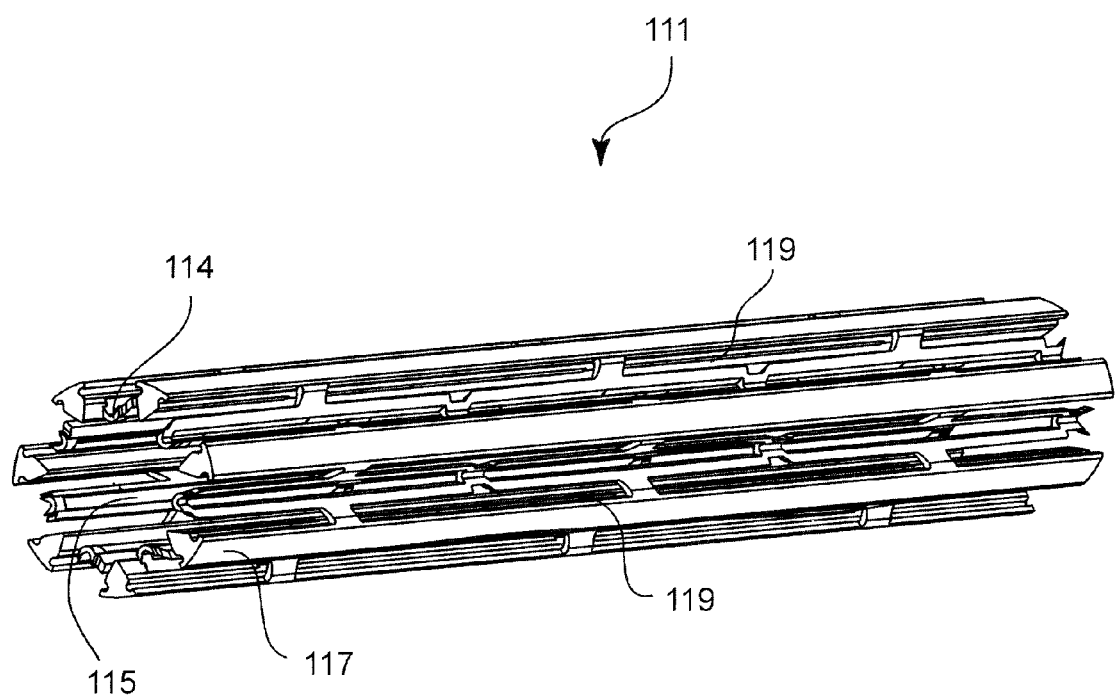
FIG. 15 is a perspective view of a slotted support structure.

In another embodiment the support structure may be monolithic; that is, formed as a single unit. The cage and rods are formed together, such as by a machining process and remain connected together. Referring to FIG. 15, an embodiment of a monolithic support structure 111 is shown in an expanded state. This embodiment has no channels for rods, but consequently has ribs 117 between the accordion folds 114 which are solid and comprise more material, thus providing rigidity similar to the rods of other embodiments. Between the ribs 117, the accordion folds 114 have a plurality of slots 119. The slots 119 allow for less material and thus more flexibility of the support structure when compressed. Additionally, when compressed, the tight packing of the ribs 117 between the accordion folds 114 allows the support structure 111 to flex sufficiently for insertion into the intramedullary canal. The monolithic support structure 111 may be used in conjunction with a thermoplastic matrix. Contraction, insertion and expansion of the monolithic support structure 111 may be in the same manner as described previously for the cage 112.

In another embodiment of the invention, at least two support structures and/or cages such as those depicted in FIGS. 14 and 15 can be nested, one within the other. A first support structure 111 or cage 112 embedded in the thermoplastic matrix 16 is heated to the first thermo-chemical state, compressed, inserted into the intramedullary canal, and expanded. A second support structure 111 or cage 112 embedded in the thermoplastic matrix 16 is similarly compressed and inserted into the central core 115 of the first support structure. When the second structure 111 or cage 112 expands, it pushes radially against the first structure 111 or cage 112. As described previously for other embodiments, the thermoplastic matrix 16 surrounding the first support structure conforms to the contours of the intramedullary canal. Within the first support structure, the thermoplastic matrix 16 surrounding the second support structure conforms to the surrounding first support structure. The matrix material surrounding both the first and second structures cools to the second thermo-chemical state and crystallizes. This double layer of matrix material and support structures provides enhanced support and rigidity to the surrounding bone.

The cage 112 and support structure 111 embodiments depicted in FIGS. 14 and 15 can alternatively be constructed without an outward spring bias. The compressed cage 112 or support structure 111 may be surrounded by the thermoplastic matrix 16. As described previously, the device is heated so the thermo-plastic matrix 16 reaches the first thermo-chemical state and the device is flexed and inserted into the intramedullary canal. In this case, an expansion apparatus or balloon mechanism as previously described, or other expansion mechanism is inserted into the central core 115 and used to expand the device after it is implanted. Once the device is expanded, energy dissipates into the surrounding tissue, the matrix attains the second thermo-chemical state, and the cage 112 or support structure 111 is fixed within the cooled, crystallized matrix 16. The expansion apparatus, balloon mechanism, or other expansion mechanism may then be removed from the central core 115.

One alternative embodiment of an intramedullary bone fixation composite device (not shown) comprises a thermoplastic matrix which is not continuous along the entire length of the corresponding cage or support structure. In this embodiment, the matrix comprises at least two separate tube-like portions, each of which surrounds one end of the cage or support structure and extends partway along the sleeve. This discontinuous configuration of the matrix contributes to an hourglass shape and allows less matrix material to be used. This matrix configuration can be used with either a cage with an outward spring bias, or with a cage with no outward spring bias.

Another alternative embodiment of an intramedullary bone fixation composite device (not shown) comprises a support structure which comprises at least one rod, and no cage. Prior to implantation, the matrix is heated to the first thermo-chemical state and formed into a tubular shape around the rods, which are subsequently embedded in the matrix. The device is flexed and inserted into the patient. While the matrix is still in the first thermo-chemical state, an expansion apparatus or balloon is inserted into the center of the tubular device and used to expand the device within the intramedullary canal. As the device expands, the rods and the matrix material are pushed radially to the inner wall of the intramedullary canal. After expansion, the device is allowed to cool to the second thermo-chemical state, and the matrix hardens, fixing the rods in their positions around the inner wall of the canal.

Another alternative embodiment of an intramedullary bone fixation device (not shown) comprises a support structure which comprises a cage manufactured of the thermoplastic matrix material, and rods. During manufacture the matrix material is heated above its $T_g$ and extruded into a cage-like form. During or after extrusion the rods are interwoven, braided in, or otherwise attached as described previously. To implant the device, the device is heated above the $T_g$ of the matrix to attain the first thermo-chemical state, contracted, flexed, inserted and expanded as described previously.

Figure 16A:
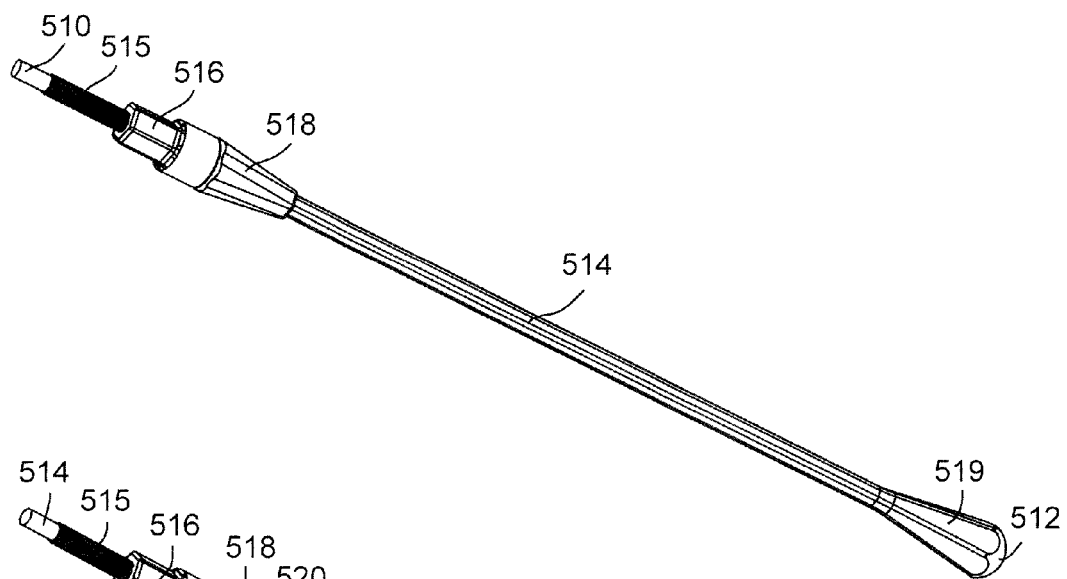
FIG. 16A is a perspective view of a shaft portion of a mechanical expansion apparatus suitable for use with the device of FIG. 1.
Figure 16B:
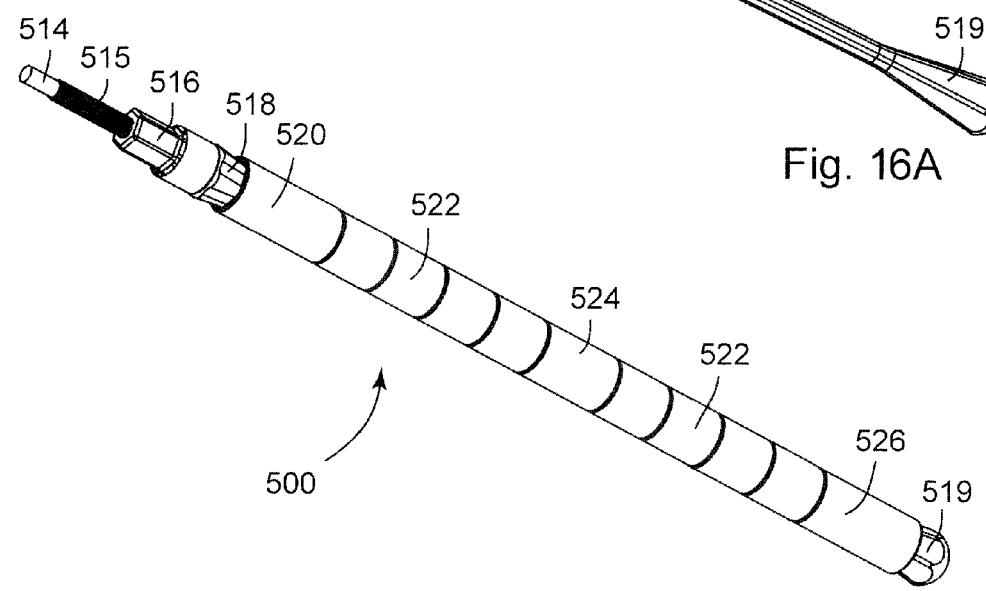
FIG. 16B is a perspective view of the complete mechanical expansion apparatus of FIG. 16A.

FIGS. 16A and 16B illustrate an implant expansion device which may be used to deform and expand several of the intramedullary bone fixation devices described previously, such as composite device 10, composite devices 710, 750 and 810, a device incorporating support structure 71, or other devices which incorporate a cage or support structure without an outward spring bias. A mechanical expansion apparatus 500 is longitudinally insertable into the central core of the intramedullary bone fixation device. As seen in FIG. 16A, the mechanical expansion apparatus 500 has a shaft 514, which extends from a first end 510 to a second end 512. An adjustment nut 516 is threaded onto a threaded portion 515 of the shaft 514, adjacent the first end 510. A cone-shaped first expander guide 518 is also threaded onto the threaded portion 515 of the shaft 514, on the opposite side of the adjustment nut 516 from the first end 510. The second end 512 of the shaft 514 terminates in a cone-shaped second expander guide 519. The shaft 514 comprises a metallic material, and is sufficiently thin and flexible to be inserted into the central core of an intramedullary bone fixation while the device is in the intramedullary canal of a bone in a patient.

Referring to FIG. 16B, strung on the central shaft 514 and listed in their order of occurrence from the first expander guide 518 to the second expander guide 519 are: a first expander segment 520, a plurality of core segments 522, a central segment 524, another plurality of core segments 522, and a second expander segment 526. The core segments 522 and the central segment 524 comprise a relatively rigid material, while the expander segments 520, 526 comprise a relatively rubbery, flexible material. The first expander segment 520 surrounds a portion of the first expander guide 518 in a sleeve-like manner, and the second expander segment 526 similarly surrounds a portion of the second expander guide 519 in a sleeve-like manner. The core segments 522, central segment 524, and expander segments 520, 526 are initially placed loosely on the shaft 514 with space between each segment, so that the apparatus can flex while being inserted into the central core of the intramedullary bone fixation device.

After the intramedullary bone fixation device with a thermoplastic matrix (not shown) is placed in the intramedullary canal, the mechanical expansion apparatus 500 may be inserted through the delivery tube 62 (not shown) into the central core of the intramedullary bone fixation device. Then the adjustment nut 516 is turned, forcing the first expander guide 518 to advance along the shaft 514 toward the second expander guide 519 at the second end 512. The first expander segment 520, core segments 522, central segment 524, and second expander segment 526 are compressed together as they are held between the first and second expander guides 518, 519. The rubbery, flexible expander segments 520, 526 expand radially as they are forced farther onto the cone-shaped expander guides 518, 519. As the expander segments 520, 526 expand radially, they push the ends of the surrounding intramedullary bone fixation device outward radially, thus matching the generally hourglass shape of the intramedullary canal. Expansion is ceased when the outer perimeter of the intramedullary bone fixation device contacts the inner walls of the intramedullary canal. The expansion apparatus 500 may be kept in the central core of the intramedullary bone fixation device until the thermoplastic matrix cools to the second thermo-chemical state. The expansion apparatus 500 is contracted by turning the adjustment nut 516 in the opposite direction, and the apparatus 500 is then removed from the central core.

The expansion apparatus 500 may optionally include a heating element. In this configuration, it can heat the thermoplastic matrix of an intramedullary bone fixation device while in a patient, in order to adjust the conformity of the matrix within the intramedullary canal.

Referring to FIGS. 17-21, an alternative method to deform and expand an intramedullary bone fixation device comprises an implant deformer which is a balloon expansion apparatus. As seen in FIG. 17, a balloon expansion apparatus 600 configured to fit within a composite device 10 in the intramedullary canal of a bone comprises an elastic bladder 602 with an opening 604. A set of flexible hoses comprising an input hose 606 and an output hose 608 are configured to extend from a regulator apparatus 610, through the opening 604 and into the elastic bladder 602. The regulator apparatus 610 is external to the patient, and comprises a pump to regulate flow, and a temperature regulator to regulate the temperature, of liquid which can flow into and out of the elastic bladder 602. FIG. 17 depicts the hoses adjacent and parallel to one another; however they may be configured in alternative arrangements, including a concentric arrangement in which one hose surrounds the other. The hoses 606, 608 terminate at differing positions within the bladder 602.

Figure 18:
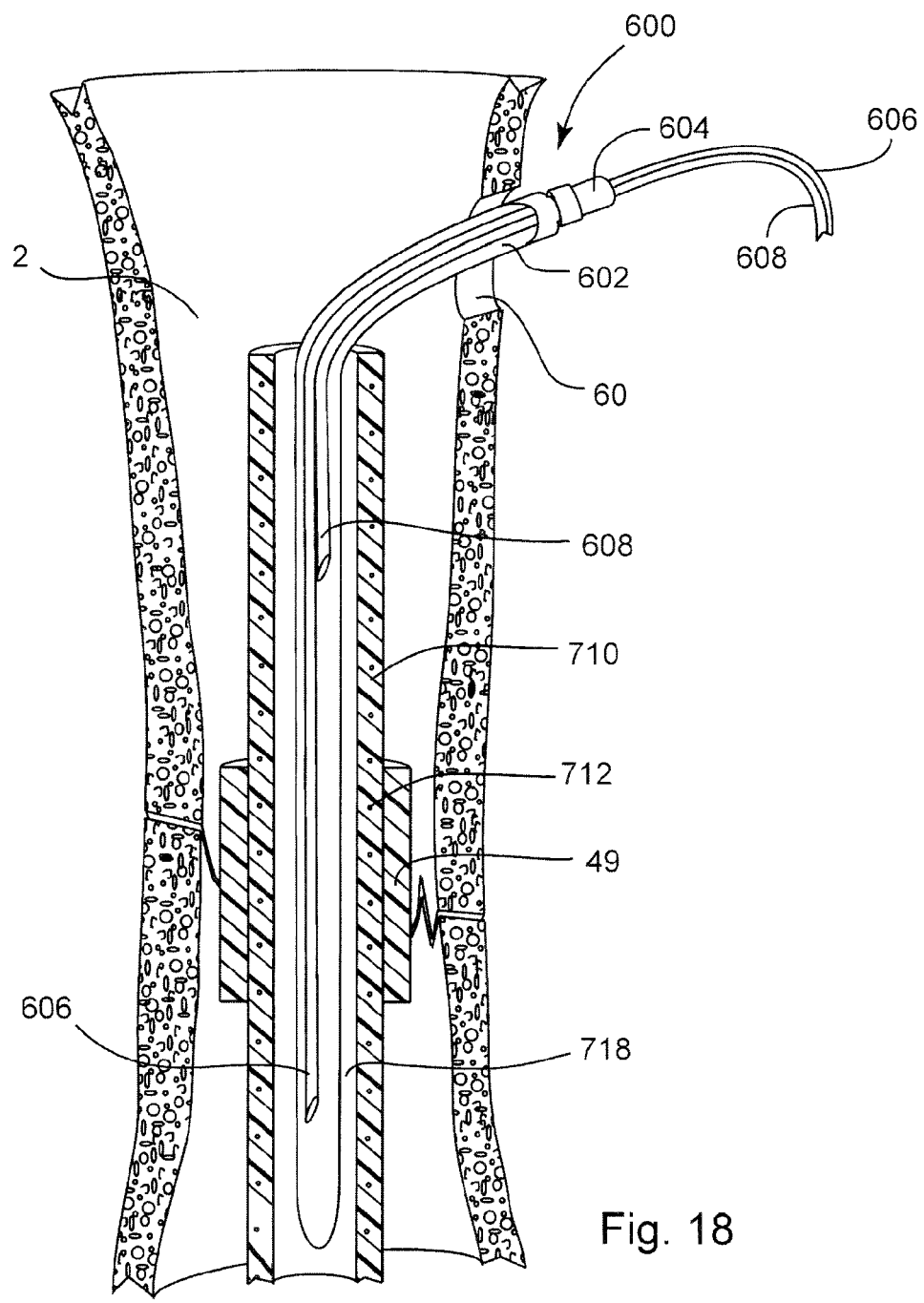
FIG. 18 is a longitudinal cross-sectional view of a portion of the bone of FIG. 17, with the intramedullary bone fixation device in a contracted state and a balloon expansion apparatus of FIG. 17.

Referring to FIG. 18, a composite device 710 with a balloon expansion apparatus 600 already inserted into the central core 718 is introduced into the intramedullary canal of a bone. Introduction into the bone can be through the method described previously, in which the composite device (with the balloon apparatus in the central core) is heated so that the matrix attains the first thermo-chemical state. The composite device 710 plus balloon apparatus 600 are flexed and introduced into the intramedullary canal through the percutaneous portal 60. A delivery tube 62 (not shown) may optionally be used during the introduction and expansion procedures. The input 606 and output 608 hoses are inserted through the balloon opening 604 ideally before the composite device 710 plus balloon apparatus 600 are introduced into the intramedullary canal, but can optionally be inserted into the balloon opening 604 after introduction into the intramedullary canal. A protective sheath 49 may surround the composite device 710 at the location of the bone fracture.

Figure 19:
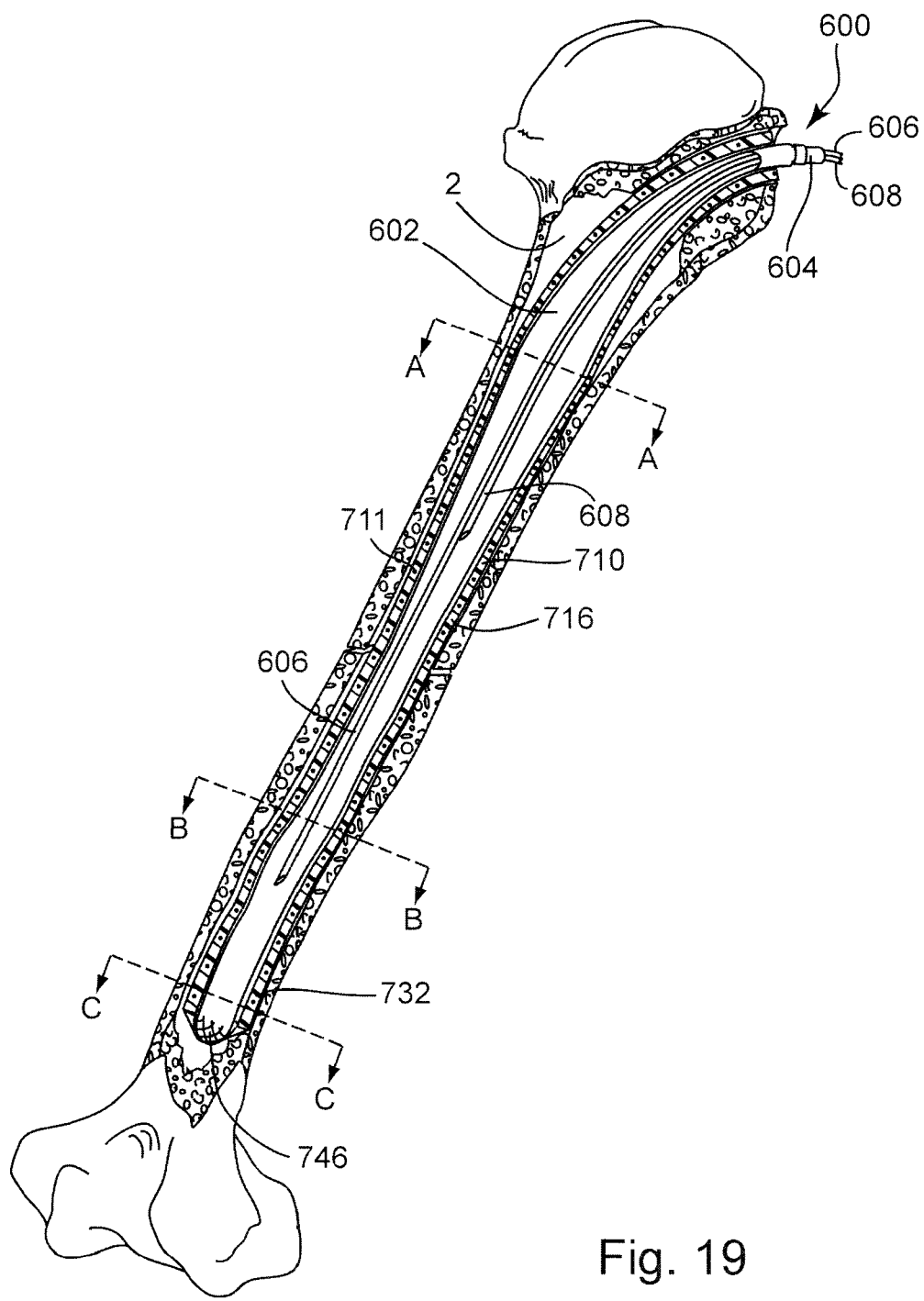
FIG. 19 is a longitudinal cross-sectional view of the bone, intramedullary bone fixation device and balloon expansion apparatus of FIG. 17, with the balloon in an inflated state and the intramedullary bone fixation device in an expanded state.

Referring to FIG. 19, after the composite device 10 plus balloon apparatus 600 are within the intramedullary canal, inflation of the bladder 602 may begin. The external regulator apparatus 610 (not shown) pumps heated liquid such as water or saline solution, among others, through the input hose 606 into the elastic bladder 602. The heat of the liquid maintains the thermoplastic matrix 716 of the composite device 710 at the deformable first thermo-chemical state. As the heated liquid fills the bladder 602, the bladder expands. Contained within the composite device 710, the bladder 602 eventually pushes outward, inducing radial expansion of the composite device 710. As described previously, cage and rod components of the support structure 711 are connected in a web-like construction which allows them to expand radially. The thermoplastic matrix 716 surrounding the support structure 711 is at the heated first thermo-chemical state and is pushed radially by the expanding support structure, conforming to the surrounding intramedullary canal walls. The flexible, rubbery character of the matrix allows it to fit into the natural morphological variations in the wall of the intramedullary canal. A mesh-like end cap 746 on a second end 732 of the composite device 710 prevents the elastic bladder 602 from escaping or ballooning out of the second end 732. The output hose 608, which terminates at a location different from that of the input hose 606, allows liquid to flow out of the balloon apparatus 600. The regulator apparatus 610 maintains the flow, temperature and pressure of the liquid.

Figure 20A:
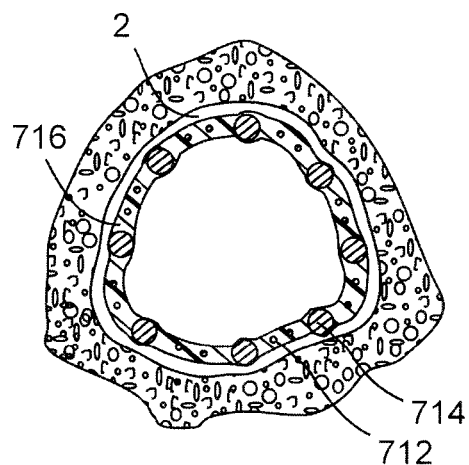
FIG. 20A is an enlarged cross-sectional view of one section of the bone and intramedullary bone fixation device of FIG. 19.
Figure 20B:
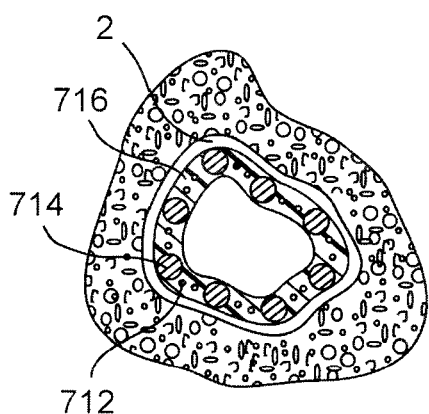
FIG. 20B is an enlarged cross-sectional view of another section of the bone and intramedullary bone fixation device of FIG. 19.
Figure 20C:
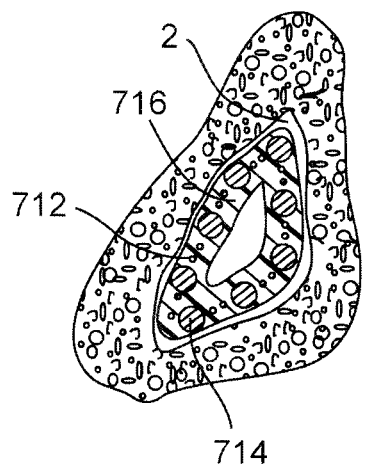
FIG. 20C is an enlarged cross-sectional view of another section of the bone and intramedullary bone fixation device of FIG. 19.

FIGS. 20A-20C display cross-sections of the bone and the composite device 710 at three different locations along the length of the bone shown in FIG. 19. At cross-section A-A in FIG. 20A, the cross-sectional shape of the intramedullary canal is relatively circular. The device 710 has expanded to the wall of the canal, the matrix 716 is relatively thin, and the rods 714 are spaced relatively far apart. At cross-section B-B in FIG. 20B, the canal is smaller and more rectangular in shape than at cross-section A-A. However, the deformable nature of the matrix 716 allows the matrix and the entire composite device 710 to expand differentially and conform to this variation in shape of the intramedullary canal. At cross-section C-C in FIG. 20C, the cross-sectional shape of the intramedullary canal is relatively smaller, and has a triangle-like shape. Again, the matrix 716 and the composite device 710 can conform to this irregular shape. The rods 714 are relatively closer together and the matrix 716 is relatively thicker. The ability of the composite device 710 to closely conform to the confines of the intramedullary canal allows the device to withstand greater torsional forces than would a device with a constant circular shape which did not conform to the canal.

Figure 21:
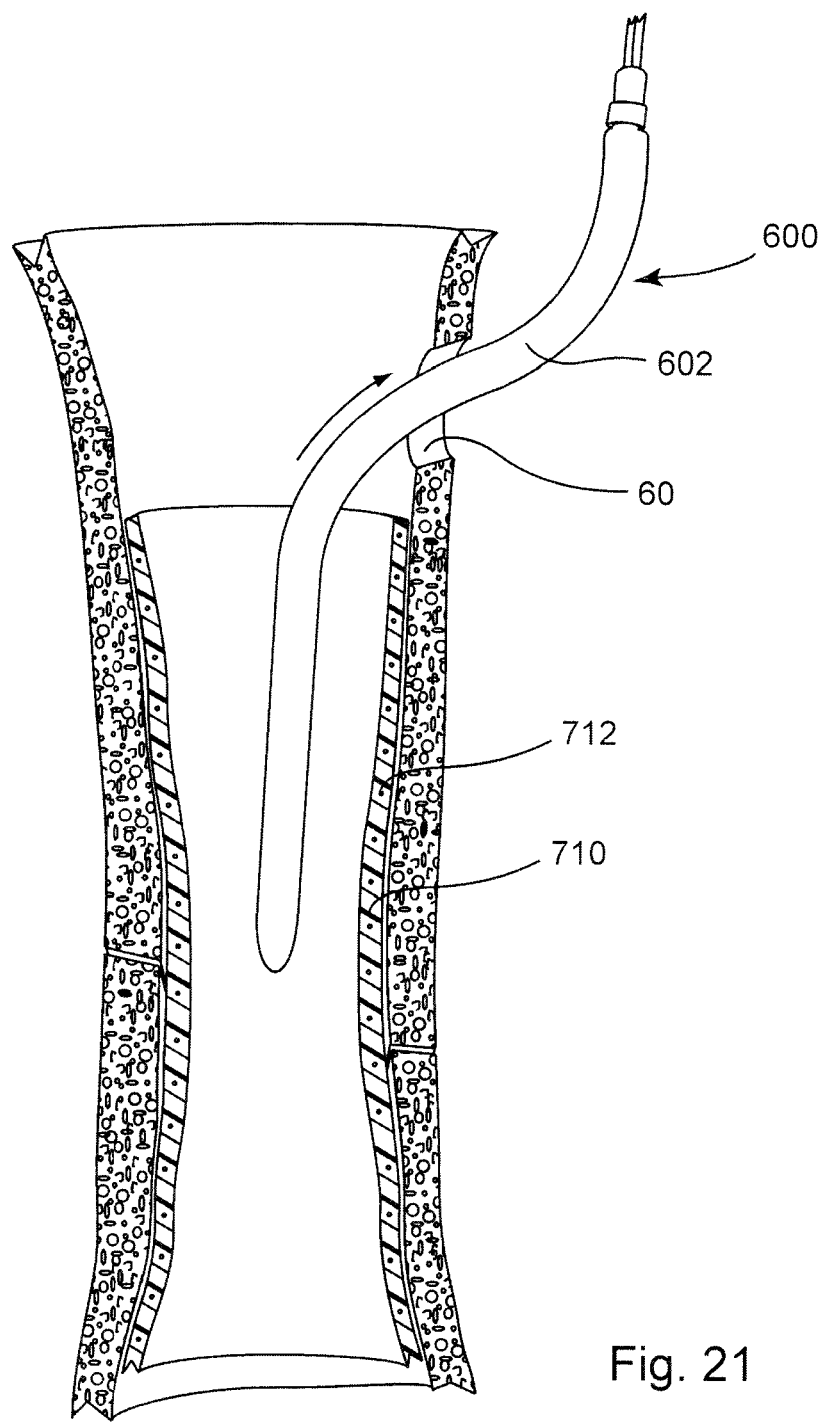
FIG. 21 is a longitudinal cross-sectional view of the bone, intramedullary bone fixation device and balloon expansion apparatus of FIG. 17, with the balloon in a deflated state and the and intramedullary bone fixation device in an expanded state, with the balloon expansion apparatus partially removed from the intramedullary bone fixation device.

Referring to FIG. 21, the balloon expansion apparatus 600 is depicted being withdrawn from the composite device 710. After expansion of the elastic bladder 602 is accomplished as described previously, the liquid in the elastic bladder 602 may be cooled by pumping cool liquid in through input hose 606 and withdrawing warmer liquid through output hose 608 until a consistently cooler liquid is in the bladder 602. The cooler liquid in the bladder absorbs thermal energy from the matrix 716, allowing it to cool and transform from the flexible first thermo-chemical state to the hardened second thermo-chemical state. Once the composite device 710 has thus cooled and hardened, the remaining liquid may be pumped out of the elastic bladder 602, and the balloon expansion device 600 is pulled out of composite device 710 through the percutaneous portal 60.

A protective, tubular insertion sheath (not pictured) may surround all or a portion of any of the above-described intramedullary bone fixation devices during the implantation procedure, and may optionally be removed following implantation. The insertion sheath may be very thin, and may prevent portions of the support structure or matrix from snagging on or scratching the intramedullary canal, or portions of the fractured bone. Once the device is inserted, the sheath may be removed by being pulling the sheath out through the delivery tube, while leaving the device behind.

With any embodiment of the device, after insertion of the device but before conclusion of the implantation procedure, x-ray, fluoroscopy, or other radiographic methods may be implemented to assess the alignment of the device relative to the bone. If alignment is unsatisfactory, a heating element (not shown) or a heatable expansion device such as the balloon apparatus 600 or mechanical expansion apparatus 500 as described previously may be introduced into the central core. The device is heated so the thermoplastic matrix again reaches first thermo-chemical state, and the device may then be removed and reinserted or otherwise adjusted until a satisfactory alignment is achieved. The device is allowed to cool, so the thermoplastic matrix returns to the second thermo-chemical state through the natural dissipation of energy into the surrounding tissue.

Post-implantation, the device may be removed if desired. The method of removal will vary, depending on the state of the decomposition of the biocompatible thermoplastic matrix. If the thermoplastic matrix is still intact, a percutaneous portal may be opened and a tube may be inserted. The tube may be the same as or similar to the delivery tube 62 described previously. A heating element or heatable expansion apparatus such as the mechanical expansion apparatus 500 or balloon expansion apparatus 600 is introduced into the central core, and the device is heated until the matrix reaches the first thermo-chemical state, above the glass transition temperature. The heat source is removed; the device may be contracted by holding the rods steady and pulling longitudinally on the cage. The device may be removed through the delivery tube, or directly through the percutaneous portal. If the thermoplastic matrix has been sufficiently absorbed so that it is no longer intact, no heating is required; the device is contracted and removed.

Another embodiment of the invention (not shown) comprises a support structure and an alternative form of the thermoplastic matrix, comprising an injectable form of a synthetic biodegradable polymer, poly-D,L-lactic acid-polyethyleneglycol (PLA-PEG). This biodegradable composite is temperature-sensitive so that when it is heated it takes on a liquid, semi-solid form and following injection, cools and becomes semi-solid. A structure such as support structure 11, 711, 811 or 71 is introduced into the intramedullary canal. The structure may have a protective sheath surrounding the portion of the structure which will be adjacent to the fracture location. Following insertion of the support structure into the intramedullary canal, and radial expansion of the support structure, heated PLA-PEG is injected through a flexible tube or catheter which is inserted through the delivery tube 62 into the central core. The liquid PLA-PEG flows through the web-like support structure, filling the canal and surrounding the support structure. The protective sheath prevents the PLA-PEG from contacting the fractured area of the bone. The PLA-PEG is allowed to cool and harden, and provides rigid support around the structure.

Figures 22A, 22B:
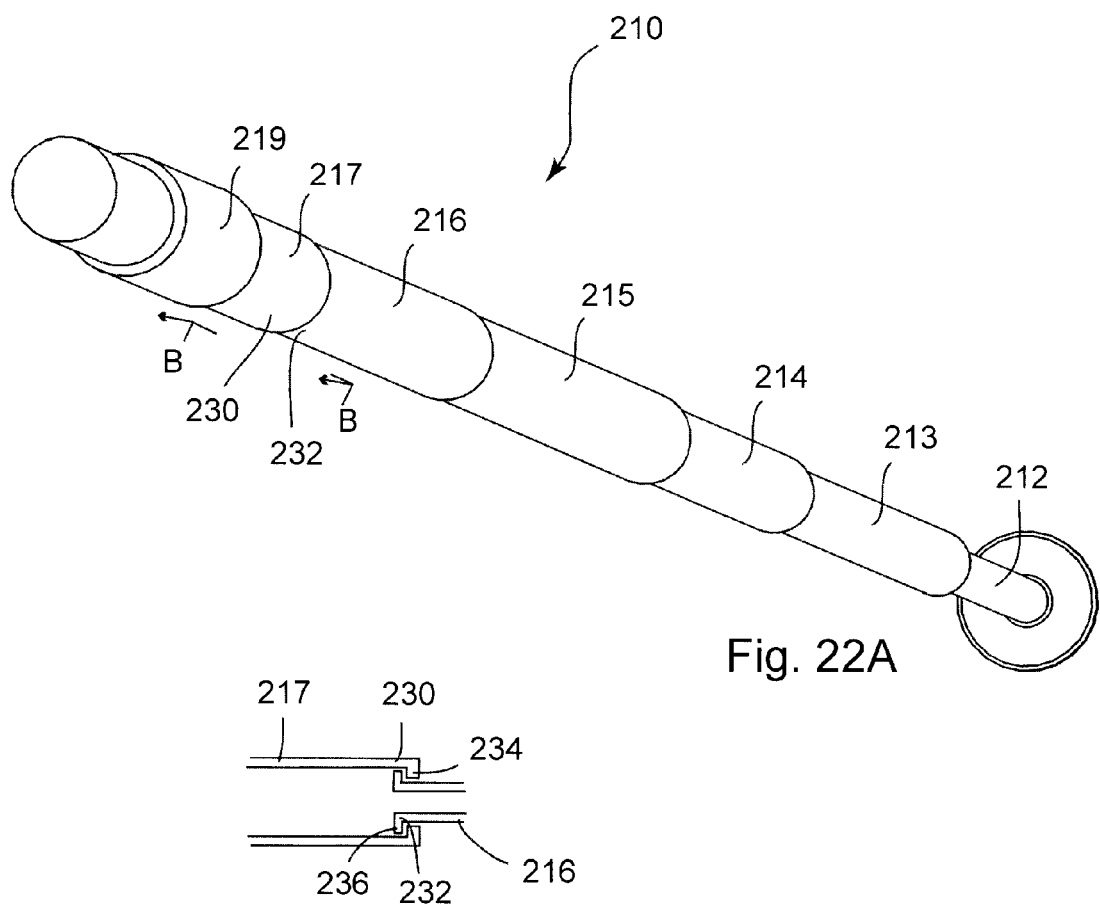
FIG. 22A is a perspective view of a telescoping bone fixation device in an extended state according to one alternative embodiment of the invention.
FIG. 22B is a longitudinal cross-sectional view of a connection between two nesting components of the telescoping bone fixation device of FIG. 22A.

Referring to FIG. 22A, a perspective view shows another embodiment of the invention, comprising a telescoping intramedullary fixation device 210. This device comprises a central wire 212 surrounded by a series of five tubular nesting components 213-217. Each tubular nesting component is substantially the length of the entire device 210 when all components are nested together, and each successive nesting component is slightly wider in diameter than the component it surrounds. Other embodiments of the telescoping intramedullary fixation device 210 may have fewer, or more, than five nesting components. The central wire 212 may have a solid core and may not be tubular, but is slender and thus sufficiently flexible to be inserted into the intramedullary canal. The nesting components 213-217 may comprise metal, a biocompatible polymer material, or a mesh-like stent material (such as those depicted in FIG. 3), and may be embedded in a thermoplastic matrix material. FIG. 22A displays the telescoping device 210 in a fully extended or telescoped position; however when completely implanted in a patient the device 210 is in a collapsed position in which the nesting components are concentrically nested together.

The first nesting component 213 surrounding the central wire 212 is slightly wider in diameter than the central wire 212. Each successive nesting component 214-217 is slightly wider than the preceding one, and as the nesting components increase in diameter, the width of the wall of the component may decrease so that each nesting component is still flexible enough to be inserted into the canal. The wall thickness of each of the nesting components 213-217 may advantageously be selected such that the nesting components 213-217 are all nearly equally flexible. According to one alternative embodiment (not shown), the nesting components do not have solid walls but have slots in the walls to increase flexibility.

In a patient, the central wire 212 may first be inserted into the intramedullary canal. Then, successive nesting components 213-217 with increasing diameters are introduced into the intramedullary canal. The nesting component 213 with the smallest diameter is slid in around the central wire 212; the nesting component 214 with the next largest diameter is slid in surrounding the first nesting component 213, and the remaining nesting components 215-217 are inserted in a similar fashion. The largest nesting component 217 fits just inside the walls of the canal. After the components are inserted and collapsed together, an injectable, hardenable polymer such as bone cement or a biocompatible polymer such as PLA-PEG may be introduced into the canal to fill any spaces between the largest nesting component 217 and the wall of the canal. The largest nesting component 217 may have a sheath 219 which prevents the polymer from accessing the fractured area of the bone, as described previously. The nested set of nesting components 213-217 has a combined strength and rigidity which exceeds that of any of the individual nesting components, and the device 210 provides strength and support during bone healing.

FIG. 22B is an enlarged, stylized cross-sectional view of the connection between nesting components 216 and 217; however the figure is representative of the connections between each of the nesting components 213-217. Nesting component 217 has a first end 230 with an inward-projecting first lip 234. The next smallest nesting component 216 has a second end 232 with an outward-projecting second lip 236.

The projecting lips 234, 236 allow for easy removal of the apparatus. During removal, initially a slap hammer is used to break the largest nesting component 217 away from the bone cement. Nesting component 217 is pulled out first, and its inwardly-projecting lip 234 hooks the outwardly-projecting lip 236 of the next largest nesting component 216, and causes it to be pulled out, followed by the next largest nesting component 215, until all the nesting components 213-217 are pulled out. The central wire 212 is removed separately after all the nesting components are removed.

Figure 23:
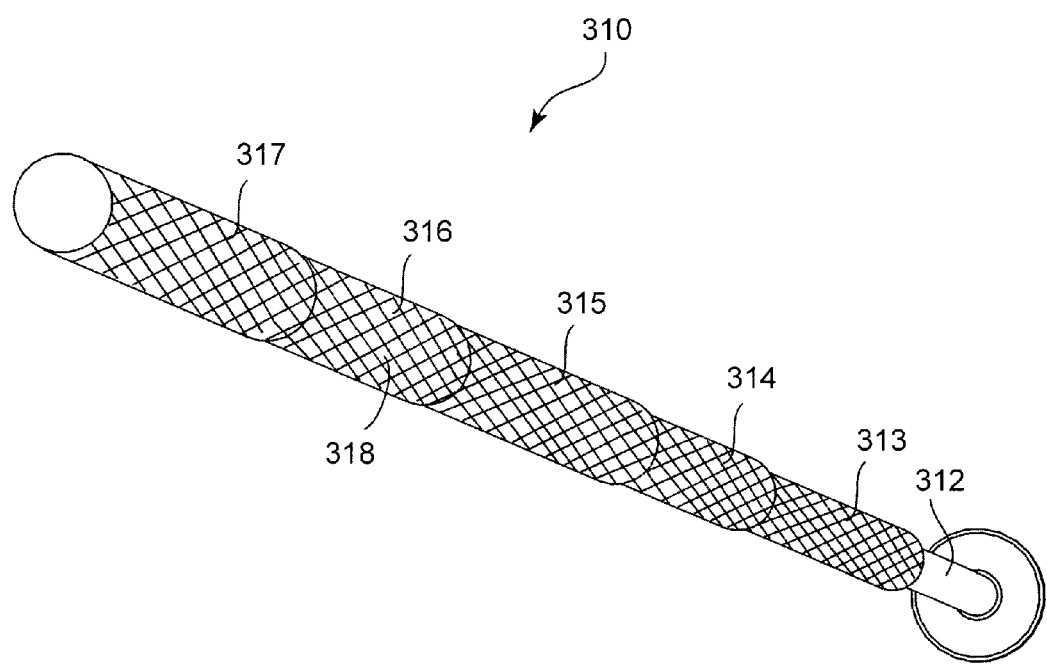
FIG. 23 is a perspective view of a telescoping bone fixation device with mesh-like components and a thermoplastic matrix according to another alternative embodiment of the invention, in an extended state.

Referring to FIG. 23, another embodiment of a telescoping fixation device is shown in an extended state. In this embodiment, telescoping fixation device 310 comprises a series of nesting components 313-317, each of which comprises a mesh-like stent portion embedded in thermo-plastic matrix material 318 similar to that of the thermoplastic matrix 16 of FIGS. 1 and 6. Each nesting component 313-317 is substantially the length of the entire device 310 when all components are nested together. Prior to implantation, the device 310 is heated as described previously so that the thermoplastic matrix material 318 reaches the first thermo-chemical state, and is rubbery and flexible. The device 310 is telescoped out into an extended configuration, and introduced into the intramedullary canal through an opening transverse to the longitudinal axis of the bone. The central wire 312 is introduced first, and the adjacent and smallest nested component 313 is inserted so it nests around the central wire. The next smallest nested component 314 is nested about the smallest nested component 313, and so on until all the remaining nested components 315-317 are introduced into the intramedullary canal and nested together. The device 310 is allowed to cool so that energy dissipates into the surrounding tissue, and the thermoplastic matrix material 318 of each nesting component 313-317 reaches the second thermo-chemical state, and hardens.

Figure 24:
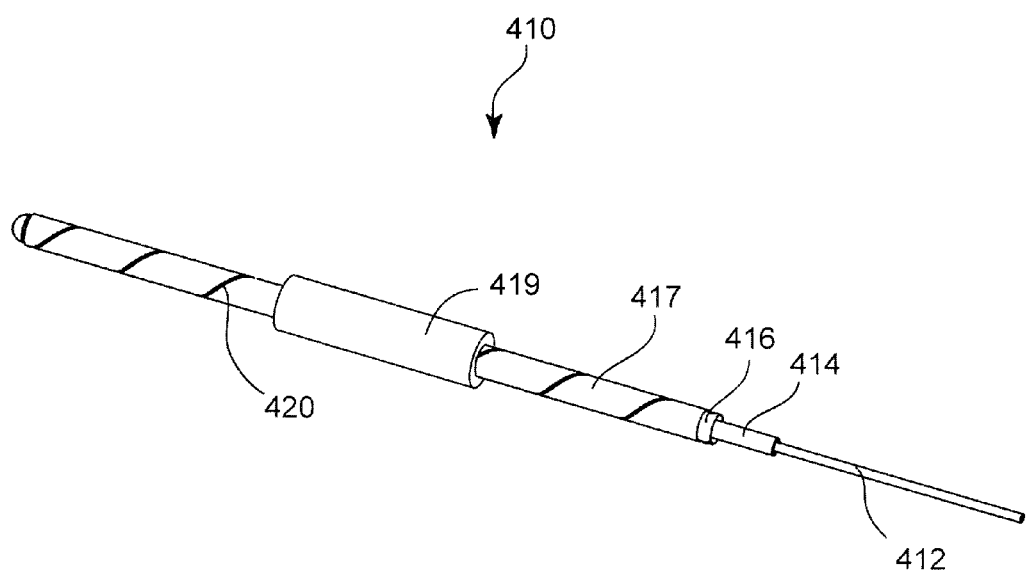
FIG. 24 is a perspective view of a helically threaded telescoping bone fixation device according to yet another alternative embodiment of the invention, in a partially extended state.

Referring to FIG. 24, another alternate embodiment of a telescoping fixation device is shown, in a partially extended state. In this embodiment, telescoping fixation device 410 comprises a series of nesting components 413-417, which are helically threaded so that during implantation each nesting component is threaded onto the preceding smaller component. The direction of the threading on each nesting component may alternate, so that each nesting component is threaded onto the next nesting component in the opposite direction from the previous one. Each nesting component 413-417 is substantially the length of the entire device 410 when all components are nested together. As with devices 210 and 310, five nesting components are described, however in alternate embodiments the number and size of the nesting components may vary.

Similar to the telescoping fixation devices 210 and 310, device 410 has a central wire 412 which is initially inserted into the intramedullary canal through a delivery tube 62 or similar interface. The first nesting component 413 is slid in around the central wire. The first nesting component 413 is tubular in form has a clockwise helical protrusion 420 which protrudes on the outside of the tube, winding in a clockwise direction along the length of the nesting component 413.

Figure 25A:
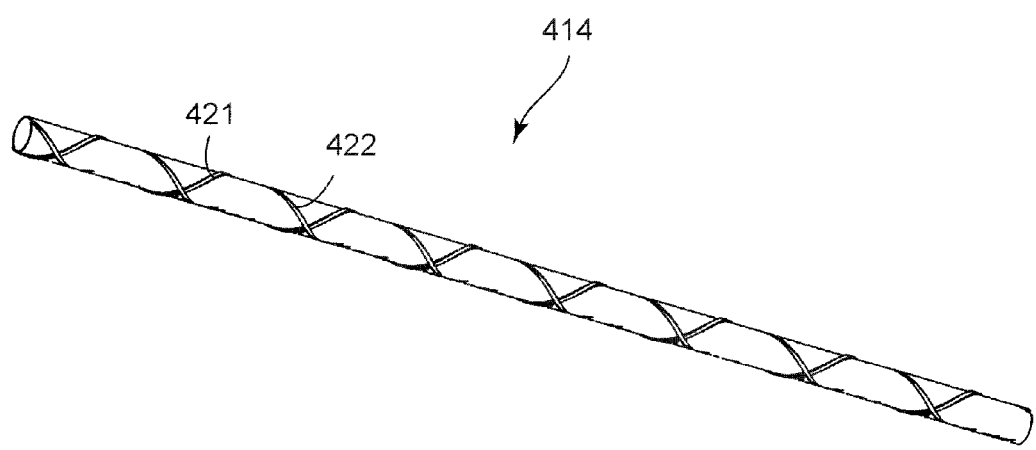
FIG. 25A is a perspective view of one nesting component of the helically threaded telescoping bone fixation device of FIG. 24.
Figure 25B:
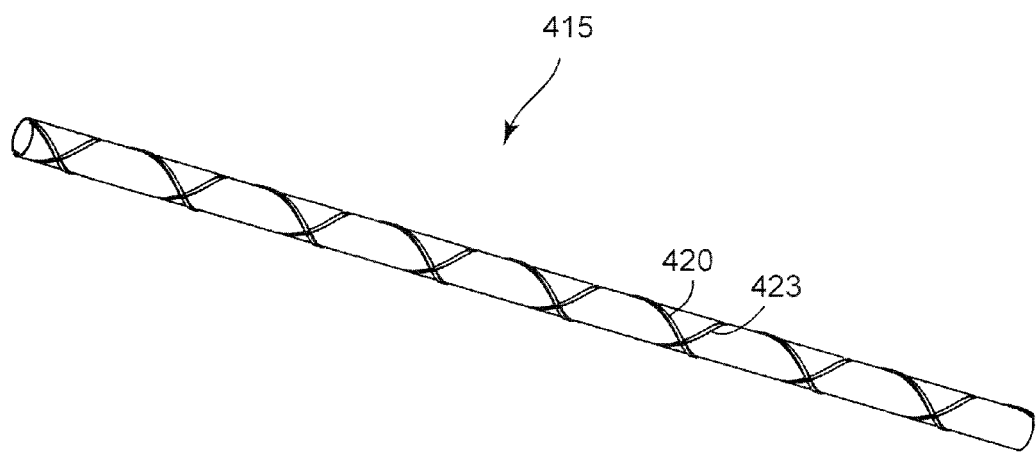
FIG. 25B is a perspective view of another nesting component of the helically threaded telescoping bone fixation device of FIG. 24.

Referring to FIGS. 25A-25B, two adjacent helically threaded nesting components have threading configurations which wind in opposite directions. As seen in FIG. 25A, the second nesting component 414 has a clockwise helical slot 422 which winds clockwise along its length, and a counter-clockwise helical protrusion 421 which winds counter-clockwise along its length. As nesting component 414 is inserted into the intramedullary canal, it is twisted clockwise so that its clockwise helical slot 422 fits over the clockwise helical protrusion 420 on the first nesting component 413. As seen in FIG. 25B, the third nesting component 415 has a counter-clockwise helical slot 423, and a clockwise helical protrusion 420. It is inserted and threaded onto the second nesting component 414 in a counter-clockwise fashion, so that its counter-clockwise helical slot 423 engages with the counter-clockwise helical protrusion 421 on the second nesting component 414. Each remaining nesting component is threaded clockwise or counter-clockwise to engage with the smaller component nested inside of it. The outermost nesting component 417 may or may not have a helical protrusion.

The helical threading system varies in direction so that the entire device will not be loosened when the outermost component 417 is turned in one direction. In addition, this bi-directional threading system adds overall torsional strength to the telescoping fixation device 410, since a twisting force in one direction will not disengage all the threading on the nesting components.

The telescoping fixation device 410 may be used in conjunction with an injectable hardenable polymer, such as bone cement or a biocompatible polymer such as PLA-PEG, among others. The fixation device 410 may be implanted as described previously, and the injectable polymer may then be injected into the intramedullary canal around the periphery of the device, to fix the device in place. The outermost nesting component 417 may have a protective sheath 419 which prevents the polymer from accessing the fractured area of the bone, as described previously. Removal of the device 410 is accomplished by breaking the device away from the polymer as described previously, then unthreading and removing each component 413-417 in a clockwise or counter-clockwise direction, beginning with the outermost component 417 and proceeding inward.

Figure 26:
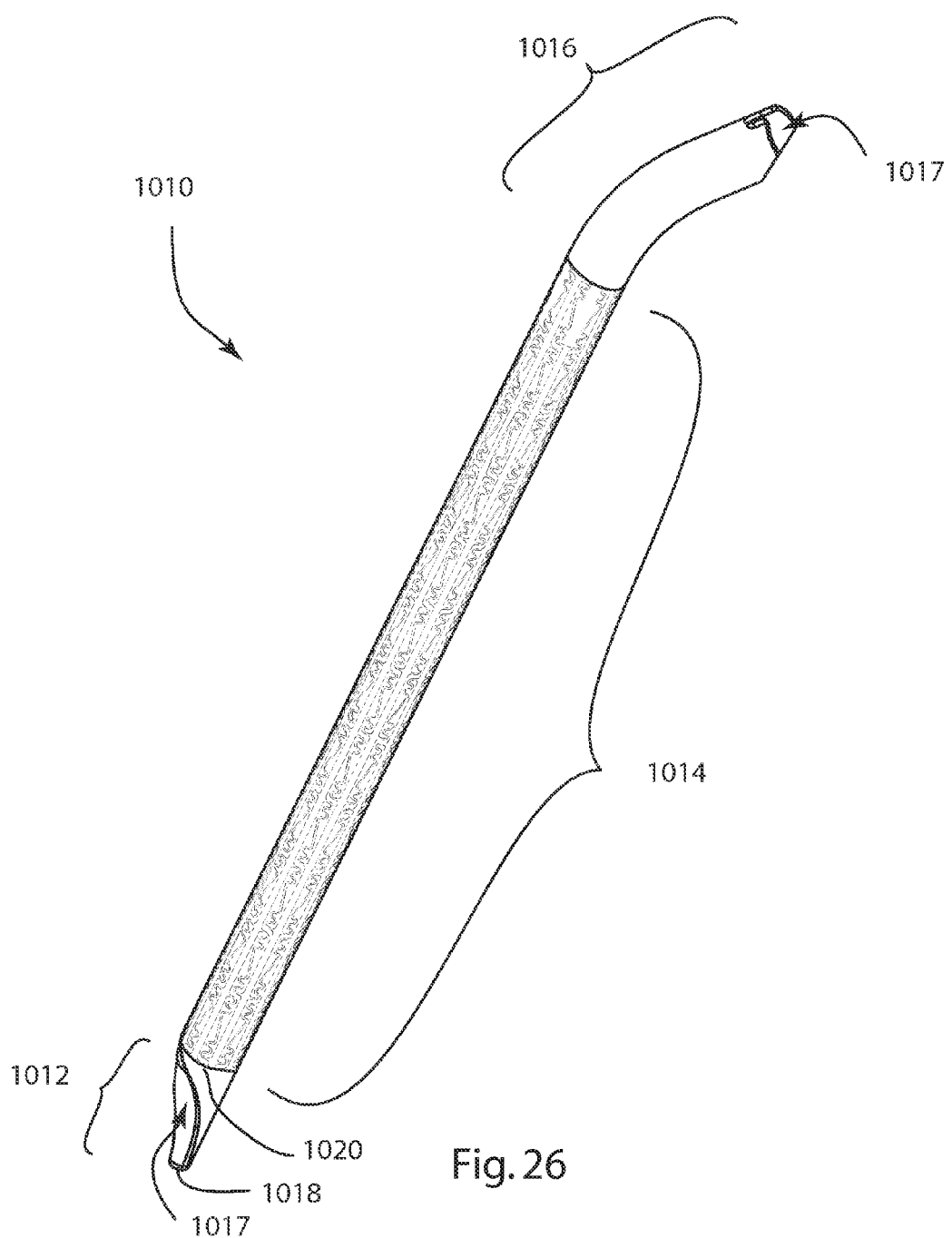
FIG. 26 is a perspective view of a composite intramedullary bone fixation device.

Another alternative embodiment of an intramedullary bone fixation device is depicted in FIG. 26. Fixation device 1010, which may also be described as an intramedullary nail, has an elongated shape and comprises a distally located nose portion 1012, a central portion 1014 occupying a middle position, and a proximally located attachment portion 1016. A bore 1017 extends the length of the device. The fixation device 1010 is designed to be inserted into the intramedullary canal of a fractured bone along a path that is not parallel to the intramedullary canal, and once inserted may be radially expanded to fill the intramedullary canal and provide rigid support to the bone during healing. To allow for insertion of the device over a guidewire, and to allow space for an expansion apparatus, the fixation device 1010 may be cannulated along its entire length.

The central portion 1014 may be composite, where composite is defined as at least two non-identical materials deliberately combined to form heterogeneous structures with desired or intended properties. For example, a composite central portion may comprise a metal support structure which is embedded in thermo-chemically activated matrix material. In the present embodiment, the two non-identical materials are the metal which comprises the support structure, and the matrix material. The nose portion 1012 and the attachment portion 1016 may each be non-composite, in that each may comprise one material, such as matrix material, metal or metal alloy, ceramic, or polymer, among others.

The nose portion 1012 of the fixation device 1010 has a distal tip 1018, and a proximal transition end 1020 where the nose portion 1012 joins the central portion 1014. The nose portion 1012 may be substantially tapered from the transition end 1020 to the tip 1018. This taper allows for easier introduction of the nose portion 1012 into the intramedullary canal, and may match the morphology of the distal end of the intramedullary canal. The nose portion 1012 may be made of a thermo-mechanically or thermo-chemically activated thermoplastic matrix material, and may be radially expandable. The thermo-chemically activated thermoplastic matrix material is configured to be substantially deformable at a first thermo-chemical state, and substantially hardened at a second thermo-chemical state.

The thermoplastic matrix material may comprise a combination of PCLM-12, SMC-7, and A-6. PCLM-12 is a polyaxial copolymer made of about 98/2 (molar) ε-caprolactone/glycolide. The polymer is made using stannous octanoate and triethanolamine as the catalyst and initiator, respectively. The composition of PCLM-12 protected in part by U.S. Pat. No. 7,048,753, which is incorporated herein by reference. SMC-7 is a segmented copolymer made of about 88/12 (molar) l-lactide/trimethylene carbonate using 1,3-propanediol and stannous octanoate as the initiator and catalyst, respectively. The composition of SMC-7 is protected by U.S. Pat. Nos. 7,192,437 and 6,342,065, and European Patent 1,057,844, which are incorporated herein by reference. A-6 is a microparticulate nucleating agent, and is protected in part by a number of patents including U.S. Pat. No. 6,413,539 and European Patents 0,737,703 and 0,952,171, which are incorporated herein by reference.

Specifically, the nose portion 1012 may be formed of a matrix material comprising 95 to 99.9% by weight of a blend of PCLM-12 and SMC-7, and 0.1 to 5% of A-6. More specifically, the nose portion may comprise a matrix material comprising a blend of PCLM-12, SMC-7, and A-6, in which the PCLM-12 may range from 30 to 70% by weight, the SMC-7 may range from 30 to 70% by weight, and the A-6 may range from 0.1 to 5% by weight. Still more specifically, the nose portion 1012 may be made of a matrix material comprising 98% by weight of a blend of 45% by weight of PCLM-12 and 55% by weight of SMC-7; and 2% by weight of A-6.

Figure 27:
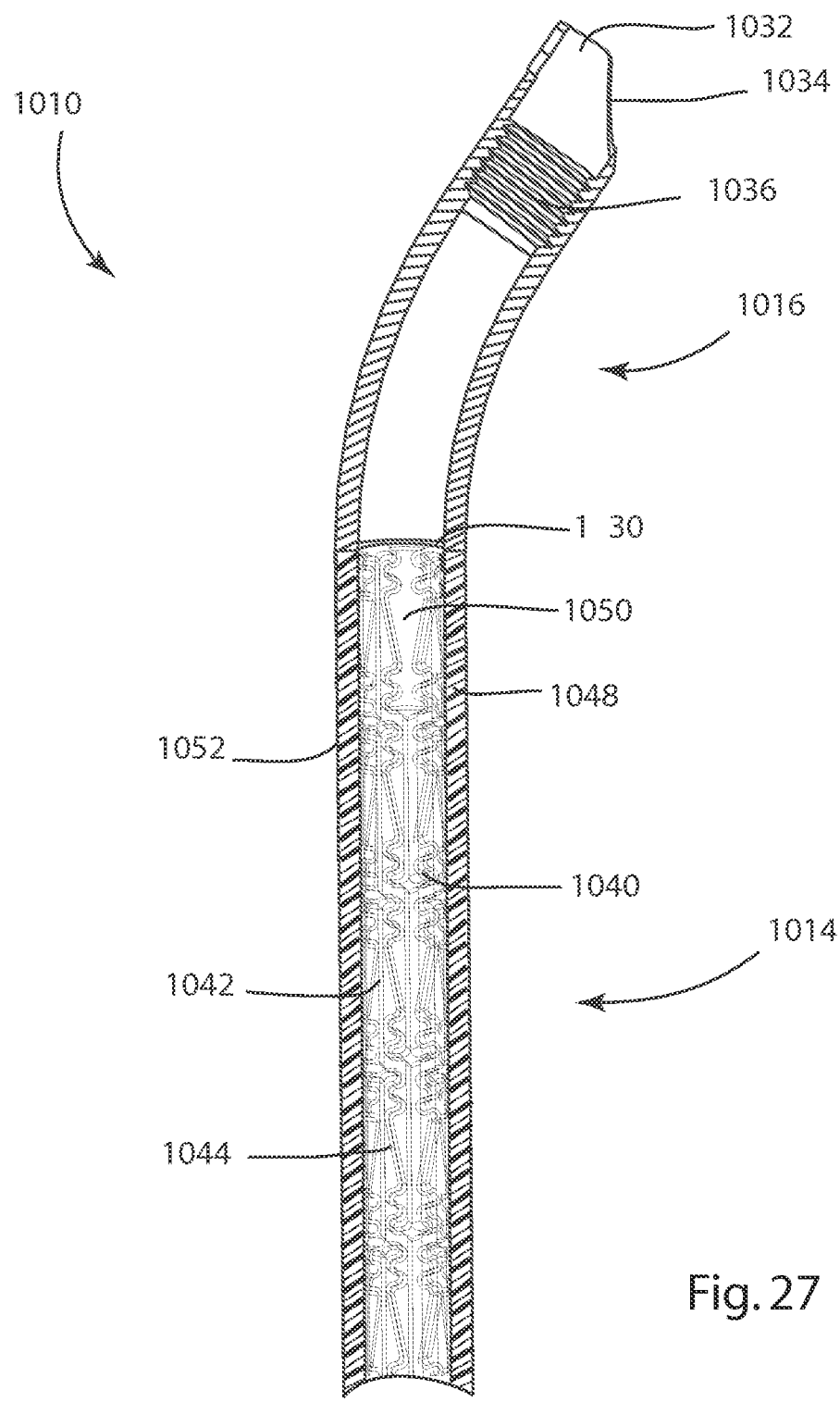
FIG. 27 is a cross-sectional view of the proximal end of the composite intramedullary bone fixation device of FIG. 26.

Referring to FIG. 27, a longitudinal cross-sectional view of a proximal portion of the fixation device 1010 is shown, with detail of the attachment portion 1016 and the central portion 1014. The attachment portion 1016 is a substantially rigid, slightly curved tube which extends proximally from a proximal end of the central portion 1014. The attachment portion 1016 may be curved so that it may reach from the substantially straight intramedullary canal to an opening created in the bone, which opening may be transverse to the longitudinal axis of the intramedullary canal. The attachment portion 1016 joins the central portion 1014 at a distal transition end 1030. At a proximal end 1032 is an opening 1034. The opening 1034 may be shaped to mate with a handle used the device insertion process.

Slightly recessed from the opening 1034 may be an attachment connection feature 1036, which may comprise threads, slots, protrusions, grooves or other elements which may be used to connect the device 1010 to hoses, expansion apparatuses, or other devices. The attachment portion 1016 may be made from a rigid material such as a metal or metal alloy, to provide rigid support during manipulation such as insertion or removal of the device 1010. More specifically, the attachment portion 1016 may be made from cobalt-chrome-molybdenum (CCM).

Between the nose portion 1012 and the attachment portion 1016 extends the central portion 1014. The central portion 1014 may be generally straight and tube-like, and may be capable of radial expansion, so that in an expanded state within the intramedullary canal it may provide support to the surrounding fractured bone. As set forth previously, the central portion 1014 may be composite, comprising a support structure and a thermo-chemically activated thermoplastic matrix. In the embodiment depicted in FIG. 27, the support structure 1040 is a laser-cut stent, cut from CCM. At the proximal end of the central portion 1014, the CCM of the support structure may be continuous with the CCM of the attachment portion 1016. In alternative embodiments, the CCM of the support structure may be press-fit or otherwise joined to the CCM of the attachment portion.

The support structure 1040 is laser-cut to a pattern of ribs 1042 interconnected by web-like struts 1044. The laser-cut pattern allows the central portion 1014 to flex when necessary, such as during insertion and removal of the device 1010. It also allows for radial expansion of the central portion 1014; when outward pressure is applied from within the central portion, the orientation of the struts shifts to allow expansion. The wavy portions of the struts 1044 can bend and flex, without breaking. One aspect of the laser-cut pattern is that it may minimize elastic recovery such that once expanded, the support structure 1040 may exhibit minimal drift back to its original shape. In other embodiments of the invention, support structures comprising other laser-cut patterns or other methods of manufacture may be included.

During manufacture, the support structure 1040 is embedded in a thermo-mechanically or thermo-chemically activated thermoplastic matrix 1048 through an injection molding process. In FIG. 27, only the boundaries of the semi-translucent matrix 1048 are shown, so that the support structure 1040 is visible. However, the matrix 1048 is injection molded so that it surrounds the support structure 1040 and the support structure is embedded within it. As set forth previously, the fixation device 1010 is cannulated, so the matrix 1048 is not solid across the transverse cross section of the device; instead the matrix 1048 is a hollow tube in which the support structure is embedded. The inner surface of the tube is an inner bore wall 1050, while the outer surface is an outer wall 1052. The matrix 1048 may extend proximally past the proximal end of the central portion 1014 and may surround some fraction of the attachment portion 1016. At the distal end of the central portion, the matrix 1048 may be continuous with the matrix material comprising the nose portion 1012, may abut it, or may overlap some of the nose portion.

The matrix 1048 may be made of the same thermo-chemically activated thermoplastic matrix material of which the nose portion 1012 is made. The matrix 1048 may comprise a combination of PCLM-12, SMC-7, and A-6. Specifically, the matrix 1048 may be made of a matrix material comprising 95 to 99.9% by weight of a blend of PCLM-12 and SMC-7, and 0.1 to 5% of A-6. More specifically, the matrix 1048 may comprise a matrix material comprising a blend of PCLM-12, SMC-7, and A-6, in which the PCLM-12 may range from 30 to 70% by weight, the SMC-7 may range from 30 to 70% by weight, and the A-6 may range from 0.1 to 5% by weight. Still more specifically, the matrix 1048 may be made of a matrix material comprising 98% by weight of a blend of 45% by weight of PCLM-12 and 55% by weight of SMC-7; and 2% by weight of A-6.

Figure 28A:
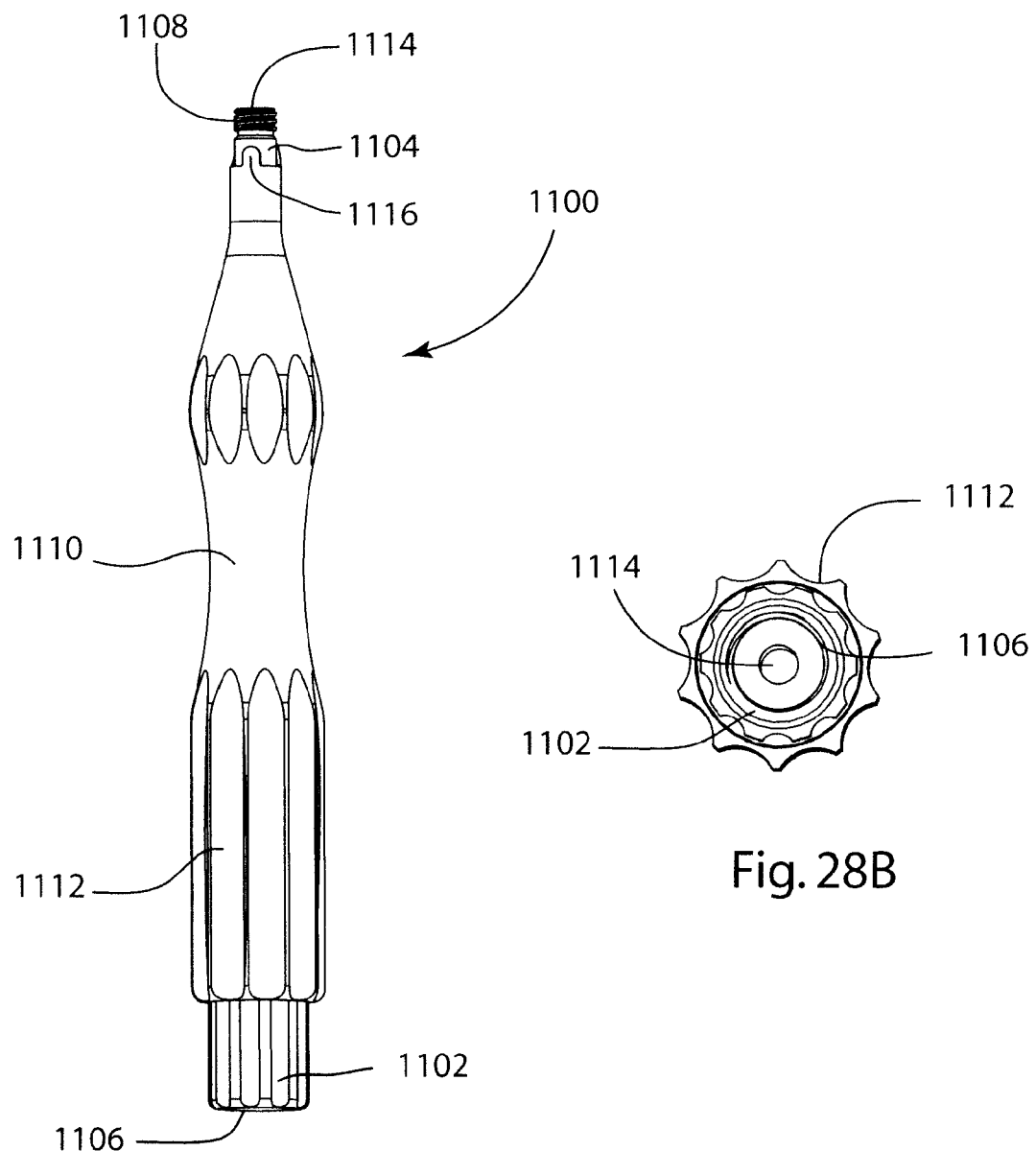
FIG. 28A is a side view of a handle.

FIG. 28A depicts a handle 1100 which may be releasably connected to the proximal end of the fixation device 1010. The handle 1100 has a handle body 1110, with a proximal end 1102 and a distal end 1104. An ergonomic gripping portion 1112 encompasses the body 1110 near its proximal end 1102. A proximal connection feature 1106 is located at the body proximal end 1102, and a distal connection feature 1108 is located at the body distal end 1104. The distal connection feature 1108 is configured to connect with the attachment connection feature 1036 on the fixation device 1010. In this embodiment of the invention the distal connection feature 1108 comprises threads, however in other embodiments it may comprise slots, grooves, protrusions, or other elements configured to mate with the attachment connection feature 1036. Additionally, the distal end 1104 may have a mating feature 1116 configured to mate with the opening 1034 of the attachment portion 1016 of the fixation device 1010.

Figure 28B:
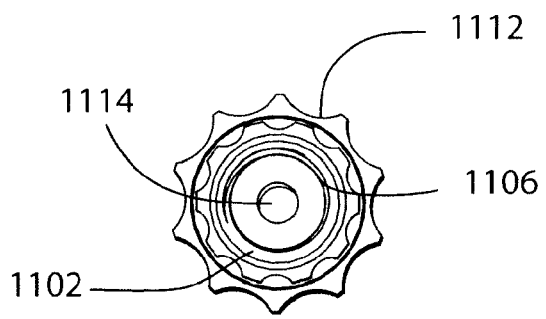
FIG. 28B is proximal end view of the handle of FIG. 28A.

FIG. 28B is an end view of the body proximal end 1102 of the handle 1100. The proximal connection feature 1106 is seen as a series of threads; however it may comprise threads, slots, grooves, protrusions or other elements, in other embodiments of the invention. Extending lengthwise through the handle is a bore 1114. When the handle 1100 is connected to the fixation device 1010, the bore 1114 of the handle 1100 abuts the bore 1017 of the fixation device 1010, so there is a continuous uninterrupted passageway through the handle 1100 and the fixation device 1010. The handle may be connected to the fixation device 1010 and used to insert the fixation device 1010 into the intramedullary canal of the bone. The handle may also be used as an intermediate connection piece between an expansion apparatus and a pump system which supplies fluid to the expansion apparatus.

Figure 29:
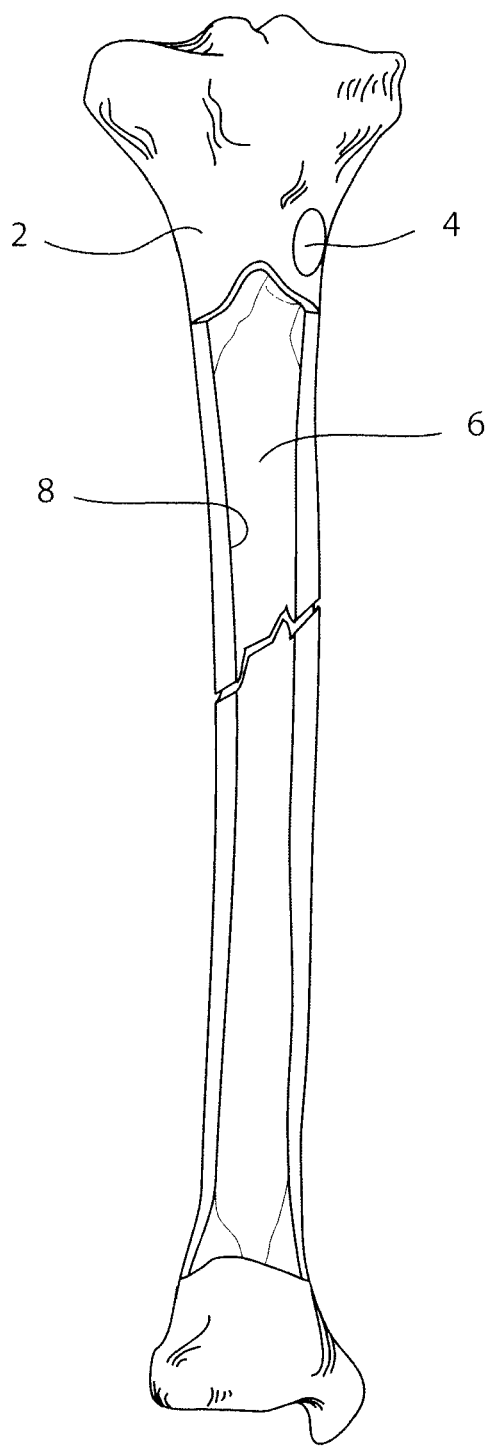
FIG. 29 is a lateral partial cross-sectional view of a fractured bone.

FIGS. 29-32 illustrate how the fixation device 1010 may be inserted into the intramedullary canal of a bone. FIG. 29 is a perspective, partially cutaway view of a fractured tibia 2. To prepare for insertion of the intramedullary device, an opening 4 is drilled in the tibia, distal of the growth plate, so that bone growth will not be disturbed, which may be of special importance in pediatric patients. The intramedullary canal 6 extends substantially the length of the bone, and is surrounded by a wall 8.

Figure 30:
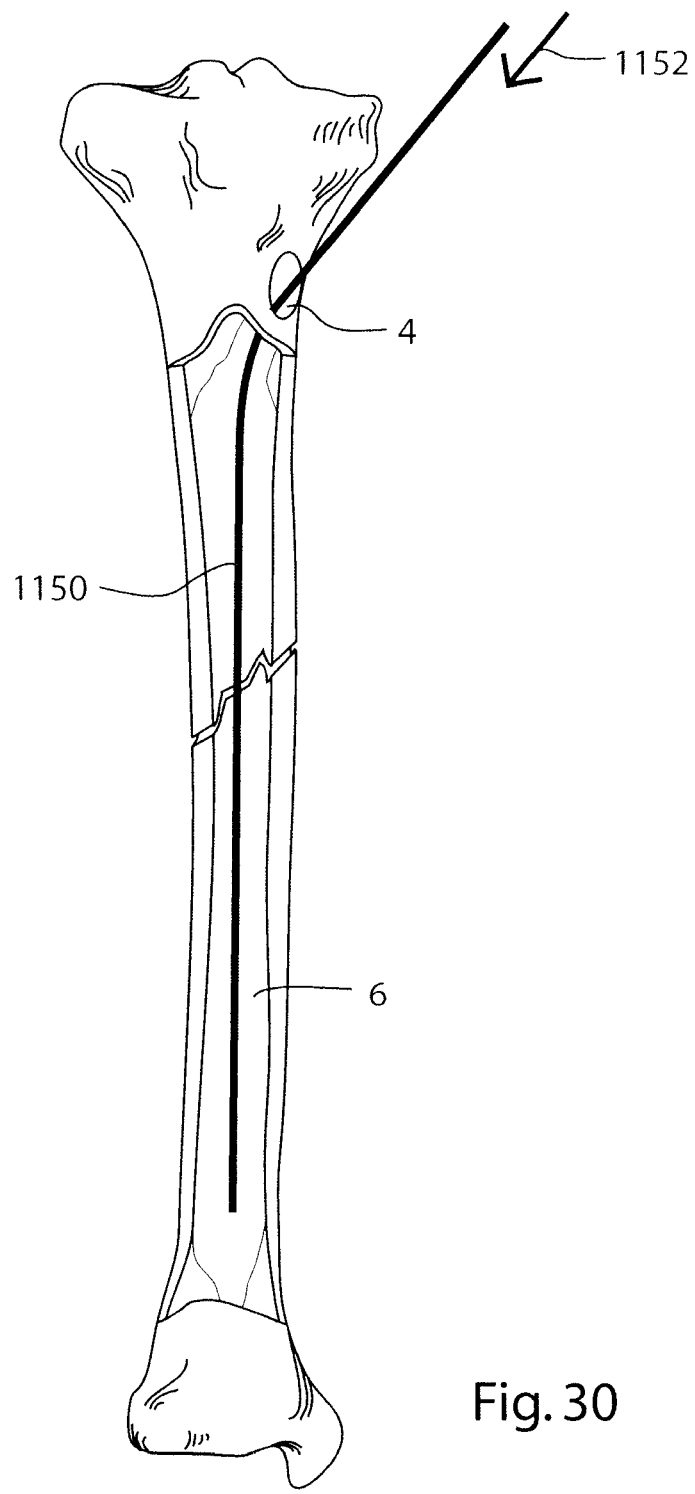
FIG. 30 is a lateral view of a guidewire being inserted into the intramedullary canal of the fractured bone of FIG. 29.

Referring to FIG. 30, a removable guidewire 1150 may be inserted through the opening 4 into the intramedullary canal 6, in the direction indicated by direction arrow 1152. The guidewire may comprise Nitinol or another material which is sufficiently flexible to bend as it passes through the opening 4.

Figure 31:
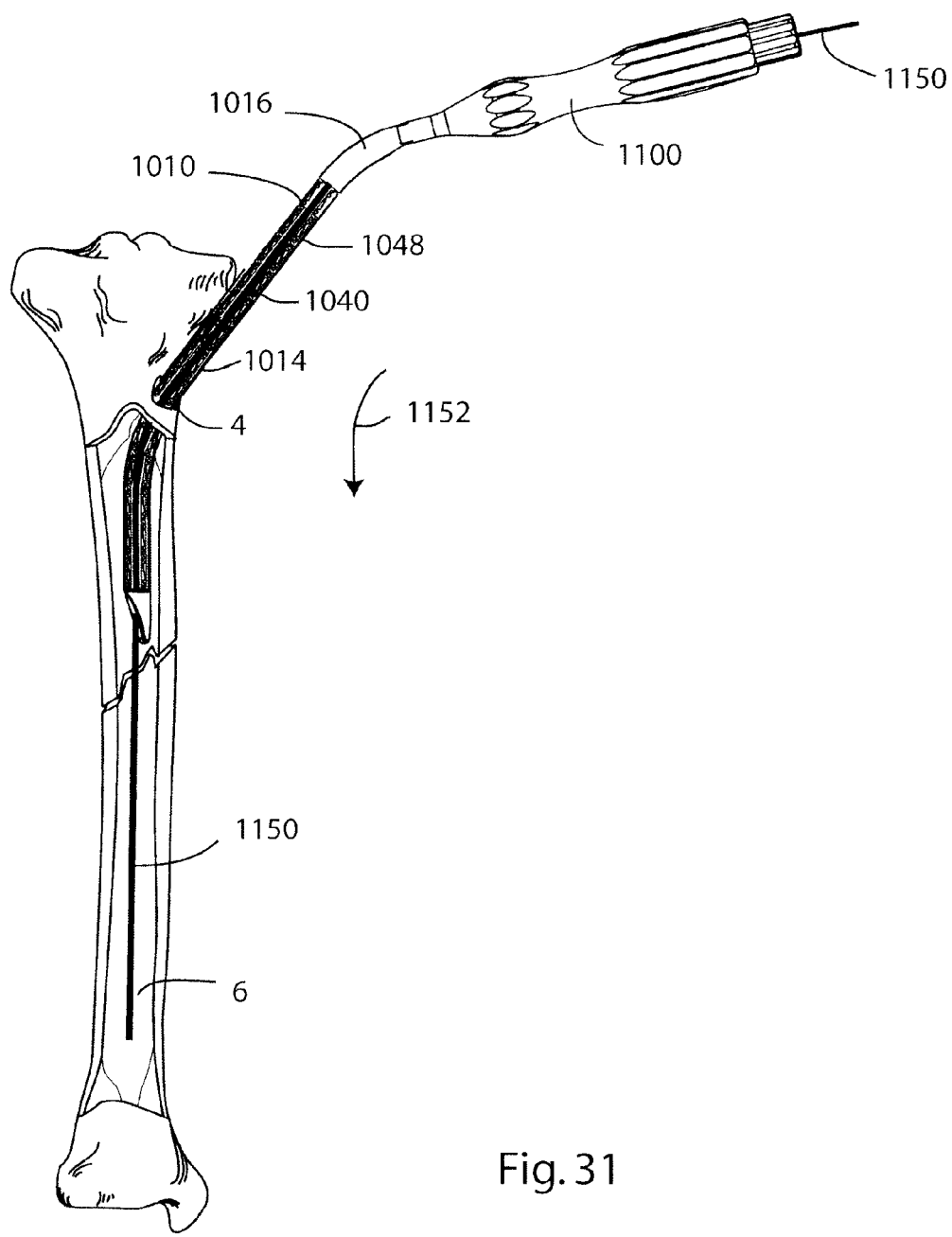
FIG. 31 is a lateral view of the handle of FIG. 28A guiding the composite intramedullary bone fixation device of FIG. 29 over the guidewire of FIG. 30 into the fractured bone.

As seen in FIG. 31, the fixation device 1010 is connected to the handle 1100 at the proximal end of the attachment portion 1016. The handle 1100 is used to guide the fixation device 1010 over the guidewire 1150 into the intramedullary canal 6, along direction 1152. As set forth previously, fixation device 1010 is cannulated along its entire length, and the handle 1100 has a bore extending its entire length, so both the fixation device and the handle may be guided over the guidewire. The central portion 1014 of the fixation device comprises the flexible support structure 1040 and the thermoplastic matrix 1048, which make the central portion 1014 sufficiently bendable to enter the intramedullary canal through the opening 4. Prior to insertion of the fixation device 1010, the fixation device may be heated in a water bath or by other means so that the thermo-chemically activated thermoplastic matrix 1048 attains the first thermo-chemical state, and is substantially deformable to bend as it enters the opening 4 and straighten as it continues along the guidewire 1150.

Figure 32:
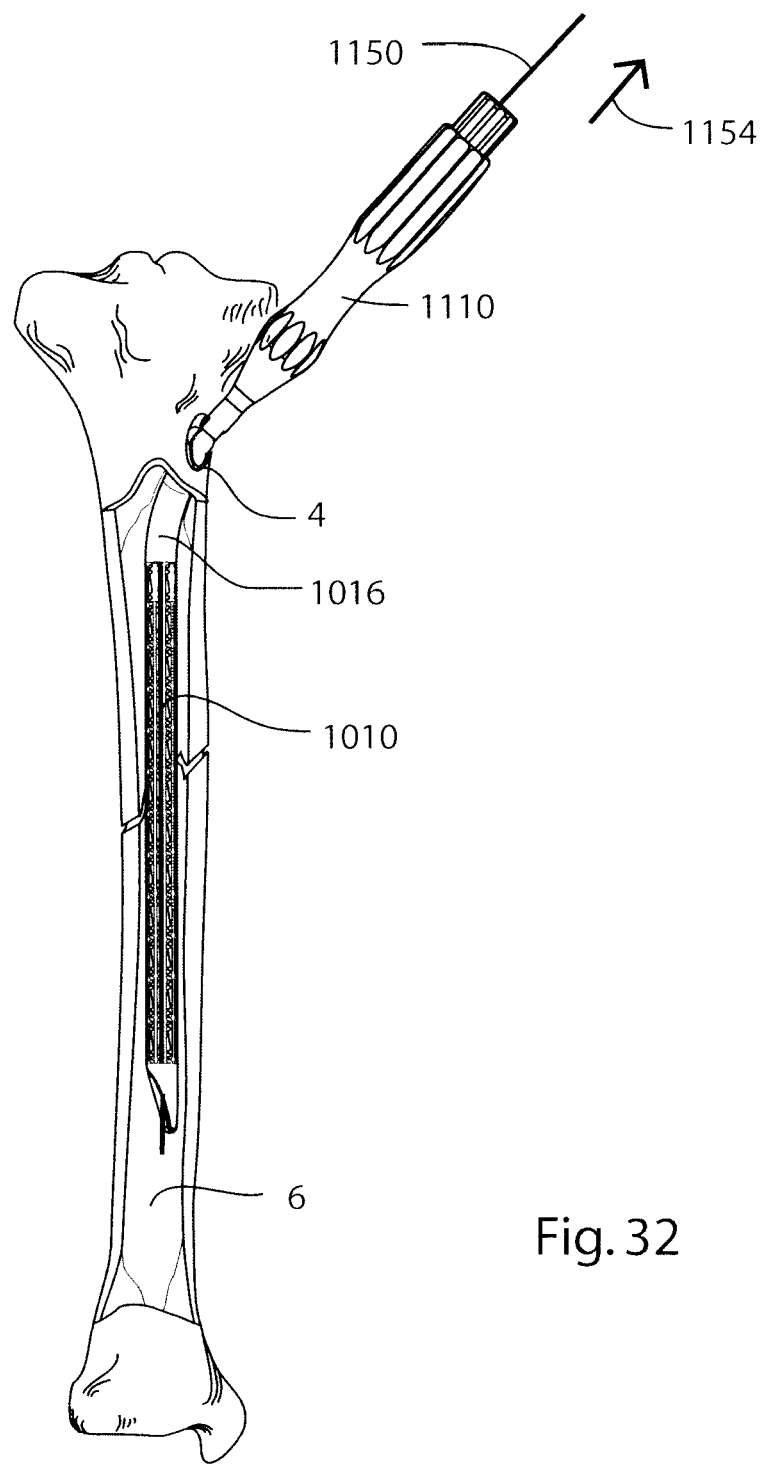
FIG. 32 is a lateral view of the guidewire of FIG. 30 being removed from the intramedullary canal of the fractured bone.

Referring to FIG. 32, the fixation device 1010 is inserted into the intramedullary canal 6 so that the attachment portion 1016 is just inside the opening 4. The handle 1100 may be removed, or may remain attached to the device 1010 in preparation for a device expansion procedure. The guidewire 1150 may be removed by pulling it proximally along direction 1154, out of the intramedullary canal, the device 1010 and the handle 1100.

Alternatively, the device 1010 may be inserted into the intramedullary canal without the use of a guidewire. The device 1010 is heated to raise the thermoplastic matrix material 1048 to the first thermo-chemical state, attached to the handle 1100, and inserted into the canal. An expansion apparatus such as that described below may be present in the device 1010 prior to insertion, or it may be inserted into the central bore 1114 after the device 1010 is in the intramedullary canal.

Figure 33:
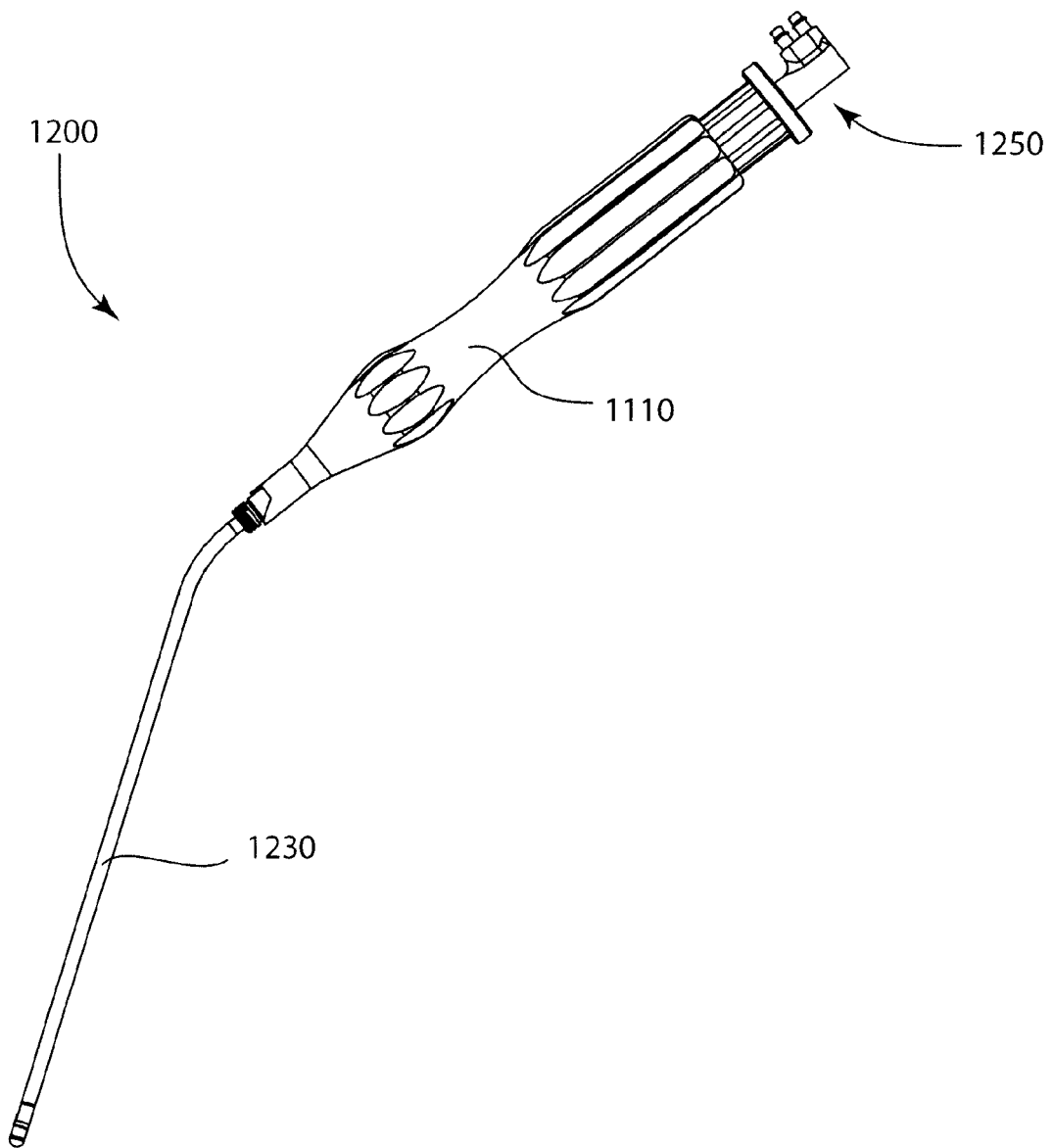
FIG. 33 is a lateral perspective view of the handle of FIG. 28A and a balloon expansion apparatus.

Referring to FIG. 33, an embodiment of a balloon expansion apparatus is shown. The expansion apparatus 1200 comprises a catheter-like inner tube 1210 (not visible in FIG. 33), a balloon 1230, the handle 1110, and a connection assembly 1250. The inner tube 1210 and balloon 1230 are configured to be assembled together co-axially, that is, the inner tube 1210 fits concentrically within the balloon 1230.

Figure 34:
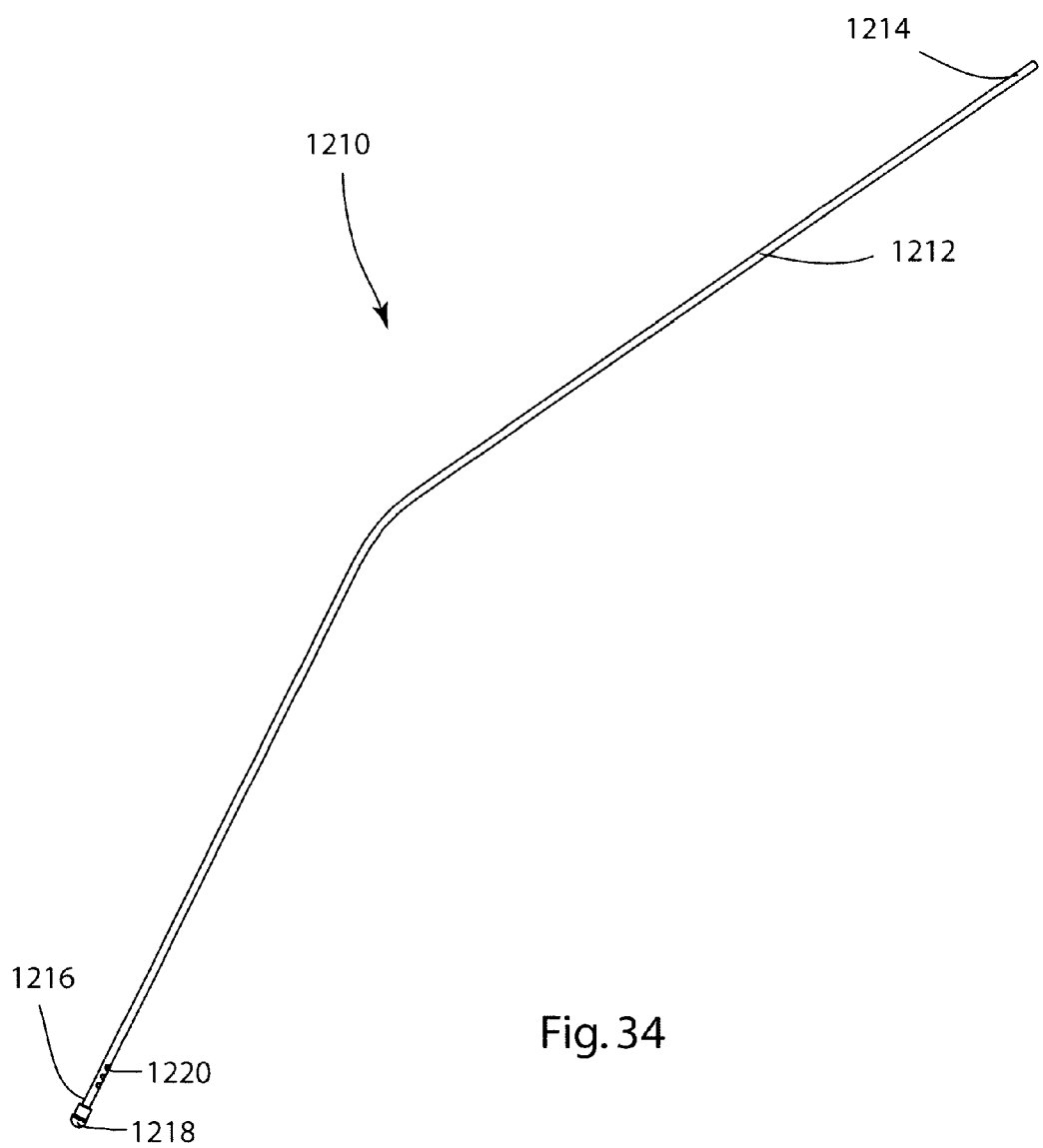
FIG. 34 is a lateral perspective view of a tube which comprises a portion of the balloon expansion apparatus of FIG. 33.

Referring to FIG. 34, the inner tube 1210 is shown. The inner tube 1210 is straw-like in configuration, with a tube body 1212 having a proximal end 1214 and a distal end 1216. The tube body 1212 may be constructed of a rigid material so that the length of the tube is fixed; it cannot lengthen or shorten along its longitudinal axis. Yet the tube body 1212 may simultaneously be bendable such that it can flex and bend along its transverse axis. Specifically, the tube body 1212 may be constructed of a linearly rigid, yet bendable material such as Nitinol. The flexibility allows the tube 1210 to be compliant enough to be inserted into the intramedullary canal. The linear rigidity prevents the tube 1210 from expanding longitudinally.

A bullet-shaped cap 1218 is at the distal end of the tube body 1212. Just proximal to the cap 1218, a series of ports 1220 perforate the tube body 1212. The ports 1220 are openings from the inside of the tube body 1212 to the outside, and may allow fluid to flow into, or out of, the inner tube.

Figure 35:
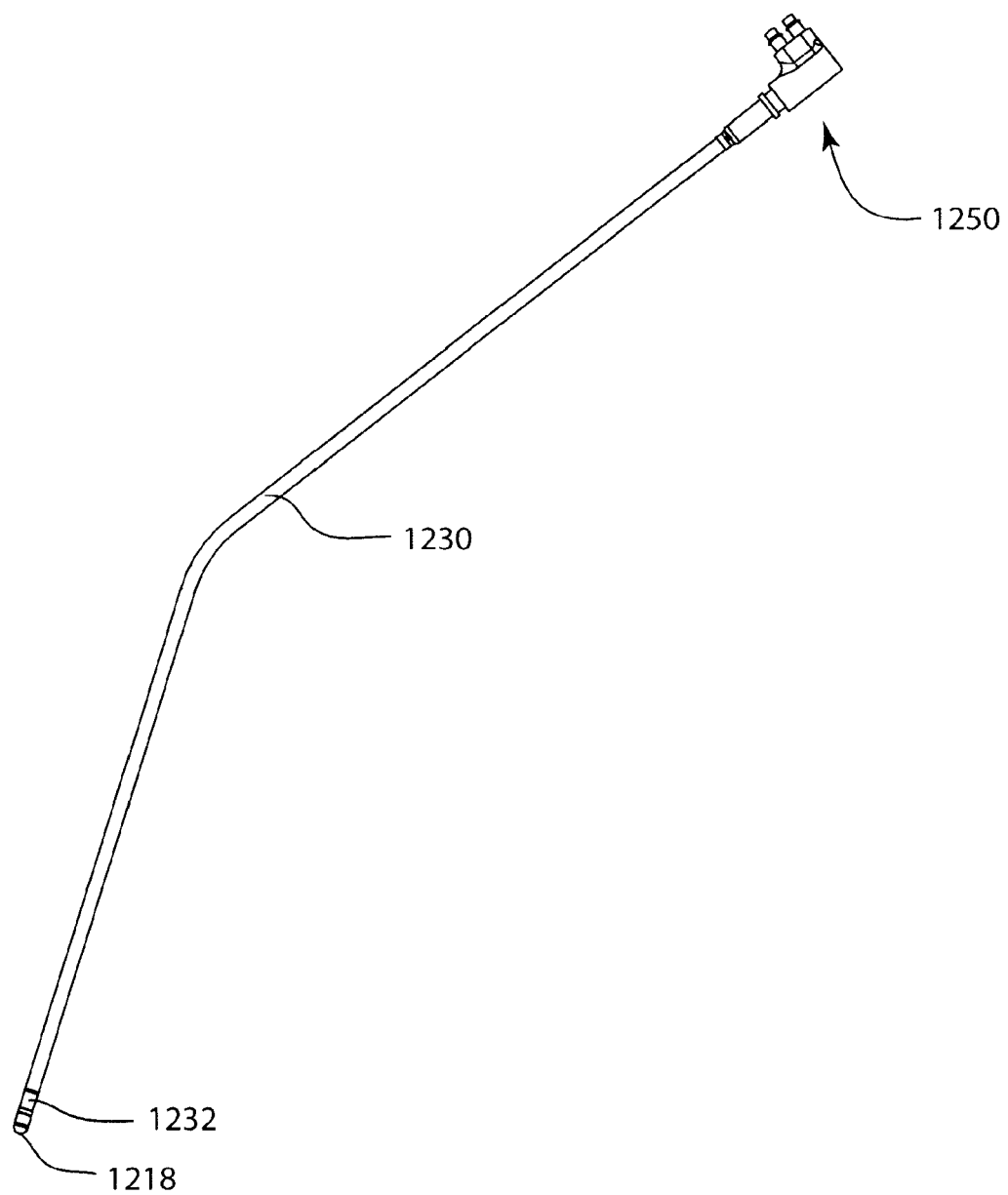
FIG. 35 is a lateral perspective view of the balloon expansion apparatus of FIG. 33.

Referring to FIG. 35, the balloon 1230 and the connection assembly 1250 are shown. The balloon 1230 is configured to fit over and encompass the inner tube 1210 (not visible), so that only the cap 1218 protrudes from the distal end of the balloon 1230. A ring-like distal fitting 1232 joins the inner tube 1210 to the balloon 1230 at their distal ends. The distal fitting 1232 tightly joins the tube and the balloon so that they may be manipulated as one during insertion and removal procedures. Additionally, because the more compliant balloon 1230 is joined to the linearly rigid inner tube 1210 at the distal fitting 1232, the balloon 1230 is prevented from expanding linearly when pressurized fluid is introduced into the tube and the balloon. The balloon 1230 may comprise an elastomeric polymer, such as polyurethane, latex, silicone, or another elastomeric polymer. Alternatively, the balloon 1230 may comprise a non-elastomeric polymer such as PET, UHWPE, or another non-elastomeric polymer.

Figure 36:
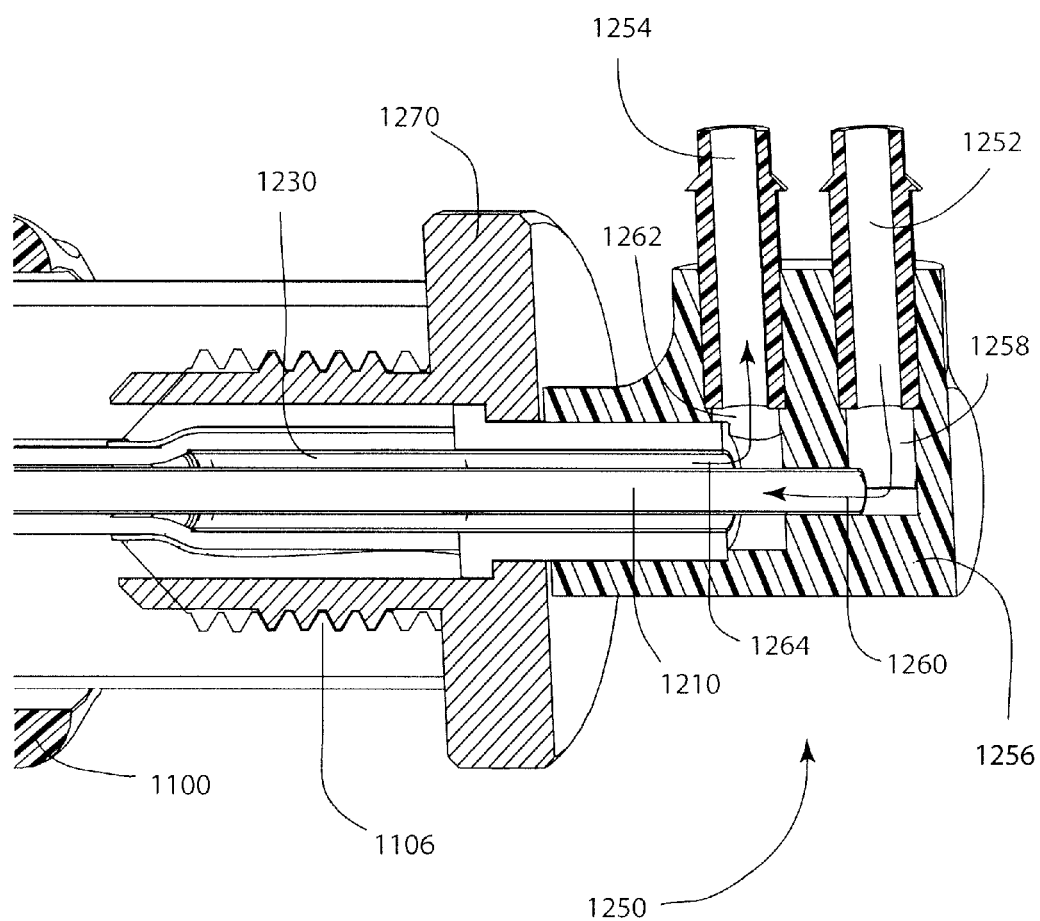
FIG. 36 is an enlarged cross-sectional view of a connection assembly of the balloon expansion apparatus of FIG. 33.

Referring to FIG. 36, a cross-sectional view of the proximal ends of the tube 1210, the balloon 1230, and the connection assembly 1250, is shown. A threaded ring 1270 connects the connection assembly 1250 to the proximal connection feature 1106 of the handle 1100. A connection housing 1256 encompasses the connections and may allow for convenient assembly of the connections. At their proximal ends, the inner tube 1210 protrudes for a short distance out of the balloon 1230. The proximal end of the inner tube 1210 opens into a first connector recess 1258, which is indented into the connection housing 1256. At a right angle to the inner tube 1210, an inflow fluid connector 1252 also opens into the first recess 1258. A first flow indicator arrow 1260 indicates how fluid may flow from the inflow fluid connector 1252 into the inner tube 1210. The proximal end of the balloon 1230 opens into a second connector recess 1262, which is indented into the connection housing 1256. At a right angle to the balloon 1230, an outflow fluid connector 1254 also opens into the second recess 1262. A second flow indicator arrow 1264 indicates how fluid may flow from the balloon 1230 into the outflow fluid connector 1254.

Figure 37:
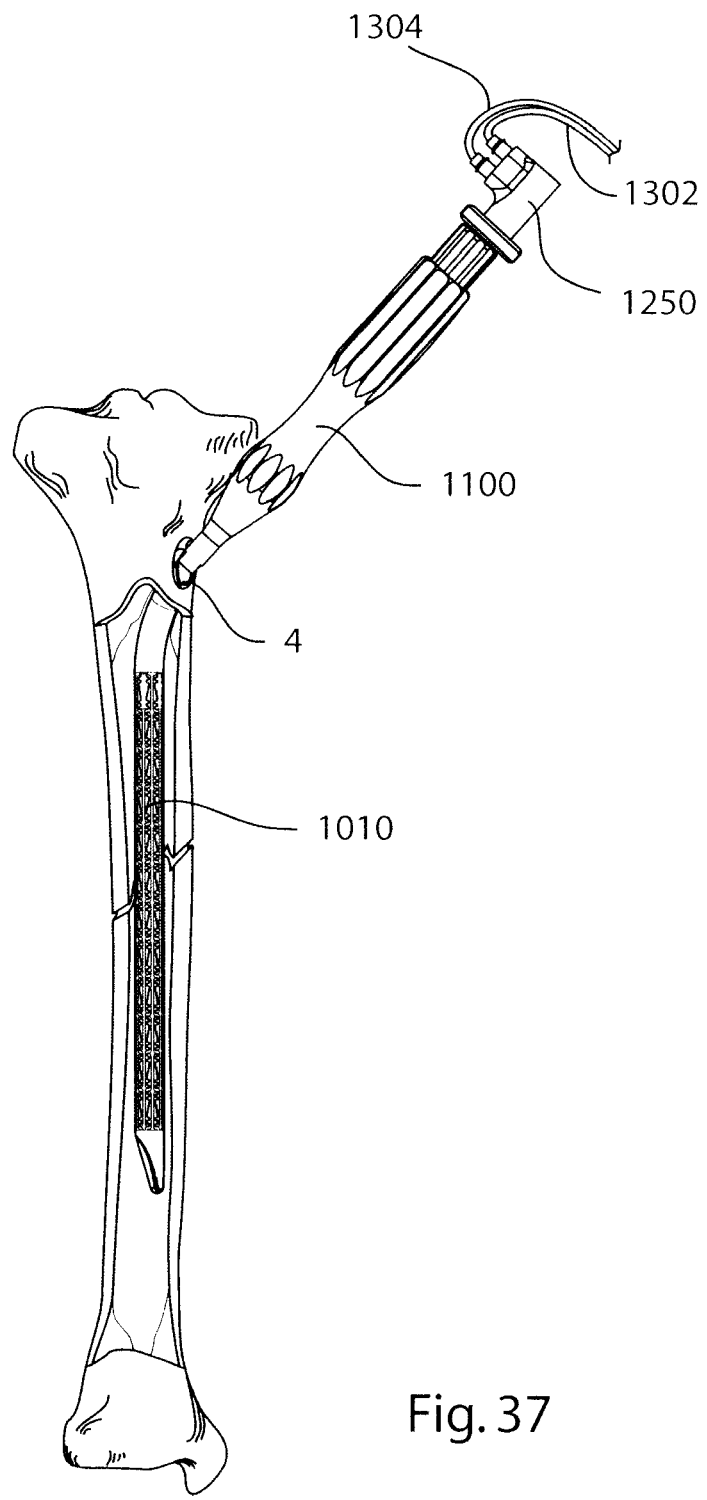
FIG. 37 is a lateral view of the composite intramedullary bone fixation device and the handle, connected to a set of hoses.

Referring to FIG. 37, the expansion apparatus 1200 is shown inserted into the fixation device 1010 in the intramedullary canal. The balloon 1230 and inner tube 1210 are not visible because they are surrounded by the fixation device 1010.

Insertion of the expansion apparatus may happen by a variety of methods. In a first method, after the fixation device 1010 is inserted into the intramedullary canal, the handle 1100 remains attached to the fixation device 1010, and the balloon 1230 and inner tube 1210 (connected at their proximal ends by the connection assembly 1250) are inserted through the handle and the fixation device. After they are fully inserted, the connection assembly 1250 is connected to the handle 1100 via the threaded ring 1270. Alternately, in a second method, the handle is detached from the fixation device. The balloon 1230 and the inner tube 1210 are inserted through the handle and attached via the threaded ring to the connection assembly 1250 and the handle 1100. Then, using the handle to control and guide, the balloon 1230 and the inner tube 1210 are inserted through the opening 4 and into the fixation device 1010.

Another method for implementing the expansion apparatus includes inserting the apparatus 1200 into the fixation device 1010 prior to inserting the fixation device 1010 into the intramedullary canal. The expansion apparatus 1200 is inserted into the fixation device 1010 and connection assembly 1250 is connected. Once the balloon assembly 1200 is inserted in the fixation device 1010, fluid hoses are connected to the connection assembly 1250. An input hose 1302 is connected to the input fluid connector 1252, and an output hose 1304 is connected to the output fluid connector 1254. Fluid is introduced into the expansion apparatus, and heated to in turn heat the fixation device 1010 until the thermoplastic matrix material 1048 attains the first thermo-chemical state. Temperature regulation continues as the device 1010 is inserted into the intramedullary canal, so that it remains warm enough to be substantially deformable and flexible to insert. Once the device 1010 is in the intramedullary canal, pressure may be increased within the device to cause radial expansion of the device. In an alternate embodiment of the invention, air instead of fluid may be heated and circulated through the expansion apparatus to warm the surrounding thermoplastic matrix.

Figure 38:
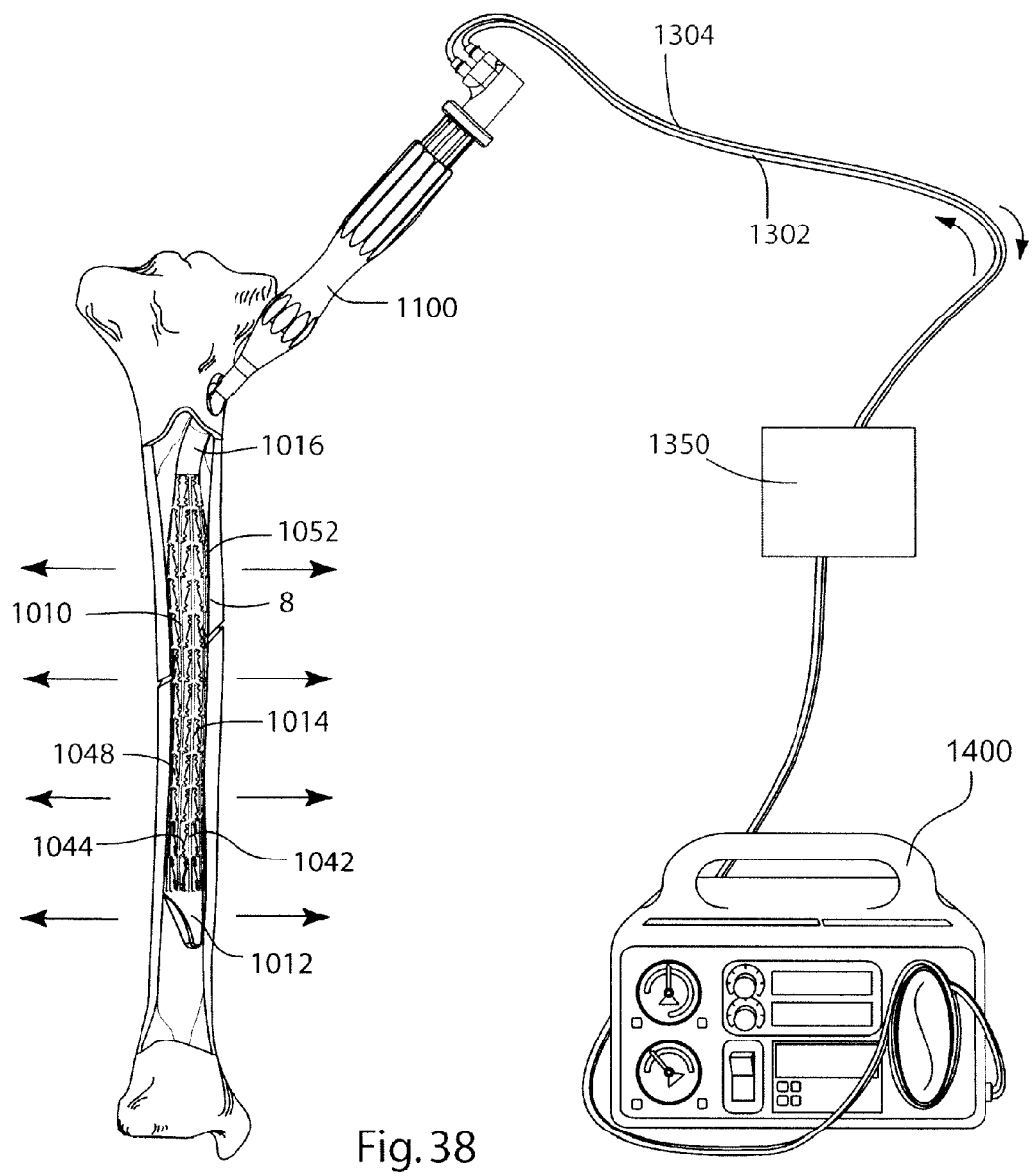
FIG. 38 is a lateral view of the composite intramedullary bone fixation device, handle, and hoses of FIG. 37, connected to a cartridge and a pump, and showing the expansion of a portion of the bone fixation device.

Referring to FIG. 38, the fixation device 1010 and balloon assembly 1200 (not visible in the figure; within the fixation device) are shown connected via the fluid hoses 1302, 1304 to a cartridge 1350, which in turn is connected to a pump 1400. Sterile saline solution, or another sterile, biocompatible fluid is provided to the pump via a bag or other container (not shown) connected to the pump 1400. The pump 1400 pumps the fluid to the cartridge 1350, which is capable to regulate the temperature and pressure of the fluid as it flows to and from the balloon assembly 1200. The cartridge 1350 may comprise heating and cooling sources capable to heat and/or cool the fluid before it enters the balloon assembly 1200. In an alternative embodiment, the hoses 1302, 1304 may be connected directly to the pump without the use of the cartridge 1350.

Following connection of the cartridge 1350 to the pump 1400 and the balloon assembly 1200, the balloon assembly may be expanded, to result in the radial expansion of the fixation device 1010 within the intramedullary canal. Fluid can flow through the balloon assembly in a continuous flow, flowing in through the input hose 1302 into the inner tube 1210, out the ports 1220 into the balloon 1230, and out of the balloon through the output hose 1304.

Fluid is supplied by the pump 1400 to the cartridge 1350 and pumped through the input hose 1302 into the inner tube 1210. At the distal end of the inner tube 1210, the fluid can move out of the tube 1210 through the ports 1220, and into the balloon 1230. As more fluid is added, the length of the balloon 1230 is filled and the balloon expands radially, contacting the inner bore wall 1050 of the matrix 1048 of the fixation device 1010. The heated fluid within the balloon 1230 heats the matrix 1048, transforming it from the substantially hardened second thermo-chemical state to the substantially deformable first thermo-chemical state. Pressure is maintained on the fluid in the balloon 1230, and the deformable heated matrix 1048 is expanded radially in response to the expansion of the balloon 1230. The outer wall 1052 of the matrix contacts the wall 8 of the intramedullary canal. The deformable heated matrix 1048 can conform to the specific morphology of the wall 8, filling in any irregularities in the wall. As the heated matrix 1048 expands, the embedded support structure 1040 also expands radially, allowed to by the configuration of the rods 1042 and the flexible struts 1044. The nose portion 1012 of the fixation device 1010 may also radially expand. The expanded diameters of the non-composite nose portion 1012 and the composite central portion 1014 may be the same, or alternatively, the central portion 1014 may expand to a greater expanded diameter than the nose portion 1012.

Figure 39:
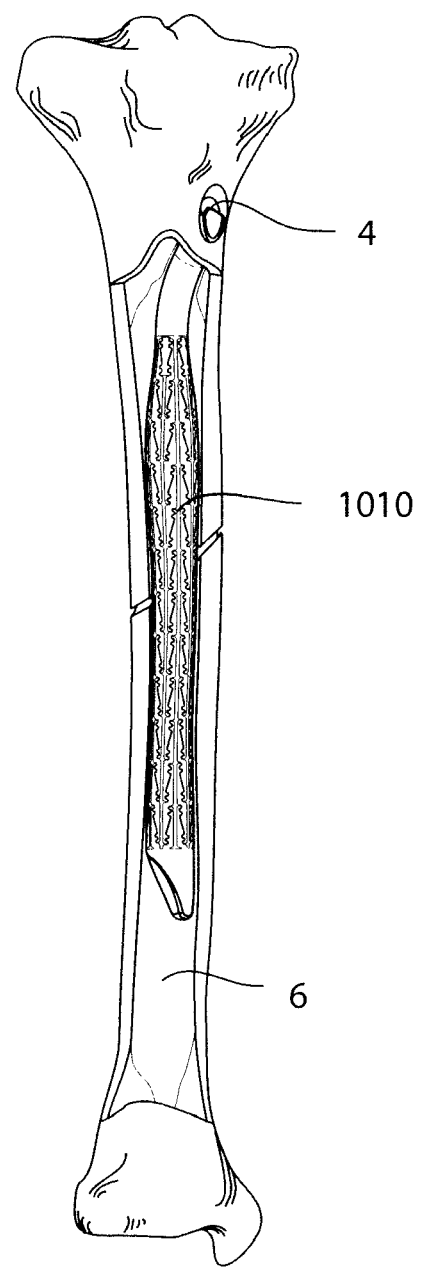
FIG. 39 is a lateral view of the expanded composite intramedullary bone fixation device in the intramedullary canal of the fractured bone.

Once the device 1010 is sufficiently radially expanded to provide support to the fractured bone, pressure is maintained and cooled fluid may be pumped through the balloon assembly. Fluid is cooled by the cartridge 1350 and pumped in through the input hose 1302. As the cooled fluid passes through the balloon 1230, the surrounding matrix 1048 is cooled, and attains the substantially hardened second thermo-chemical state. The hardened matrix 1048 holds the embedded support structure 1040 in its now expanded configuration, and together they provide support to the surrounding fractured bone. Once the matrix 1048 is sufficiently cooled and hardened, pressure is lowered and the fluid may be pumped out of the balloon and inner tube, and the balloon assembly withdrawn from the fixation device 1010. The handle 1100 is detached from the attachment end 1016 of the fixation device, leaving the now expanded fixation device 1010 in the intramedullary canal, as shown in FIG. 39. The opening 4 in the bone may be covered with a removable plug, and the tissues closed.

Positioning of the fixation device 1010 may be revisable if necessary. To revise or remove, the opening 4 may be re-opened, and a balloon expansion apparatus 1200 is attached to the handle 1100 and introduced into the bore 1114 of the fixation device 1010, and connected at the attachment connection feature 1036. The cartridge 1350 and pump 1400 are connected to the expansion apparatus 1200 via the connection assembly 1250, and heated fluid is introduced into the balloon 1230. Pressure is increased to inflate the balloon 1230, and the heated fluid warms the thermo-plastic matrix material 1048 until it is at the pliable first thermo-chemical state. The position of the fixation device 1010 may be revised by gripping the handle 1100 and moving the device 1010. Once the desired position is found, cool fluid is pumped through the device to cool the thermo-plastic matrix 1048 to the hardened second thermo-chemical state. The fluid pressure is lowered and the expansion apparatus is removed.

Alternately, removal instead of repositioning of the device 1010 may occur after warming the device to the first thermo-chemical state. The fluid pressure is lowered to contract the expansion apparatus 1200, and the device is pulled out through the opening 4. The warmed thermoplastic matrix material 1048 will be sufficiently deformable to allow the device 1010 to contract sufficiently as it passes out the opening 4.

Figure 40:
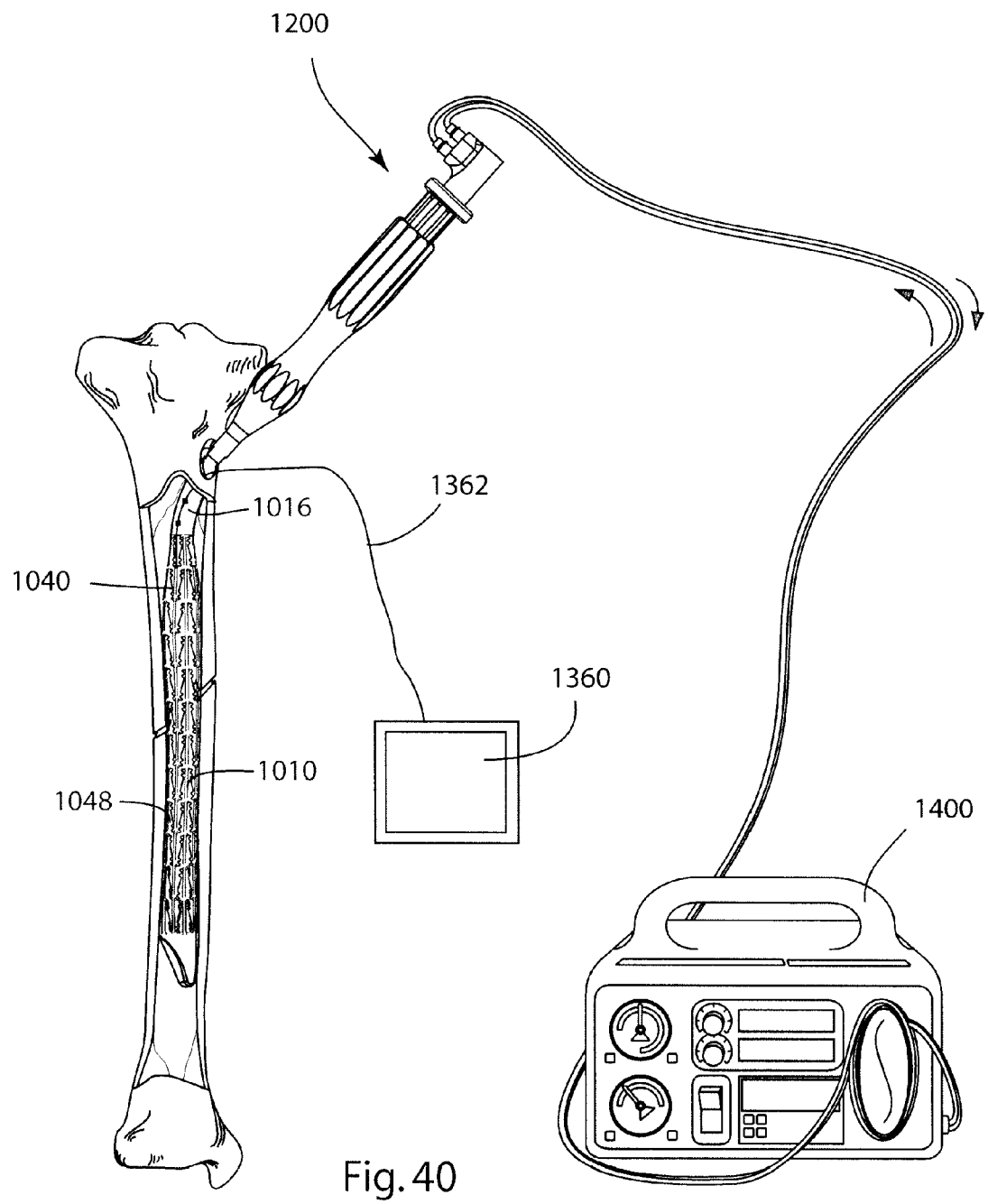
FIG. 40 is a perspective view of an implanted composite intramedullary bone fixation device connected to a heat source, an expansion apparatus and a pump.

FIGS. 40 through 43 illustrate alternative methods of heating the fixation device 1010 to raise the temperature of the thermoplastic matrix material 1048 to the substantially deformable first thermo-dynamic state. FIG. 40 depicts the fixation device 1010 with an external heat source 1360 connected by a lead 1362 to the attachment portion 1016 and the support structure 1040. Energy is conducted from the heat source 1360 to the support structure 1040, which increases in temperature and warms the surrounding thermoplastic matrix material 1048. An expansion apparatus such as expansion apparatus 1200 may be inserted into the fixation device 1010, connected to a pump such as pump 1400 and used to apply fluid or air pressure to expand the heated device.

Figure 41:
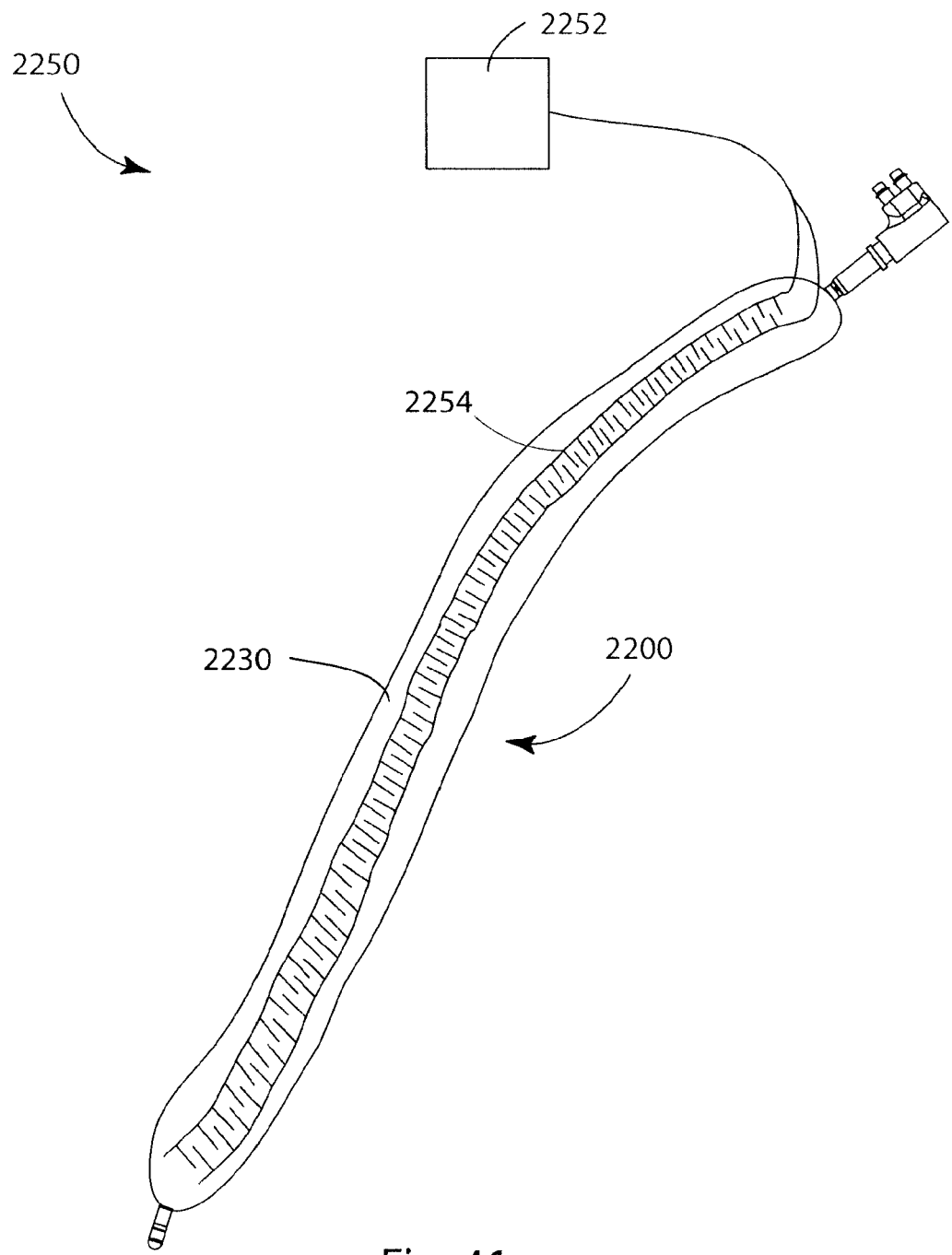
FIG. 41 is a perspective view of a balloon expansion apparatus with a heating mechanism integrated into the balloon.

FIG. 41 depicts a flexible, expandable heating system 2250 used in conjunction with a balloon expansion apparatus 2200 which is similar in structure to balloon expansion apparatus 1200. In FIG. 41, the balloon 2230 is shown as partially expanded so that details of the heating system may be seen. The expandable heating system 2250 may comprise a heat source 2252 and flexible conductive elements 2254 disposed on the external surface of the balloon 2230. Alternately, the flexible conductive elements may be integrated into the composition of the balloon. The conductive elements 2254 may comprise copper or another suitably conductive material. As the balloon is filled with fluid or air, heat is introduced from the heat source 2252 through the conductive elements 2254, heating the fluid or air within the balloon. The conductive elements 2254 are configured to flex and separate, without breaking, as the balloon expands. As the balloon expands within the fixation device 1010, heat from the fluid or air is transferred to the surrounding thermoplastic matrix material 1048. Heat may also transfer directly from the expandable heating system 2250 to the surrounding matrix material. Once the fixation device is sufficiently expanded, heat is turned off to the heating system 2250. Pressure is maintained in the balloon until the thermoplastic matrix cools to the hardened second thermo-chemical state. Then the air or fluid is removed, and the balloon expansion apparatus may be removed.

Figure 42:
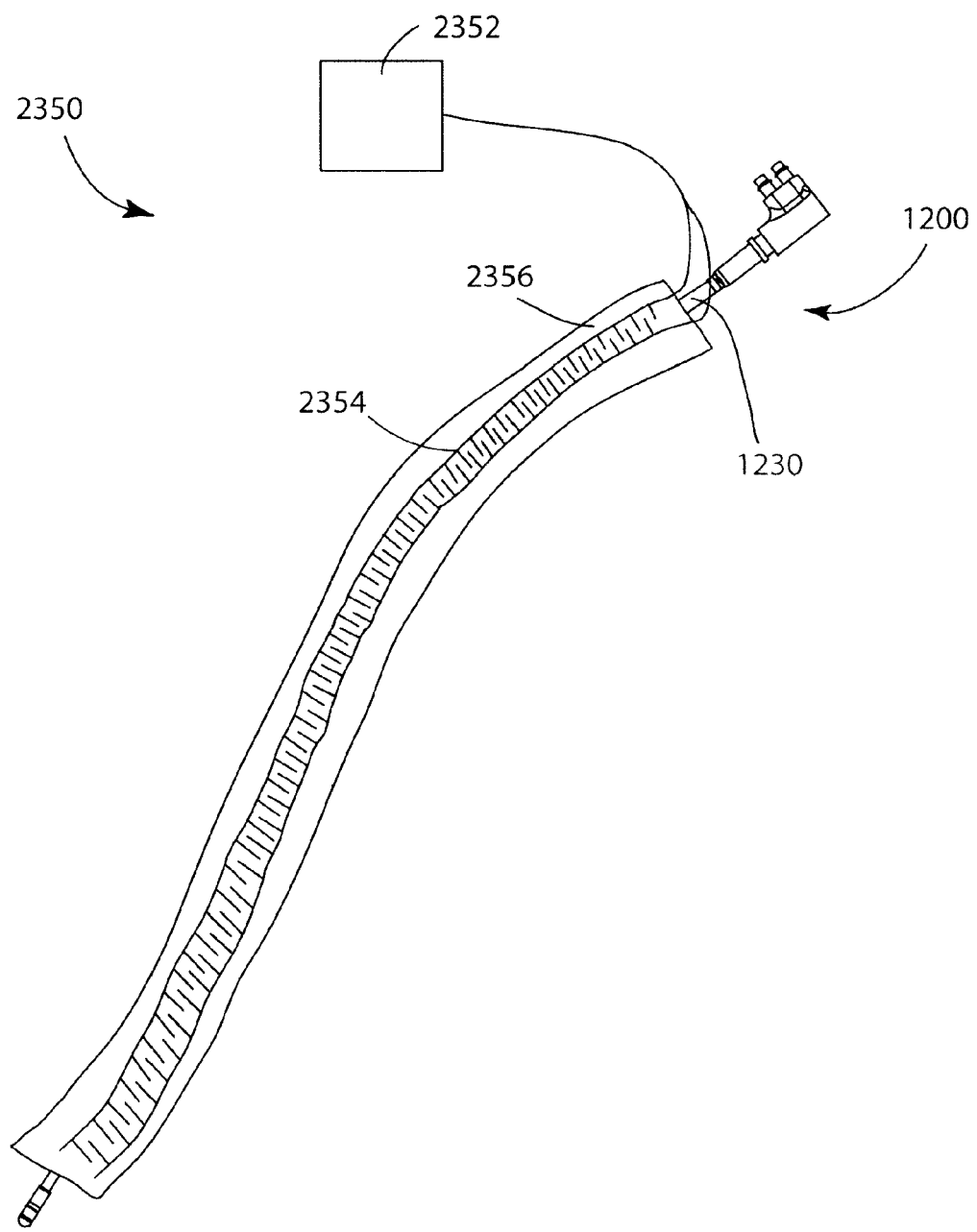
FIG. 42 is a perspective view of a balloon expansion apparatus with a heating mechanism integrated into a sleeve covering the balloon.

FIG. 42 depicts a heating system 2350 which is similar in operation to heating system 2250, except that it comprises a heat source 2352 and flexible heating elements 2354 disposed on an expandable sleeve 2356 which is separate from the balloon. Alternately, the flexible conductive elements may be integrated into the composition of the sleeve. The expandable sleeve 2356 is sized to fit over a balloon such as balloon 1230 of balloon expansion apparatus 1200 or a similar balloon. The expandable sleeve 2356 may be placed over the balloon 1230, and the sleeve and balloon inserted together into an intramedullary fixation device such as device 1010. As the balloon is filled with fluid or air, heat is introduced from the heat source 2352 through the flexible heating elements 2354, warming the fluid or air within the balloon. The heating elements 2354 are configured to flex and separate, without breaking, as the balloon expands. As the balloon expands within the fixation device 1010, heat from the fluid or air is transferred to the surrounding thermoplastic matrix material 1048. Heat may also transfer directly from the expandable heating system 2350 to the surrounding matrix material. Once the fixation device is sufficiently expanded, heat is turned off to the heating system 2350. Pressure is maintained in the balloon until the thermoplastic matrix cools to the hardened second thermo-chemical state. Then the air or fluid is removed, and the balloon expansion apparatus may be removed.

Alternatively, a rigid, or non-flexible sleeve with integrated heating elements (not shown) could be used in a manner similar to the expandable sleeve 2356. A non-flexible sleeve may be placed over a balloon expansion apparatus and inserted into an intramedullary fixation device such as those previously described. Heat is introduced through the heating elements, warming the surrounding thermoplastic matrix material. Once the material is sufficiently warmed to attain the first thermo-chemical state and becomes pliable, the non-flexible sleeve is removed, leaving the balloon expansion apparatus in the fixation device. The balloon expansion apparatus may then be expanded with pressurized fluid or air to expand the surrounding intramedullary fixation device.

Figure 43:
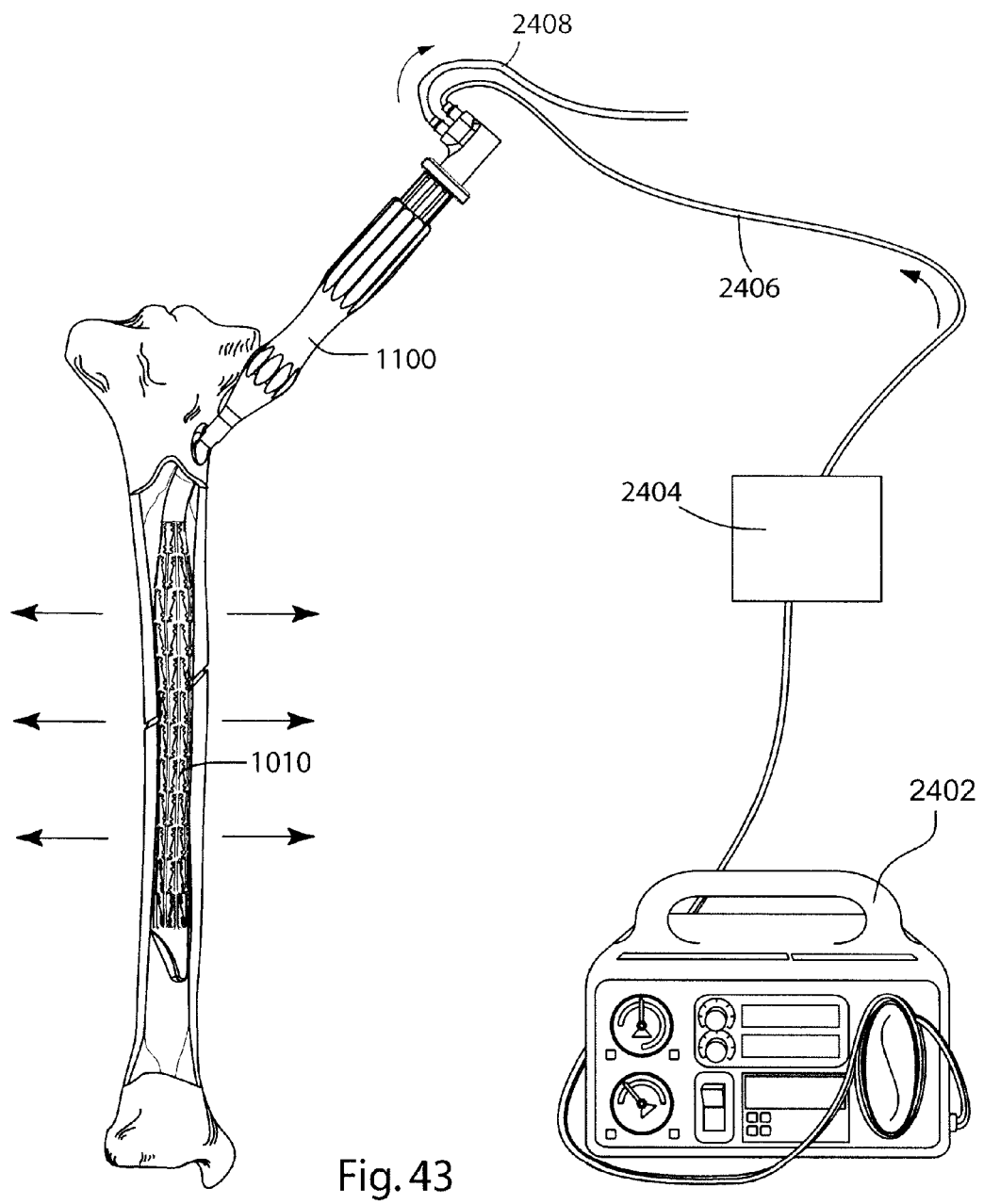
FIG. 43 is a perspective view of an implanted composite intramedullary bone fixation device and expansion apparatus connected to an air heating and pressure control system.

Referring to FIG. 43, an air heating and pressure control system 2400 is shown connected to the balloon expansion apparatus 1200 (not visible; inside the fixation device 1010) and fixation device 1010. Air heating and pressure control system 2400 comprises a pump 2402 which supplies and regulates pressure to the system, a heat source 2404 which supplies heat to the system, input hose 2406 which carries air into the expansion apparatus, and output hose 2408 which carries air out of the expansion apparatus. Air heating and pressure control system 2400 may work similarly to the cartridge 1350 and pump 1400 described previously, except that in this system air is heated and circulated throughout the balloon expansion apparatus instead of fluid.

The present invention may be embodied in other specific forms without departing from its spirit or essential characteristics. It is appreciated that various features of the above-described examples can be mixed and matched to form a variety of other alternatives. For example, support structure and matrix materials and configuration features can vary, as can the method used to expand the device. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for inserting a bone stabilization device into the intramedullary canal of a bone, the bone stabilization device including an elongated body configured for insertion into the intramedullary canal of a bone, the body having a first end, a second end, and a longitudinal axis extending between the first and second ends, the body including a polymer with a deformation temperature greater than 37 degrees Celsius, wherein the polymer is relatively deformable at a temperature above the deformation temperature and relatively rigid at a temperature below the deformation temperature, the device, while the polymer is at a temperature above the deformation temperature, being responsive to a bending force to bend during insertion into the intramedullary canal of the bone, and the device, while the polymer is at a temperature below the deformation temperature, being relatively rigid and able to provide reinforcement to the bone sufficient to promote healing of the fractured bone, the method comprising:

raising the temperature of the polymer above the deformation temperature so that the polymer is relatively deformable;

after raising the temperature of the polymer above the deformation temperature, inserting the bone stabilization device into the intramedullary canal of the bone; and after inserting the bone stabilization device into the intramedullary canal of the bone, lowering the temperature of the polymer below the deformation temperature so that the polymer is relatively rigid and able to provide reinforcement to the bone.

2. The method of claim 1 wherein lowering the temperature of the polymer comprises allowing time for the polymer to dissipate heat to the surrounding bone.

3. The method of claim 1 wherein lowering the temperature of the polymer comprises actively cooling the polymer by removing heat from the polymer via a heat removal apparatus.

4. The method of claim 1 wherein inserting the bone stabilization device into the intramedullary canal of the bone comprises inserting the device through a delivery tube.

5. The method of claim 1 wherein inserting the bone stabilization device into the intramedullary canal of the bone comprises inserting the device over a guidewire.

6. The method of claim 1 wherein inserting the bone stabilization device includes deforming the bone stabilization device while it is above the deformation temperature so that it conforms to a non-linear insertion path into the bone.

* * * * *